US010457733B2

(12) United States Patent
Freeman et al.

(10) Patent No.: US 10,457,733 B2
(45) Date of Patent: Oct. 29, 2019

(54) AGENTS THAT MODULATE IMMUNE CELL ACTIVATION AND METHODS OF USE THEREOF

(71) Applicants: Dana-Farber Cancer Institute, Inc., Boston, MA (US); Boston Children's Hospital, Boston, MA (US); President and Fellows of Harvard College, Cambridge, MA (US)

(72) Inventors: Gordon J. Freeman, Brookline, MA (US); Arlene H. Sharpe, Brookline, MA (US); Yanping Xiao, Brookline, MA (US); Loise Francisco, Belmont, MA (US); Rosemarie Dekruyff, Newton, MA (US); Dale Umetsu, Newton, MA (US)

(73) Assignees: Dana-Farber Cancer Institute, Inc., Boston, MA (US); President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 14/418,548

(22) PCT Filed: Aug. 2, 2013

(86) PCT No.: PCT/US2013/053393

§ 371 (c)(1),
(2) Date: Jan. 30, 2015

(87) PCT Pub. No.: WO2014/022759

PCT Pub. Date: Feb. 6, 2014

(65) Prior Publication Data

US 2015/0299322 A1 Oct. 22, 2015

Related U.S. Application Data

(60) Provisional application No. 61/742,137, filed on Aug. 3, 2012.

(51) Int. Cl.

| | |
|---|---|
| ***C07K 16/00*** | (2006.01) |
| ***C07K 16/28*** | (2006.01) |
| ***G01N 33/50*** | (2006.01) |
| ***A61K 39/395*** | (2006.01) |
| ***A61K 45/06*** | (2006.01) |
| ***C07K 14/705*** | (2006.01) |
| ***G01N 33/68*** | (2006.01) |
| *A61K 39/00* | (2006.01) |

(52) U.S. Cl.

CPC ...... *C07K 16/2827* (2013.01); *A61K 39/3955* (2013.01); *A61K 45/06* (2013.01); *C07K 14/705* (2013.01); *C07K 14/70532* (2013.01); *C07K 16/28* (2013.01); *G01N 33/5041* (2013.01); *G01N 33/5047* (2013.01); *G01N 33/6872* (2013.01); *A61K 2039/505* (2013.01); *C07K 2317/565* (2013.01); *C07K 2317/76* (2013.01); *C07K 2319/30* (2013.01); *G01N 2333/4703* (2013.01); *G01N 2333/70596* (2013.01); *G01N 2500/02* (2013.01); *G01N 2500/10* (2013.01); *G01N 2500/20* (2013.01)

(58) Field of Classification Search

CPC .................................................... C07K 16/00
USPC ..................................................... 530/387.1
See application file for complete search history.

(56) References Cited

U.S. PATENT DOCUMENTS

| | | | | |
|---|---|---|---|---|
| 2004/0014141 A1 | 1/2004 | Woolf et al. | | |
| 2008/0118511 A1 | 5/2008 | Freeman et al. | | |
| 2008/0213277 A1 * | 9/2008 | Sasu | ................. | A61K 39/3955 424/141.1 |
| 2009/0297527 A1 | 12/2009 | Muller et al. | | |
| 2010/0183608 A1 | 7/2010 | Woolf et al. | | |
| 2010/0209467 A1 | 8/2010 | Carlson et al. | | |
| 2011/0271358 A1 | 11/2011 | Freeman et al. | | |

FOREIGN PATENT DOCUMENTS

| | | |
|---|---|---|
| WO | WO-2004/073732 A1 | 9/2004 |
| WO | WO-2009/030500 A1 | 3/2009 |

OTHER PUBLICATIONS

Samad et al (JBC, 2006, 280(14): 14122-14129.*
Akbari et al (Mucosal Immunology, 2010, 3(1): 81-91).*
Baumhoer et al., "MicroRNA profiling with correlation to gene expression revealed the oncogenic miR-17-92 cluster to be up-regulated in osteosarcoma," Cancer Genetics, 205:212-219 (2012).
Conrad et al., "RGMb controls aggregation and migration of Neogenin-positive cells in vitro and in vivo," Molecular and Cellular Neuroscience, 43:222-231 (2010).
Corradini et al., "The RGM/DRAGON family of BMP co-receptors," Cytokine & Growth Factor Reviews, 20:389-398 (2009).
GenBank Database, BC091272.1 (Apr. 5, 2005).
Guo et al., "Signaling cross-talk between TGF-β/BMP and other pathways," Cell Research, 19:71-88 (2009).
Hagihara et al., "Neogenin, a Receptor for bone Morphogenetic Proteins," J. Biol. Chem. 286(7):5157-5165 (2011).
Heinecke et al., "Receptor oligomerization and beyond: a case study in bone morphogenetic proteins," BMC Biology, 7:1-20 (2009).
Liu et al., "Repulsive guidance molecule b inhibits neurite growth and is increased after spinal cord injury," Biochemical and Biophysical Research Communications, 382:795-800 (2009).
Martinez et al., "The canonical BMP signaling pathway is involved in human monocyte-derived dendritic cell maturation," Immunology and Cell Biology, 89:610-618 (2011).
Wu et al., "Repulsive Guidance Molecule (RGM) Family Proteins Exhibit Differential Binding Kinetics for Bone Morphogenetic Proteins (BMPs)," PLoS One, 7(9):e46307 (2012).

(Continued)

*Primary Examiner* — Sean E Aeder
(74) *Attorney, Agent, or Firm* — Foley Hoag LLP

(57) ABSTRACT

The present invention relates to compositions and methods for the immunomodulation mediated by the interaction of PD-L2 and RGMb.

18 Claims, 15 Drawing Sheets

Specification includes a Sequence Listing.

(56) References Cited

OTHER PUBLICATIONS

Xiao et al., "RGMb is a novel binding partner for PD-L2 and its engagement with PD-L2 promotes respiratory tolerance," J. Exp. Med., 211(5):943-959 (2014).
International Search Report dated Dec. 16, 2013 from PCT/US2013/053393.
Supplementary European Search Report dated Jan. 26, 2016 from EP 13826362.9.

* cited by examiner

AGENTS THAT MODULATE IMMUNE CELL ACTIVATION AND METHODS OF USE THEREOF

CROSS-REFERENCE TO RELATED APPLICATIONS

The present application is the U.S. National Stage Application of International Application No. PCT/US2013/053393, filed on Aug. 2, 2013, which claims the benefit of priority to U.S. Provisional Application No. 61/742,137, filed on Aug. 3, 2012; the entire content of each of which application is incorporated herein in its entirety by this reference.

STATEMENT OF RIGHTS

This invention was made with government support under grant numbers AI056299 and 5HSSN266200500030C awarded by The National Institutes of Health. The government has certain rights in the invention.

BACKGROUND OF THE INVENTION

In order for immune cells, such as T cells, to respond to foreign proteins, two signals must be provided by antigen-presenting cells (APCs) to resting T lymphocytes (Jenkins, M. and Schwartz, R. (1987) *J. Exp. Med.* 165:302-319; Mueller, D. L. et al. (1990) *J. Immunol.* 144:3701-3709). The first signal, which confers specificity to the immune response, is transduced via the T cell receptor (TCR) following recognition of foreign antigenic peptide presented in the context of the major histocompatibility complex (MHC). The second signal, termed costimulation, induces T cells to proliferate and become functional (Lenschow et al. (1996) *Annu. Rev. Immunol.* 14:233). Costimulation is neither antigen-specific, nor MHC restricted and is thought to be provided by one or more distinct cell surface polypeptides expressed by APCs (Jenkins, M. K. et al. (1988) *J. Immunol.* 140:3324-3330; Linsley, P. S. et al. (1991) *J. Exp. Med.* 173:721-730; Gimmi, C. D., et al. 1991 *Proc. Natl. Acad. Sci. USA* 88:6575-6579; Young. J. W. et al. (1992) *J. Clin. Invest.* 90:229-237; Koulova, L. et al. (1991) *J. Exp. Med.* 173:759-762; Reiser, H. et al. (1992) *Proc. Natl. Acad. Sci. USA* 89:271-275; van-Seventer, G. A. et al. (1990) *J. Immunol.* 144:4579-4586; LaSalle, J. M. et al. (1991) *J. Immunol.* 147:774-80; Dustin, M. I. et al. (1989) *J. Exp. Med.* 169:503; Armitage. R. J. et al. (1992) *Nature* 357:80-82: Liu, Y. et al. (1992) *J. Exp. Med.* 175:437-445).

Such immune cells have receptors that transmit immunomodulatory (e.g., costimautory and coinhibitory) signals. For example, T cells have T cell receptors and the CD3 complex, B cells have B cell receptors, and myeloid cells have Fc receptors. In addition, immune cells bear receptors that transmit signals that provide costimulatory signals, or receptors that transmit signals that inhibit receptor-mediated signaling. For example, CD28 transmits a costimulatory signal to T cells. After ligation of the T cell receptor, ligation of CD28 results in a costimulatory signal characterized by, e.g., upregulation of IL-2rα, IL-2rβ, and IL-2rγ receptor, increased transcription of IL-2 messenger RNA, and increased expression of cytokine genes (including IL-2, IFN-γ, GM-CSF, and TNF-α). Transmission of a costimulatory signal allows the cell to progress through the cell cycle and, thus, increases T cell proliferation (Greenfield et al. (1998) *Crit. Rev. Immunol.* 18:389). Binding of a receptor on a T cell which transmits a costimulatory signal to the cell (e.g., ligation of a costimulatory receptor that leads to cytokine secretion and/or proliferation of the T cell) by a B7 family molecule, such as B7-1 or B7-2, results in costimulation. Thus, inhibition of an interaction between a B7 family molecule, such as B7-1 or B7-2, and a receptor that transmits a costimulatory signal on an immune cell results in a downmodulation of the immune response, specific unresponsiveness, termed immune cell anergy, clonal deletion, and/or exhaustion. Inhibition of this interaction can be accomplished using, e.g., anti-CD28 Fab fragments, antibodies to B7-1 or B7-2, or by using a soluble form of a receptor to which a B7 family member molecule can bind as a competitive inhibitor (e.g., CTLA41g).

Inhibitory receptors that bind to costimulatory molecules have also been identified on immune cells. Activation of CTLA4, for example, transmits a negative signal to aT cell. Engagement of CTLA4 inhibits IL-2 production and can induce cell cycle arrest (Krummel and Allison (1996) *J. Exp. Med.* 183:2533). In addition, mice that lack CTLA4 develop lymphoproliferative disease (Tivol, et al. (1995) *Immunity* 3:541; Waterhouse et al. (1995) *Science* 270:985). The blockade of CTLA4 with antibodies can block an inhibitory signal, whereas aggregation of CTLA4 with antibody transmits an inhibitory signal. Therefore, depending upon the receptor to which a costimulatory molecule binds (i.e., a costimulatory receptor such as CD28 or an 30 inhibitory receptor such as CTLA4), certain B7 molecules including B7-4 can promote T cell costimulation or inhibition.

PD-1 is a member of the immunoglobulin family of molecules (Ishida et al. (1992) *EMBO J.* 11:3887; Shinohara et al. (1994) *Genomics* 23:704). PD-1 was previously identified using a subtraction cloning based approach designed to identify modulators of programmed cell death (Ishida et al. (1992) *EMBO J.* 11:3887-95; 5 Woronicz et al. (1995) *Curr. Top. Microbial. Immunol.* 200:137). PD-1 is believed to play a role in lymphocyte survival, e.g., during clonal selection (Honjo (1992) *Science* 258:591; Agata et al. (1996) *Int. Immunology.* 8:765; Nishimura et al. (1996) *Int. Immunology* 8:773). PD-1 was also implicated as a regulator of B cell responses (Nishimura (1998) *Int. Immunology* 10:1563). Unlike CTLA4, which is found only on T cells, PD-1 is also found on B cells and myeloid cells. The previous discovery that PD-1 binds to PD-1 ligands, such as PD-L1 and PD-L2, placed PD-1 in a family of inhibitory receptors with CTLA4. While engagement of a costimulatory receptor results in a costimulatory signal in an immune cell, engagement of an inhibitory receptor, e.g., CTLA4 or PD-1 (for example by crosslinking or by 15 aggregation), leads to the transmission of an inhibitory signal in an immune cell, resulting in downmodulation of immune cell responses and/or in immune cell anergy. While transmission of an inhibitory signal leads to downmodulation in immune cell responses (and a resulting downmodulation in the overall immune response), the prevention of an inhibitory signal in cells, such as immune cells leads, to upmodulation of immune cell responses (and a resulting upmodulation of an immune response).

It is currently unknown whether coinhibitory receptors and ligands exist, especially because such well-known molecules involved in mediating coinhibitory signals and resulting downregulation of immune responses (e.g., CTLA4, PD-1, PD-L1, PD-L2, etc.) do not account for the full spectrum of observed immunoinhibitory responses. Accordingly, there is a need to identify additional coinhibitory receptors and/or ligands that play physiologically important roles in regulating immune responses.

SUMMARY OF THE INVENTION

The present invention is based, at least in part, on the discovery that RGMb is a receptor for the PD-1 ligand, PD-L2. PD-L2 polypeptides are expressed on the surface of antigen presenting cells and can transmit downmodulatory signals to immune cells. For example. PD-L2 ligand binding to PD-1 is known to transmit a negative signal. It is demonstrated herein that RGMb similarly transmits a negative signal to cells (e.g., immune or cancer cells) upon interacting with PD-L2. Thus, modulation of the interaction between RGMb and PD-L2 results in modulation of the immune response.

In one aspect, a method for modulating an immune response comprising contacting a cell expressing PD-L2 or a cell expressing RGMb with an agent that modulates the interaction of PD-L2 with RGMb to thereby modulate the immune response, is provided. In one embodiment, the cell expressing PD-L2 and/or the cell expressing RGMb is a human cell. In another embodiment, the cell expressing PD-L2 and/or the cell expressing RGMb is an immune cell, such as a T cell, a B cell, or a myeloid cell. In still another embodiment, the immune response is upregulated (e.g., by using an agent selected from the group consisting of: a blocking antibody that binds RGMb, a non-activating form of RGMb, a soluble form of RGMb, an RGMb fusion protein, a nucleic acid molecule that blocks RGMb transcription or translation, a small molecule RGMb antagonist, a blocking antibody that recognizes PD-L2, a non-activating form of PD-L2, a soluble form of PD-L2, a PD-L2 fusion protein, a nucleic acid molecule that blocks RGMb and/or PD-L2 transcription or translation, a small molecule PD-L2 antagonist, a non-activating form of a natural RGMb ligand, a soluble form of a natural RGMb ligand, and a natural RGMb ligand fusion protein). In yet another embodiment, the blocking antibody that binds PD-L2 is selected from the group consisting of anti-PD-L2 antibodies that block the interaction between PD-L2 and RGMb without blocking the interaction between PD-L2 and PD-1; and anti-PD-L2 antibodies that block both the interaction between PD-L2 and RGMb and the interaction between PD-L2 and PD-1. In another embodiment, anergy, exhaustion, and/or clonal deletion is reduced in the immune cell. In still another embodiment, the method further comprises contacting the cell or immune cell with one or more additional agents that upregulates an immune response. In yet another embodiment, the immune response is downregulated (e.g., by using an agent selected from the group consisting of: an activating antibody that binds RGMb, a small molecule RGMb agonist, an activating antibody that binds PD-L2, a small molecule PD-L2 agonist, and a blocking antibody that binds PD-1 and inhibits the interaction between PD-L2 and PD-1). In another embodiment, the activating antibody that binds PD-L2 is selected from the group consisting of anti-PD-L2 antibodies that promote the interaction between PD-L2 and RGMb without promoting the interaction between PD-L2 and PD-1; and anti-PD-L2 antibodies that promote both the interaction between PD-L2 and RGMb and the interaction between PD-L2 and PD-1. In still another embodiment, the blocking antibody that binds PD-1 is selected from the group consisting of anti-PD-1 antibodies that block the interaction between PD-L2 and PD-1 without blocking the interaction between PD-L1 and PD-1; and anti-PD-1 antibodies that block both the interaction between PD-L2 and PD-1 and the interaction between PD-L1 and PD-1. In yet another embodiment, anergy, exhaustion, and/or clonal deletion is induced in the immune cell. In another embodiment, the method further comprises contacting the immune cell with one or more additional agents that downregulates an immune response. In still another embodiment, the step of contacting occurs in vivo, ex vivo, or in vitro.

In another aspect, a method of treating a subject having a condition that would benefit from upregulation of an immune response comprising administering to the subject an agent that inhibits the interaction between RGMb and PD-L2 such that the condition that would benefit from upregulation of an immune response is treated, is provided. In one embodiment, the agent is selected from the group consisting of: a blocking antibody that binds RGMb, a non-activating form of RGMb, a soluble form of RGMb, an RGMb fusion protein, a nucleic acid molecule that blocks RGMb transcription or translation, a small molecule RGMb antagonist, a blocking antibody that recognizes PD-L2, a non-activating form of PD-L2, a soluble form of PD-L2, a PD-L2 fusion protein, a nucleic acid molecule that blocks RGMb and/or PD-L2 transcription or translation, a small molecule PD-L2 antagonist, a non-activating form of PD-1, a soluble form of PD-1, a PD-1 fusion protein, and a small molecule PD-1 agonist. In another embodiment, the blocking antibody that binds PD-L2 is selected from the group consisting of anti-PD-L2 antibodies that block the interaction between PD-L2 and RGMb without blocking the interaction between PD-L2 and PD-1; and anti-PD-L2 antibodies that block both the interaction between PD-L2 and RGMb and the interaction between PD-L2 and PD-1. In still another embodiment, anergy, exhaustion, and/or clonal deletion is reduced in the immune cell. In yet another embodiment, the method further comprises contacting the cell or immune cell with one or more additional agents that upregulates an immune response. In another embodiment, the condition that would benefit from upregulation of an immune response is selected from the group consisting of cancer, a viral infection, a bacterial infection, a protozoan infection, a helminth infection, asthma associated with impaired airway tolerance, a neurological disease, multiple sclerosis, and an immunosuppressive disease.

In still another aspect, a method for treating a subject having a condition that would benefit from downregulation of an immune response comprising administering to the subject an agent that stimulates PD-L2-mediated signaling via an RGMb in a immune cell of the subject such that a condition that would benefit from downregulation of the immune response is treated, is provided. In one embodiment, the agent is selected from the group consisting of: an activating antibody that binds RGMb, a small molecule RGMb agonist, an activating antibody that binds PD-L2, a small molecule PD-L2 agonist, a blocking antibody that binds PD-1 and inhibits the interaction between PD-L2 and PD-1, a nucleic acid molecule that blocks PD-1 transcription or translation, and a small molecule PD-1 antagonist. In another embodiment, the activating antibody that binds PD-L2 is selected from the group consisting of anti-PD-L2 antibodies that promote the interaction between PD-L2 and RGMb without promoting the interaction between PD-L2 and PD-1; and anti-PD-L2 antibodies that promote both the interaction between PD-L2 and RGMb and the interaction between PD-L2 and PD-1. In still another embodiment, the blocking antibody that binds PD-1 is selected from the group consisting of anti-PD-1 antibodies that block the interaction between PD-L2 and PD-1 without blocking the interaction between PD-L1 and PD-1; and anti-PD-1 antibodies that block both the interaction between PD-L2 and PD-1 and the interaction between PD-L1 and PD-1. In yet another embodiment, anergy, exhaustion, and/or clonal deletion is induced in the immune cell. In another embodiment, the method further comprises contacting the immune cell with one or more additional agents that downregulates an immune response. In another embodiment, the condition that would benefit from downregulation of the immune response is selected from the group consisting of an allergy (e.g., food allergies), a transplant, graft versus host disease, hypersensitivity response, an autoimmune disorder, a disorder requiring increased CD4+ T cell production or function, a disorder requiring improved vaccination efficiency, a disorder requiring increased regulatory T cell production or function, and a disorder requiring improved vaccination efficiency.

In yet another aspect, a method for screening for compounds which modulate the binding of PD-L2 to RGMb comprising contacting (a) a cell expressing PD-L2 with an RGMb protein; (b) a cell expressing RGMb with a PD-L2 protein: (c) a cell expressing PDL-2 with a cell expressing RGMb, or (d) a PD-L2 or RGMb protein, or biologically active portion thereof, with a test compound and determining the ability of the test compound to modulate the binding between PD-L2 and RGMb, is provided. In one embodiment, the cell is an immune cell selected from the group consisting of a T cell, a B cell, and a myeloid cell.

In another aspect, a method for screening for compounds which modulate the signaling activity resulting from the interaction between PD-L2 to RGMb comprising contacting (a) a cell expressing PD-L2 with an RGMb protein; (b) a cell expressing RGMb with a PD-L2 protein; (c) a cell expressing PDL-2 with a cell expressing RGMb, or (d) a PD-L2 or RGMb protein, or biologically active portion thereof, with a test compound and determining the ability of the test compound to modulate one or more signaling activities selected from the group consisting of modulating FoxP3 expression, modulating phosphorylation of ERK1 or ERK2, modulating phosphorylation of PKC-θ, modulating phosphorylation of SHP-2, modulating cytokine production, and modulating cellular proliferation, is provided. In one embodiment, the test compound has an effect selected from the group consisting of (a) upregulates PD-L2/RGMb signaling and thereby downregulates ERK 1 or ERK 2 phosphorylation; (b) downregulates PD-L2/RGMb signaling and thereby upregulates ERK 1 or ERK 2 phosphorylation; (c) upregulates PD-L2/RGMb signaling and thereby downregulates PKC-θ phosphorylation; (d) downregulates PD-L2/RGMb signaling and thereby upregulates PKC-θ phosphorylation; (e) upregulates PD-L2/RGMb signaling and thereby upregulates SHSP-2 phosphorylation; and (f) downregulates PD-L2/RGMb signaling and thereby downregulates SHP-2 phosphorylation. In another embodiment, the cell is an immune cell selected from the group consisting of a T cell, a B cell, and a myeloid cell.

In still another aspect, a cell-based assay for screening for compounds which modulate the binding of PD-L2 to RGMb comprising contacting (a) a cell expressing PD-L2 with an RGMb protein; (b) a cell expressing RGMb with a PD-L2 protein; or (c) a cell expressing PDL-2 with a cell expressing RGMb, with a test compound and determining the ability of the test compound to modulate the binding between PD-L2 and RGMb, is provided. In one embodiment, the cell is an immune cell selected from the group consisting of a T cell, a B cell, and a myeloid cell.

In yet another aspect, a cell-free assay for screening for compounds which modulate the binding of PD-L2 to RGMb comprising contacting a PD-L2 or RGMb protein, or biologically active portion thereof, with a test compound and determining the ability of the test compound to modulate the binding between the PD-L2 or RGMb protein, or biologically active portion thereof, is provided.

In another aspect, a cell-based assay for screening for compounds which modulate the signaling activity resulting from the interaction between PD-L2 and RGMb comprising contacting (a) a cell expressing PD-L2 with an RGMb protein; (b) a cell expressing RGMb with a PD-L2 protein; or (c) a cell expressing PDL-2 with a cell expressing RGMb, with a test compound and determining the ability of the test compound to modulate one or more signaling activities selected from the group consisting of modulating FoxP3 expression, modulating phosphorylation of ERK1 or ERK2, modulating phosphorylation of PKC-θ, modulating phosphorylation of SHP-2, modulating cytokine production, and modulating cellular proliferation, is provided. In one embodiment, the cell is an immune cell selected from the group consisting of a T cell, a B cell, and a myeloid cell.

In still another aspect, a cell-free assay for screening for compounds which modulate the binding of PD-L2 to RGMb comprising contacting a PD-L2 or RGMb protein, or biologically active portion thereof, with a test compound and determining the ability of the test compound to modulate one or more signaling activities selected from the group consisting of modulating FoxP3 expression, modulating phosphorylation of ERK1 or ERK2, modulating phosphorylation of PKC-θ, modulating phosphorylation of SHP-2, modulating cytokine production, and modulating cellular proliferation, is provided.

In yet another aspect, an isolated anti-RGMb antibody, or antigen-binding fragment thereof, that inhibits the interaction between RGMb and PD-L2, is provided. In one embodiment, the antibody is a monoclonal antibody, such as a monoclonal antibody deposited as a hybridoma clone and assigned an accession number. In another embodiment, the monoclonal antibody comprises: a) a heavy chain sequence with at least about 95% identity to a heavy chain sequence selected from the group consisting of the sequences listed in Table 3 or b) a light chain sequence with at least about 95% identity to a light chain sequence selected from the group consisting of the sequences listed in Table 3. In still another embodiment, the monoclonal antibody comprises: a) a heavy chain CDR sequence with at least about 95% identity to a heavy chain CDR sequence selected from the group consisting of the sequences listed in Table 3 or b) a light chain CDR sequence with at least about 95% identity to a light chain sequence CDR sequence selected from the group consisting of the sequences listed in Table 3. In yet another embodiment, the monoclonal antibody comprises: a) a heavy chain sequence selected from the group consisting of the sequences listed in Table 3; or b) a light chain sequence selected from the group consisting of the sequences listed in Table 3. In another embodiment, the monoclonal antibody comprises: a) a heavy chain CDR sequence selected from the group consisting of the sequences listed in Table 3; or b) a light chain CDR sequence selected from the group consisting the sequences listed in Table 3. In still another embodiment, the anti-RGMb antibody or antigen-binding fragment thereof is monoclonal, chimeric, humanized, composite, rodent, or human. In yet another embodiment, the anti-RGMb antibody or antigen-binding fragment thereof reduces or inhibits at least one activity relative to the absence of the monoclonal antibody or antigen-binding fragment thereof selected from the group consisting of modulating FoxP3 expression, modulating phosphorylation of ERK1 or ERK2, modulating phosphorylation of PKC-θ, modulating phosphorylation of SHP-2, modulating cytokine production, and modulating cellular proliferation. In another embodiment, the monoclonal antibody or antigen-binding fragment thereof is detectably labeled, comprises an effector domain, comprises an Fc domain, and/or is selected from the group consisting of Fv, Fav, F(ab')2), Fab', dsFv, scFv, sc(Fv)2, and diabodies fragments.

In another aspect, an immunoglobulin heavy and/or light chain of antibodies described herein are provided.

In still another aspect, an isolated nucleic acid molecule that hybridizes, under stringent conditions, with the complement of a nucleic acid encoding a polypeptide selected from the group consisting of the sequences listed in Table 3, or a sequence with at least about 95% homology to a nucleic acid encoding a polypeptide selected from the group consisting of the sequences listed in Table 3, is provided.

In yet another aspect, a vector comprising an isolated nucleic acid described herein is provided.

In another aspect, a host cell which comprises an isolated nucleic acid described herein, vector described herein, expresses an antibody or antigen-binding fragment thereof described herein, or is accessible according to a deposit described herein, is provided.

In still another aspect, a device or kit comprising at least one antibody or antigen-binding fragment thereof described herein, said device or kit optionally comprising a label to detect the at least one antibody or antigen-binding fragment thereof, or a complex comprising the antibody or antigen-binding fragment thereof, is provided.

In yet another aspect, a method of producing an antibody described herein, which method comprises the steps of: (i) culturing a transformed host cell which has been transformed by a nucleic acid comprising a sequence encoding the antibody described herein under conditions suitable to allow expression of said antibody; and (ii) recovering the expressed antibody, is provided.

In another aspect, a method of detecting the presence or level of an RGMb polypeptide said method comprising obtaining a sample and detecting said polypeptide in a sample by use of at least one antibody or antigen-binding fragment thereof described herein, is provided. In one embodiment, the at least one antibody or antigen-binding fragment thereof forms a complex with an RGMb polypeptide and the complex is detected in the form of an enzyme linked immunosorbent assay (ELISA), radioimmune assay (RIA), immunochemically, or using an intracellular flow assay.

BRIEF DESCRIPTION OF THE DRAWINGS

FIG. 9A-91 show that blockade of RGMb:PD-L2 interaction impairs T cell expansion to antigen during the development of respiratory tolerance.

DETAILED DESCRIPTION OF THE INVENTION

I. Definitions

Figure 1:
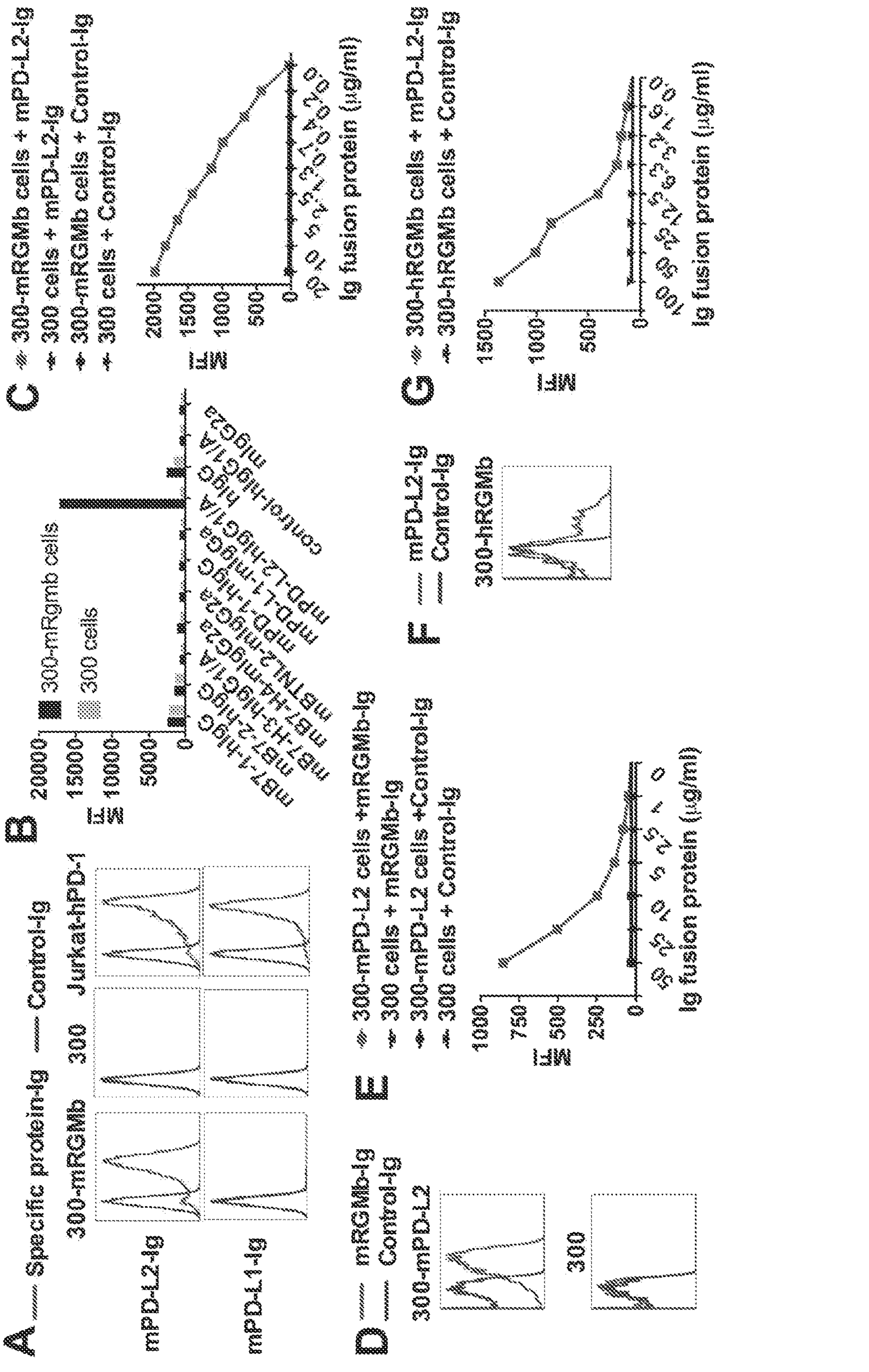
FIGS. 1A-1R show that RGMb Binds to PD-L2, but not to PD-L1 or other related molecules.
Figure 1:
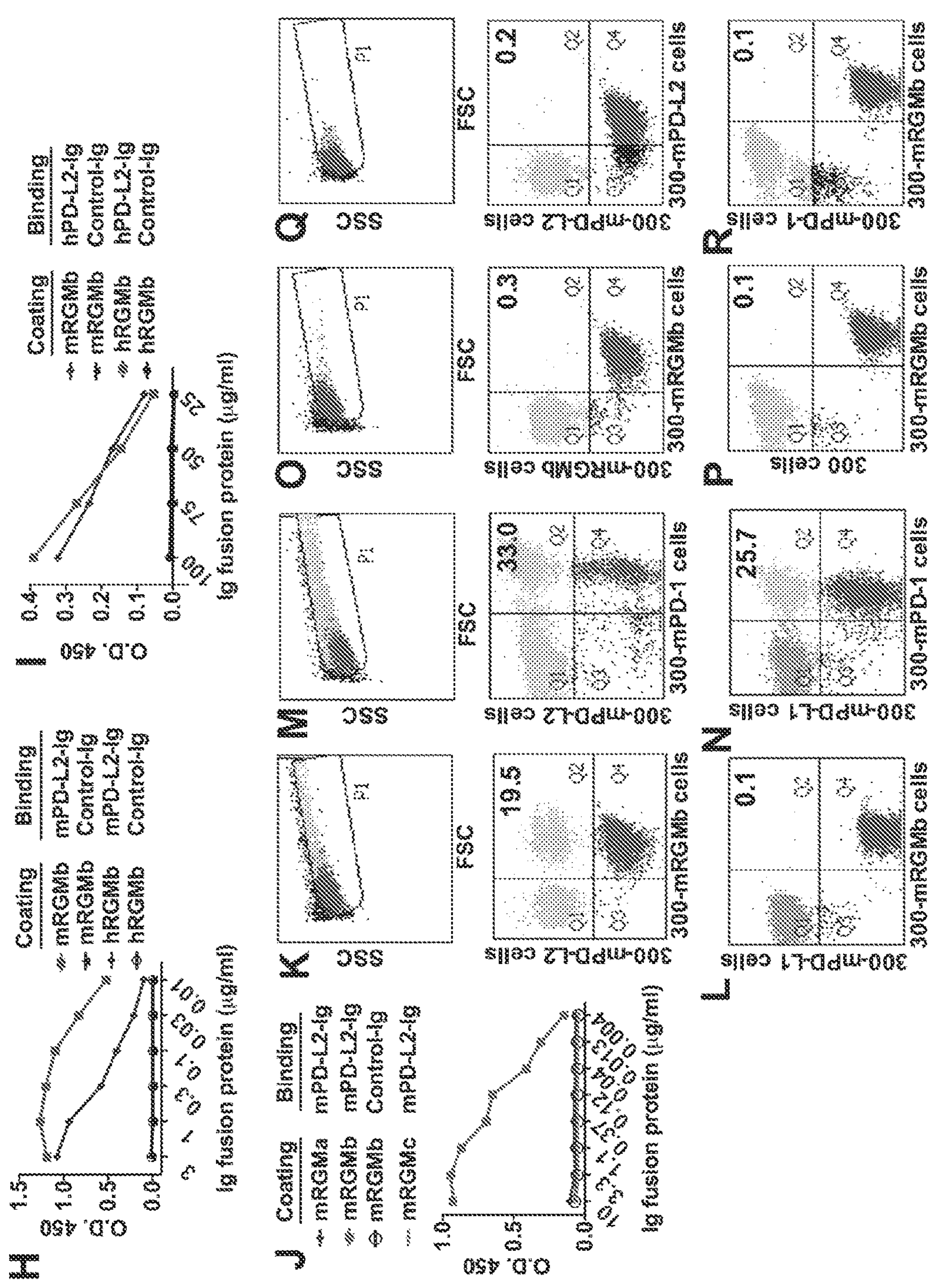
Figure 2:
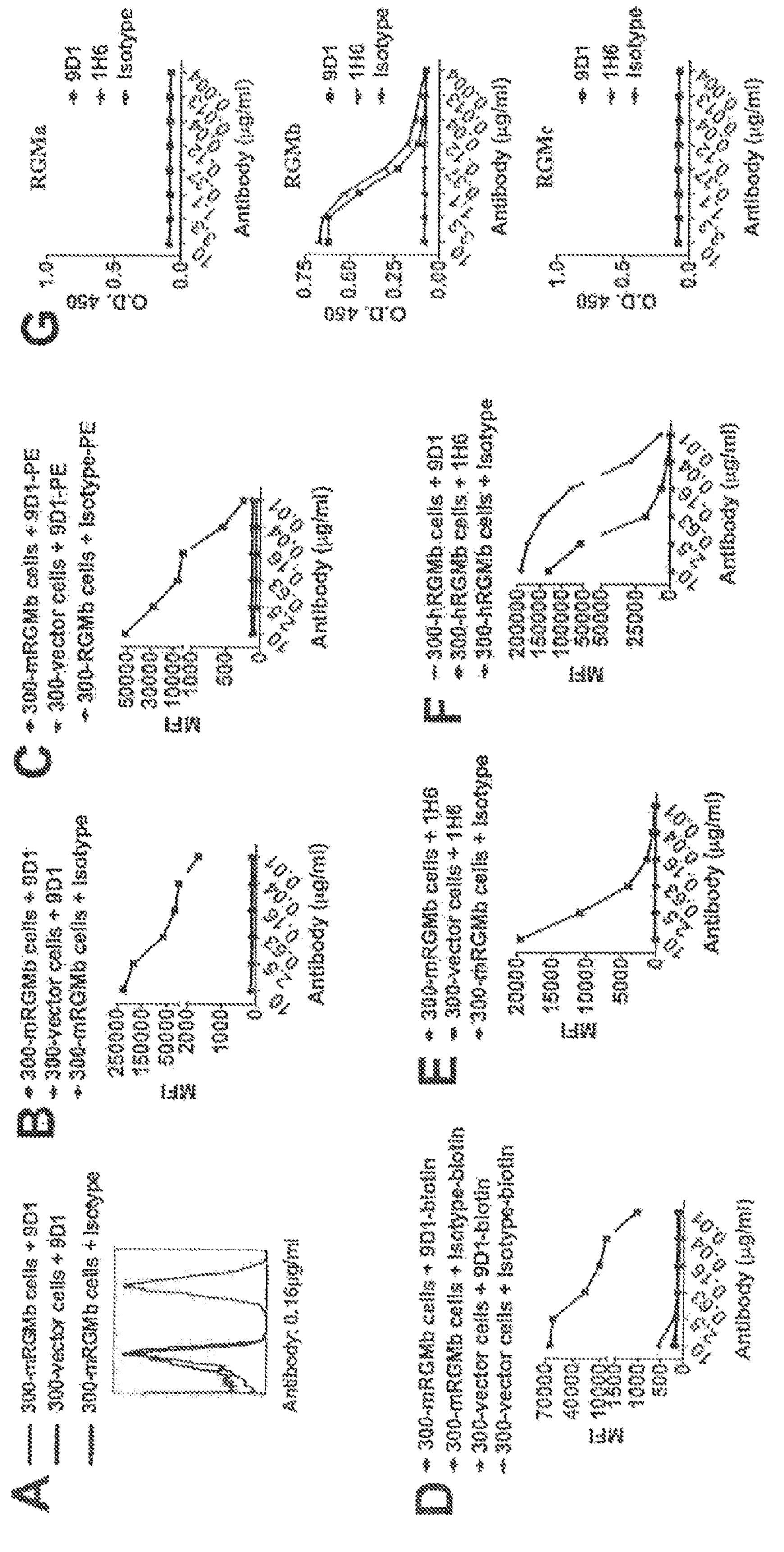
FIGS. 2A-2G show that anti-RGMb antibodies bind to RGMb, but not to RGMa or RGMc.

The articles "a" and "an" are used herein to refer to one or to more than one (i.e. to at least one) of the grammatical object of the article. By way of example, "an element" means one element or more than one element.

The term "activating receptor" includes immune cell receptors that bind antigen, complexed antigen (e.g., in the context of MHC polypeptides), or bind to antibodies. Such activating receptors include T cell receptors (TCR), B cell receptors (BCR), cytokine receptors, LPS receptors, complement receptors, and Fc receptors.

T cell receptors are present on T cells and are associated with CD3 polypeptides. T cell receptors are stimulated by antigen in the context of MHC polypeptides (as well as by polyclonal T cell activating reagents). T cell activation via the TCR results in numerous changes, e.g., protein phosphorylation, membrane lipid changes, ion fluxes, cyclic nucleotide alterations, RNA transcription changes, protein synthesis changes, and cell volume changes.

B cell receptors are present on B cells. B cell antigen receptors are a complex between membrane Ig (mIg) and other transmembrane polypeptides (e.g., Igα and Igβ). The signal transduction function of mIg is triggered by cross-linking of receptor polypeptides by oligomeric or multimeric antigens. B cells can also be activated by anti-immunoglobulin antibodies. Upon BCR activation, numerous changes occur in B cells, including tyrosine phosphorylation.

Fc receptors are found on many cells which participate in immune responses. Fc receptors (FcRs) are cell surface receptors for the Fc portion of immunoglobulin polypeptides (Igs). Among the human FcRs that have been identified so far are those which recognize IgG (designated Fcγ R), IgE (Fcε RI), IgA (Fcα), and polymerized IgM/A (Fcμα R). FcRs are found in the following cell types: Fcε R I (mast cells), Fcε R.II (many leukocytes). Fcα R (neutrophils), and Fcμα R (glandular epithelium, hepatocytes) (Hogg, N. (1988) *Immunol. Today* 9:185-86). The widely studied FcγRs are central in cellular immune defenses, and are responsible for stimulating the release of mediators of inflammation and hydrolytic enzymes involved in the pathogenesis of autoimmune disease (Unkeless, J. C. et al. (1988) *Annu. Rev. Immunol.* 6:251-81). The FcγRs provide a crucial link between effector cells and the lymphocytes that secrete Ig, since the macrophage/monocyte, polymorphonuclear leukocyte, and natural killer (NK) cell FcγRs confer an element of specific recognition mediated by IgG. Human leukocytes have at least three different receptors for IgG: h Fcγ RI (found on monocytes/macrophages), hFcγ RII (on monocytes, neutrophils, eosinophils, platelets, possibly B cells, and the K562 cell line), and Fcγ III (on NK cells, neutrophils, eosinophils, and macrophages).

With respect to T cells, transmission of a costimulatory signal to a T cell involves a signaling pathway that is not inhibited by cyclosporine A. In addition, a costimulatory signal can induce cytokine secretion (e.g., IL-2 and/or IL-10) in a T cell and/or can prevent the induction of unresponsiveness to antigen, the induction of anergy, or the induction of cell death (deletion) in the T cell.

The term "activity," when used with respect to a polypeptide, e.g., PD-L2, PD-L1, PD-1, or RGMb polypeptide includes activities that are inherent in the structure of the protein. For example, with regard to a PD-1 ligand, the term "activity" includes the ability to modulate immune cell costimulation (e.g. by modulating a costimulatory signal in an activated immune cell) or to modulate inhibition by modulating an inhibitory signal in an immune cell (e.g., by engaging a natural receptor on an immune cell). Those of skill in the art will recognize that when an activating form of the PD-1 ligand polypeptide binds to an inhibitory receptor, an inhibitory signal is generated in the immune cell.

The term "altered level of expression" of a marker refers to an expression level or copy number of a marker in a test sample e.g., a sample derived from a subject suffering from cancer, that is greater or less than the standard error of the assay employed to assess expression or copy number, and is preferably at least twice, and more preferably three, four, five or ten or more times the expression level or copy number of the marker or chromosomal region in a control sample (e.g., sample from a healthy subject not having the associated disease) and preferably, the average expression level or copy number of the marker or chromosomal region in several control samples. The altered level of expression is greater or less than the standard error of the assay employed to assess expression or copy number, and is preferably at least twice, and more preferably three, four, five or ten or more times the expression level or copy number of the marker in a control sample (e.g., sample from a healthy subject not having the associated disease) and preferably, the average expression level or copy number of the marker in several control samples.

The term "altered activity" of a marker refers to an activity of a marker which is increased or decreased in a disease state, e.g., in a cancer sample, as compared to the activity of the marker in a normal, control sample. Altered activity of a marker may be the result of, for example, altered expression of the marker, altered protein level of the marker, altered structure of the marker, or, e.g., an altered interaction with other proteins involved in the same or different pathway as the marker, or altered interaction with transcriptional activators or inhibitors.

The "amount" of a marker, e.g., expression or copy number of a marker or MCR, or protein level of a marker, in a subject is "significantly" higher or lower than the normal amount of a marker, if the amount of the marker is greater or less, respectively, than the normal level by an amount greater than the standard error of the assay employed to assess amount, and preferably at least twice, and more preferably three, four, five, ten or more times that amount. Alternately, the amount of the marker in the subject can be considered "significantly" higher or lower than the normal amount if the amount is at least about two, and preferably at least about three, four, or five times, higher or lower, respectively, than the normal amount of the marker.

Unless otherwise specified herein, the terms "antibody" and "antibodies" broadly encompass naturally-occurring forms of antibodies (e.g., IgG, IgA, IgM, IgE) and recombinant antibodies such as single-chain antibodies, chimeric and humanized antibodies and multi-specific antibodies, as well as fragments and derivatives of all of the foregoing, which fragments and derivatives have at least an antigenic binding site. Antibody derivatives may comprise a protein or chemical moiety conjugated to an antibody.

The term "antibody" as used herein also includes an "antigen-binding portion" of an antibody (or simply "antibody portion"). The term "antigen-binding portion", as used herein, refers to one or more fragments of an antibody that retain the ability to specifically bind to an antigen. It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a $F(ab')_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent polypeptides (known as single chain Fv (scFv); see e.g., Bird et al. (1988) *Science* 242:423-426; and Huston et al. (1988) *Proc. Natl. Acad. Sci. USA* 85:5879-5883; and Osbourn et al. 1998, Nature Biotechnology 16: 778). Such single chain antibodies are also intended to be encompassed within the term "antigen-binding portion" of an antibody. Any VH and VL sequences of specific scFv can be linked to human immunoglobulin constant region cDNA or genomic sequences, in order to generate expression vectors encoding complete IgG polypeptides or other isotypes. VH and VL can also be used in the generation of Fab, Fv or other fragments of immunoglobulins using either protein chemistry or recombinant DNA technology. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad. Sci. USA* 90:6444-6448; Poljak, R. J., et al. (1994) *Structure* 2:1121-1123).

Still further, an antibody or antigen-binding portion thereof may be part of larger immunoadhesion polypeptides, formed by covalent or noncovalent association of the antibody or antibody portion with one or more other proteins or peptides. Examples of such immunoadhesion polypeptides include use of the streptavidin core region to make a tetrameric scFv polypeptide (Kipriyanov, S. M., et al. (1995) *Human Antibodies and Hybridomas* 6:93-101) and use of a cysteine residue, a marker peptide and a C-terminal poly-histidine tag to make bivalent and biotinylated scFv polypeptides (Kipriyanov, S. M., et al. (1994) *Mol. Immunol.* 31:1047-1058). Antibody portions, such as Fab and $F(ab')_2$ fragments, can be prepared from whole antibodies using conventional techniques, such as papain or pepsin digestion, respectively, of whole antibodies. Moreover, antibodies, antibody portions and immunoadhesion polypeptides can be obtained using standard recombinant DNA techniques, as described herein.

Antibodies may be polyclonal or monoclonal; xenogeneic, allogeneic, or syngeneic; or modified forms thereof (e.g., humanized, chimeric, etc.). Antibodies may also be fully human. The terms "monoclonal antibodies" and "monoclonal antibody composition", as used herein, refer to a population of antibody polypeptides that contain only one species of an antigen binding site capable of immunoreacting with a particular epitope of an antigen, whereas the term "polyclonal antibodies" and "polyclonal antibody composition" refer to a population of antibody polypeptides that contain multiple species of antigen binding sites capable of interacting with a particular antigen. A monoclonal antibody composition typically displays a single binding affinity for a particular antigen with which it immunoreacts. In addition, antibodies can be "humanized," which includes antibodies made by a non-human cell having variable and constant regions which have been altered to more closely resemble antibodies that would be made by a human cell. For example, by altering the non-human antibody amino acid sequence to incorporate amino acids found in human germline immunoglobulin sequences. The humanized antibodies of the invention may include amino acid residues not encoded by human germline immunoglobulin sequences (e.g., mutations introduced by random or site-specific mutagenesis in vitro or by somatic mutation in vivo), for example in the CDRs. The term "humanized antibody," as used herein, also includes antibodies in which CDR sequences derived from the germline of another mammalian species, such as a mouse, have been grafted onto human framework sequences.

The term "antisense" nucleic acid polypeptide comprises a nucleotide sequence which is complementary to a "sense" nucleic acid encoding a protein, e.g., complementary to the coding strand of a double-stranded cDNA polypeptide, complementary to an mRNA sequence or complementary to the coding strand of a gene. Accordingly, an antisense nucleic acid polypeptide can hydrogen bond to a sense nucleic acid polypeptide.

The term "body fluid" refers to fluids that are excreted or secreted from the body as well as fluids that are normally not (e.g. amniotic fluid, aqueous humor, bile, blood and blood plasma, cerebrospinal fluid, cerumen and earwax, cowper's fluid or pre-ejaculatory fluid, chyle, chyme, stool, female ejaculate, interstitial fluid, intracellular fluid, lymph, menses, breast milk, mucus, pleural fluid, peritoneal fluid, pus, saliva, sebum, semen, serum, sweat, synovial fluid, tears, urine, vaginal lubrication, vitreous humor, vomit).

The terms "cancer" or "tumor" or "hyperproliferative disorder" refer to the presence of cells possessing characteristics typical of cancer-causing cells, such as uncontrolled proliferation, immortality, metastatic potential, rapid growth and proliferation rate, and certain characteristic morphological features. Cancer cells are often in the form of a tumor, but such cells may exist alone within an animal, or may be a non-tumorigenic cancer cell, such as a leukemia cell. Cancers include, but are not limited to, B cell cancer, e.g., multiple myeloma, Waldenström's macroglobulinemia, the heavy chain diseases, such as, for example, alpha chain disease, gamma chain disease, and mu chain disease, benign monoclonal gammopathy, and immunocytic amyloidosis, melanomas, breast cancer, lung cancer, bronchus cancer, colorectal cancer, prostate cancer (e.g., metastatic, hormone refractory prostate cancer), pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematological tissues, and the like. Other non-limiting examples of types of cancers applicable to the methods encompassed by the present invention include human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, pancreatic cancer, breast cancer, ovarian cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, liver cancer, choriocarcinoma, seminoma, embryonal carcinoma, Wilms' tumor, cervical cancer, bone cancer, brain tumor, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease. In some embodiments, the cancer whose phenotype is determined by the method of the invention is an epithelial cancer such as, but not limited to, bladder cancer, breast cancer, cervical cancer, colon cancer, gynecologic cancers, renal cancer, laryngeal cancer, lung cancer, oral cancer, head and neck cancer, ovarian cancer, pancreatic cancer, prostate cancer, or skin cancer. In other embodiments, the cancer is breast cancer, prostrate cancer, lung cancer, or colon cancer. In still other embodiments, the epithelial cancer is non-small-cell lung cancer, nonpapillary renal cell carcinoma, cervical carcinoma, ovarian carcinoma (e.g., serous ovarian carcinoma), or breast carcinoma. The epithelial cancers may be characterized in various other ways including, but not limited to, serous, endometrioid, mucinous, clear cell, brenner, or undifferentiated. In some embodiments, the present invention is used in the treatment, diagnosis, and/or prognosis of lymphoma or its subtypes, including, but not limited to, mantle cell lymphoma.

The terms "CDR", and its plural "CDRs", refer to a complementarity determining region (CDR) of which three make up the binding character of a light chain variable region (CDR-L1, CDR-L2 and CDR-L3) and three make up the binding character of a heavy chain variable region (CDR-H1, CDR-H2 and CDR-H3). CDRs contribute to the functional activity of an antibody molecule and are separated by amino acid sequences that comprise scaffolding or framework regions. The exact definitional CDR boundaries and lengths are subject to different classification and numbering systems. CDRs may therefore be referred to by Kabat, Chothia, contact or any other boundary definitions. Despite differing boundaries, each of these systems has some degree of overlap in what constitutes the so called "hypervariable regions" within the variable sequences. CDR definitions according to these systems may therefore differ in length and boundary areas with respect to the adjacent framework region. In some embodiments, the CDRs described herein are determined according to listed segments of light chain and heavy chain variable region nucleic acid and polypeptide sequences (see, for example Table 3). See also Kabat, Chothia, and/or MacCallum et al., (Kabat et al., in "Sequences of Proteins of Immunological Interest," $5^{th}$ Edition, U.S. Department of Health and Human Services, 1992; Chothia et al. (1987) J. Mol. Biol. 196, 901; and MacCallum et al., J. Mol. Biol. (1996) 262, 732, each of which is incorporated by reference in its entirety).

The term "coding region" refers to regions of a nucleotide sequence comprising codons which are translated into amino acid residues, whereas the term "noncoding region" refers to regions of a nucleotide sequence that are not translated into amino acids (e.g., 5' and 3' untranslated regions).

The term "complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

As used herein, the term "composite antibody" refers to an antibody which has variable regions comprising germline or non-germline immunoglobulin sequences from two or more unrelated variable regions. Additionally, the term "composite, human antibody" refers to an antibody which has constant regions derived from human germline or non-germline immunoglobulin sequences and variable regions comprising human germline or non-germline sequences from two or more unrelated human variable regions. A composite, human antibody is useful as an effective component in a therapeutic agent according to the present invention since the antigenicity of the composite, human antibody in the human body is lowered.

The term "costimulate," as used with reference to activated immune cells, includes the ability of a costimulatory polypeptide to provide a second, non-activating receptor mediated signal (a "costimulatory signal") that induces proliferation or effector function. For example, a costimulatory signal can result in cytokine secretion. e.g., in a T cell that has received a T cell-receptor-mediated signal. Immune cells that have received a cell-receptor mediated signal, e.g., via an activating receptor are referred to herein as "activated immune cells."

The term "costimulatory receptor" includes receptors which transmit a costimulatory signal to a immune cell, e.g., CD28. As used herein, the term "inhibitory receptors" includes receptors which transmit a negative signal to an immune cell (e.g., CTLA4 or PD-1). An inhibitory signal as transduced by an inhibitory receptor can occur even if a costimulatory receptor (such as CD28) is not present on the immune cell and, thus, is not simply a function of competition between inhibitory receptors and costimulatory receptors for binding of costimulatory polypeptides (Fallarino et al. (1998) *J. Exp. Med.* 188:205). Transmission of an inhibitory signal to an immune cell can result in unresponsiveness or anergy or programmed cell death in the immune cell. Preferably transmission of an inhibitory signal operates through a mechanism that does not involve apoptosis. As used herein the term "apoptosis" includes programmed cell death which can be characterized using techniques which are known in the art. Apoptotic cell death can be characterized, e.g., by cell shrinkage, membrane blebbing and chromatin condensation culminating in cell fragmentation. Cells undergoing apoptosis also display a characteristic pattern of internucleosomal DNA cleavage. Depending upon the form of the polypeptide that binds to a receptor, a signal can either be transmitted (e.g., by a multivalent form of PD-L2 polypeptide or a form of PD-L2 that binds to Fc receptors that results in crosslinking of receptor) or a signal can be inhibited (e.g., by a soluble, monovalent form of a PD-L2 or a form of PD-L2 lacking Fc receptors), for instance by competing with activating forms of PD-L2 for binding to the receptor. However, there are instances in which a soluble polypeptide can be stimulatory. The effects of a modulatory agent can be easily demonstrated using routine screening assays as described herein.

As used herein, the term "Fc region" is used to define a C-terminal region of an immunoglobulin heavy chain, including native-sequence Fe regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. Suitable native-sequence Fc regions for use in the antibodies of the present invention include human IgG1, IgG2 (IgG2A, IgG2B). IgG3 and IgG4.

As used herein, "Fe receptor" or "FcR" describes a receptor that binds to the Fe region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors, FcγRII receptors include FcγRIIA (an "activating receptor") and FcγRIIB (an "inhibiting receptor"), which have similar amino acid sequences that differ primarily in the cytoplasmic domains thereof. Activating receptor FcγRIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (see M. Daëron, *Annu. Rev. Immu-*

*nol.* 15:203-234 (1997). FcRs are reviewed in Ravetch and Kinet, *Annu. Rev. Immunol.* 9: 457-92 (1991); Capel et al., *Immunomethods* 4: 25-34 (1994); and de Haas et al., *J. Lab. Clin. Med.* 126: 330-41 (1995). Other FcRs, including those to be identified in the future, are encompassed by the term "FcR" herein.

A molecule is "fixed" or "affixed" to a substrate if it is covalently or non-covalently associated with the substrate such the substrate can be rinsed with a fluid (e.g. standard saline citrate, pH 7.4) without a substantial fraction of the molecule dissociating from the substrate.

"Function-conservative variants" are those in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Amino acids other than those indicated as conserved may differ in a protein so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. A "function-conservative variant" also includes a polypeptide which has at least 60% amino acid identity as determined by BLAST or FASTA algorithms, preferably at least 75%, more preferably at least 85%, still preferably at least 90%, and even more preferably at least 95%, and which has the same or substantially similar properties or functions as the native or parent protein to which it is compared.

As used herein, the term "heterologous antibody" is defined in relation to the transgenic non-human organism producing such an antibody. This term refers to an antibody having an amino acid sequence or an encoding nucleic acid sequence corresponding to that found in an organism not consisting of the transgenic non-human animal, and generally from a species other than that of the transgenic non-human animal.

The term "homologous" as used herein, refers to nucleotide sequence similarity between two regions of the same nucleic acid strand or between regions of two different nucleic acid strands. When a nucleotide residue position in both regions is occupied by the same nucleotide residue, then the regions are homologous at that position. A first region is homologous to a second region if at least one nucleotide residue position of each region is occupied by the same residue. Homology between two regions is expressed in terms of the proportion of nucleotide residue positions of the two regions that are occupied by the same nucleotide residue. By way of example, a region having the nucleotide sequence 5'-ATTGCC-3' and a region having the nucleotide sequence 5'-TATGGC-3' share 50% homology. Preferably, the first region comprises a first portion and the second region comprises a second portion, whereby, at least about 50%, and preferably at least about 75%, at least about 90%, or at least about 95% of the nucleotide residue positions of each of the portions are occupied by the same nucleotide residue. More preferably, all nucleotide residue positions of each of the portions are occupied by the same nucleotide residue.

The term "host cell" is intended to refer to a cell into which a nucleic acid of the invention, such as a recombinant expression vector of the invention, has been introduced. The terms "host cell" and "recombinant host cell" are used interchangeably herein. It should be understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

The term "humanized antibody", as used herein, is intended to include antibodies made by a non-human cell having variable and constant regions which have been altered to more closely resemble antibodies that would be made by a human cell. For example, by altering the non-human antibody amino acid sequence to incorporate amino acids found in human germline immunoglobulin sequences. The humanized antibodies of the present invention may include amino acid residues not encoded by human germline immunoglobulin sequences (e.g., mutations introduced by random or site-specific mutagenesis in vitro or by somatic mutation in vivo), for example in the CDRs. The term "humanized antibody", as used herein, also includes antibodies in which CDR sequences derived from the germline of another mammalian species, such as a mouse, have been grafted onto human framework sequences.

As used herein, the term "hypervariable region," "HVR," or "HV," refers to the regions of an antibody-variable domain that are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al. (2000) Immunity 13, 37-45; Johnson and Wu in Methods in Molecular Biology 248, 1-25 (Lo, ed., Human Press, Totowa, N.J., 2003)). Indeed, naturally occurring camelid antibodies consisting of a heavy chain only are functional and stable in the absence of light chain (see, e.g., Hamers-Casterman et al. (1993) Nature 363:446-448 (1993) and Sheriff et al. (1996) Nature Struct. Biol. 3, 733-736). The term "immune cell" refers to cells that play a role in the immune response. Immune cells are of hematopoietic origin, and include lymphocytes, such as B cells and T cells; natural killer cells; myeloid cells, such as monocytes, macrophages, cosinophils, mast cells, basophils, and granulocytes.

The term "immune response" includes T cell mediated and/or B cell mediated immune responses that are influenced by modulation of T cell costimulation. Exemplary immune responses include T cell responses, e.g., cytokine production, and cellular cytotoxicity. In addition, the term immune response includes immune responses that are indirectly effected by T cell activation, e.g., antibody production (humoral responses) and activation of cytokine responsive cells, e.g., macrophages.

The term "inhibit" includes the decrease, limitation, or blockage, of, for example a particular action, function, or interaction. For example, cancer is "inhibited" if at least one symptom of the cancer, such as hyperproliferative growth, is alleviated, terminated, slowed, or prevented. As used herein, cancer is also "inhibited" if recurrence or metastasis of the cancer is reduced, slowed, delayed, or prevented.

The term "inhibitory signal" refers to a signal transmitted via an inhibitory receptor (e.g., CTLA4 or PD-1) for a polypeptide on a immune cell. Such a signal antagonizes a signal via an activating receptor (e.g., via a TCR, CD3, BCR, or Fc polypeptide) and can result in, e.g., inhibition of second messenger generation; an inhibition of proliferation; an inhibition of effector function in the immune cell, e.g., reduced phagocytosis, reduced antibody production, reduced cellular cytotoxicity, the failure of the immune cell to produce mediators, (such as cytokines (e.g., IL-2) and/or mediators of allergic responses); or the development of anergy.

The term “interaction,” when referring to an interaction between two molecules, refers to the physical contact (e.g., binding) of the molecules with one another. Generally, such an interaction results in an activity (which produces a biological effect) of one or both of said molecules. The activity may be a direct activity of one or both of the molecules, (e.g., signal transduction). Alternatively, one or both molecules in the interaction may be prevented from binding their ligand, and thus be held inactive with respect to ligand binding activity (e.g., binding its ligand and triggering or inhibiting costimulation). To inhibit such an interaction results in the disruption of the activity of one or more molecules involved in the interaction. To enhance such an interaction is to prolong or increase the likelihood of said physical contact, and prolong or increase the likelihood of said activity.

The term “isolated protein” refers to a protein that is substantially free of other proteins, cellular material, separation medium, and culture medium when isolated from cells or produced by recombinant DNA techniques, or chemical precursors or other chemicals when chemically synthesized. An “isolated” or “purified” protein or biologically active portion thereof is substantially free of cellular material or other contaminating proteins from the cell or tissue source from which the antibody, polypeptide, peptide or fusion protein is derived, or substantially free from chemical precursors or other chemicals when chemically synthesized. The language “substantially free of cellular material” includes preparations of polypeptide, in which the protein is separated from cellular components of the cells from which it is isolated or recombinantly produced. In one embodiment, the language “substantially free of cellular material” includes preparations of protein, having less than about 30% (by dry weight) of non-desired protein (also referred to herein as a “contaminating protein”), more preferably less than about 20% of non-desired protein, still more preferably less than about 10% of non-desired protein, and most preferably less than about 5% non-desired protein. When antibody, polypeptide, peptide or fusion protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The term “isotype” refers to the antibody class (e.g., IgM or IgG1) that is encoded by heavy chain constant region genes.

The term “$K_D$” is intended to refer to the dissociation equilibrium constant of a particular antibody-antigen interaction. The binding affinity of antibodies of the disclosed invention may be measured or determined by standard antibody-antigen assays, for example, competitive assays, saturation assays, or standard immunoassays such as ELISA or RIA.

The term “modulate” includes up-regulation and down-regulation, e.g., enhancing or inhibiting a response.

The term “naturally-occurring” nucleic acid polypeptide refers to an RNA or DNA polypeptide having a nucleotide sequence that occurs in nature (e.g., encodes a natural protein).

The “normal” level of expression of a marker is the level of expression of the marker in cells of a subject, e.g., a human patient, not afflicted with a cancer. An “over-expression” or “significantly higher level of expression” of a marker refers to an expression level in a test sample that is greater than the standard error of the assay employed to assess expression, and is preferably at least twice, and more preferably 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more higher than the expression activity or level of the marker in a control sample (e.g., sample from a healthy subject not having the marker associated disease) and preferably, the average expression level of the marker in several control samples. A “significantly lower level of expression” of a marker refers to an expression level in a test sample that is at least twice, and more preferably 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more lower than the expression level of the marker in a control sample (e.g., sample from a healthy subject not having the marker associated disease) and preferably, the average expression level of the marker in several control samples.

The term “PD-1” refers to a member of the immunoglobulin gene superfamily that functions as a coinhibitory receptor having PD-L1 and PD-L2 as known ligands. PD-1 was previously identified using a subtraction cloning based approach to select for proteins involved in apoptotic cell death. PD-1 is a member of the CD28/CTLA-4 family of molecules based on its ability to bind to PD-L1. Like CTLA4, PD-1 is rapidly induced on the surface off-cells in response to anti-CD3 (Agata et al. 25 (1996) *Int. Immunol.* 8:765). In contrast to CTLA4, however, PD-1 is also induced on the surface of B-cells (in response to anti-IgM). PD-1 is also expressed on a subset of thymocytes and myeloid cells (Agata et al. (1996) supra; Nishimura et al. (1996) *Int. Immunol.* 8:773).

The nucleic acid and amino acid sequences of a representative human PD-1 biomarker is available to the public at the GenBank database under NM_005018.2 and NP_005009.2 and is shown in Table 1 (see also Ishida et al. (1992) 20 *EMBO J* 11:3887; Shinohara et al. (1994) *Genomics* 23:704: U.S. Pat. No. 5,698,520). PD-1 has an extracellular region containing immunoglobulin superfamily domain, a transmembrane domain, and an intracellular region including an immunoreceptor tyrosine-based inhibitory motif (ITIM) (Ishida et al. (1992) *EMBO J.* 11:3887; Shinohara et al. (1994) *Genomics* 23:704; U.S. Pat. No. 5,698,520). These features also define a larger family of polypeptides, called the immunoinhibitory receptors, which also includes gp49B, PIR-B, and the killer inhibitory receptors (KIRs) (Vivier and Daeron (1997) *Immunol. Today* 18:286). It is often assumed that the tyrosyl phosphorylated ITIM motif of these receptors interacts with SH2-domain containing phosphatases, which leads to inhibitory signals. A subset of these immunoinhibitory receptors bind to MHC polypeptides, for example the KIRs, and CTLA4 bind to B7-1 and B7-2. It has been proposed that there is a phylogenetic relationship between the MHC and B7 genes (Henry et al. (1999) *Immunol. Today* 20(6):285-8). Nucleic acid and polypeptide sequences of PD-1 orthologs in organisms other than humans are well known and include, for example, mouse PD-1 (NM_008798.2 and NP_032824.1), rat PD-1 (NM_001106927.1 and NP_001100397.1), dog PD-1 (XM_543338.3 and XP_543338.3), cow PD-1 (NM_001083506.1 and NP_001076975.1), and chicken PD-1 (XM_422723.3 and XP_422723.2).

PD-1 polypeptides are inhibitory receptors capable of transmitting an inhibitory signal to an immune cell to thereby inhibit immune cell effector function, or are capable of promoting costimulation (e.g., by competitive inhibition) of immune cells, e.g., when present in soluble, monomeric form. Preferred PD-1 family members share sequence identity with PD-1 and bind to one or more B7 family members, e.g., B7-1, B7-2. PD-1 ligand, and/or other polypeptides on antigen presenting cells.

The term “PD-1 activity,” includes the ability of a PD-1 polypeptide to modulate an inhibitory signal in an activated immune cell, e.g., by engaging a natural PD-1 ligand on an antigen presenting cell. PD-1 transmits an inhibitory signal to an immune cell in a manner similar to CTLA4. Modulation of an inhibitory signal in an immune cell results in modulation of proliferation of, and/or cytokine secretion by, an immune cell. Thus, the term “PD-1 activity” includes the ability of a PD-1 polypeptide to bind its natural ligand(s), the ability to modulate immune cell costimulatory or inhibitory signals, and the ability to modulate the immune response.

The term “PD-1 ligand” refers to binding partners of the PD-1 receptor and includes both PD-L (Freeman et al. (2000) *J. Exp. Med.* 192:1027) and PD-L2 (Latchman et al. (2001) *Nat. Immunol.* 2:261). At least two types of human PD-1 ligand polypeptides exist. PD-1 ligand proteins comprise a signal sequence, and an IgV domain, an IgC domain, a transmembrane domain, and a short cytoplasmic tail. Both PD-L1 (See Freeman et al. (2000) J. Exp. Med. 192:1027 for sequence data) and PD-L2 (See Latchman et al. (2001) Nat. Immunol. 2:261 for sequence data) are members of the B7 family of polypeptides. Both PD-L1 and PD-L2 are expressed in placenta, spleen, lymph nodes, thymus, and heart. Only PD-L2 is expressed in pancreas, lung and liver, while only PD-L1 is expressed in fetal liver. Both PD-1 ligands are upregulated on activated monocytes and dendritic cells.

PD-1 ligands comprise a family of polypeptides having certain conserved structural and functional features. The term “family” when used to refer to proteins or nucleic acid molecules, is intended to mean two or more proteins or nucleic acid molecules having a common structural domain or motif and having sufficient amino acid or nucleotide sequence homology, as defined herein. Such family members can be naturally or non-naturally occurring and can be from either the same or different species. For example, a family can contain a first protein of human origin, as well as other, distinct proteins of human origin or alternatively, can contain homologues of non-human origin. Members of a family may also have common functional characteristics. PD-1 ligands are members of the B7 family of polypeptides. The term “B7 family” or “B7 polypeptides” as used herein includes costimulatory polypeptides that share sequence homology with B7 polypeptides, e.g., with B7-1, B7-2, B7h (Swallow et al. (1999) *Immunity* 11:423), and/or PD-1 ligands (e.g., PD-L1 or PD-L2). For example, human B7-1 and B7-2 share approximately 26% amino acid sequence identity when compared using the BLAST program at NCBI with the default parameters (Blosum62 matrix with gap penalties set at existence 11 and extension 1 (See the NCBI website). The term B7 family also includes variants of these polypeptides which are capable of modulating immune cell function. The B7 family of molecules share a number of conserved regions, including signal domains. IgV domains and the IgC domains. IgV domains and the IgC domains are art-recognized Ig superfamily member domains. These domains correspond to structural units that have distinct folding patterns called Ig folds. Ig folds are comprised of a sandwich of two β sheets, each consisting of anti-parallel β strands of 5-10 amino acids with a conserved disulfide bond between the two sheets in most, but not all, IgC domains of Ig, TCR, and MHC molecules share the same types of sequence patterns and are called the C1-set within the Ig superfamily. Other IgC domains fall within other sets. IgV domains also share sequence patterns and are called V set domains. IgV domains are longer than IgC domains and form an additional pair of β strands.

Preferred B7 polypeptides are capable of providing costimulatory or inhibitory signals to immune cells to thereby promote or inhibit immune cell responses. For example, B7 family members that bind to costimulatory receptors increase T cell activation and proliferation, while B7 family members that bind to inhibitory receptors reduce costimulation. Moreover, the same B7 family member may increase or decrease T cell costimulation. For example, when bound to a costimulatory receptor, PD-1 ligand can induce costimulation of immune cells or can inhibit immune cell costimulation, e.g., when present in soluble form. When bound to an inhibitory receptor, PD-1 ligand polypeptides can transmit an inhibitory signal to an immune cell. Preferred B7 family members include B7-1, B7-2, B7h, PD-L1 or PD-L2 and soluble fragments or derivatives thereof. In one embodiment, B7 family members bind to one or more receptors on an immune cell, e.g., CTLA4, CD28. ICOS, PD-1 and/or other receptors, and, depending on the receptor, have the ability to transmit an inhibitory signal or a costimulatory signal to an immune cell, preferably a T cell.

Modulation of a costimulatory signal results in modulation of effector function of an immune cell. Thus, the term “PD-1 ligand activity” includes the ability of a PD-1 ligand polypeptide to bind its natural receptor(s) (e.g. PD-1 or B7-1), the ability to modulate immune cell costimulatory or inhibitory signals, and the ability to modulate the immune response.

The term “PD-L1” refers to a specific PD-1 ligand. Two forms of human PD-L1 molecules have been identified. One form is a naturally occurring PD-L1 soluble polypeptide, i.e., having a short hydrophilic domain and no transmembrane domain, and is referred to herein as PD-L1S (shown in Table 1 as SEQ ID NO: 4). The second form is a cell-associated polypeptide, i.e., having a transmembrane and cytoplasmic domain, referred to herein as PD-L1M (shown in SEQ ID NO: 6). The nucleic acid and amino acid sequences of representative human PD-L1 biomarkers regarding PD-L1M are also available to the public at the GenBank database under NM_014143.3 and NP_054862.1. PD-L1 proteins comprise a signal sequence, and an IgV domain and an IgC domain. The signal sequence of SEQ ID NO: 4 is shown from about amino acid 1 to about amino acid 18. The signal sequence of SEQ ID NO: 6 is shown: from about amino acid 1 to about amino acid 18. The IgV domain of SEQ ID NO: 4 is shown from about amino acid 19 to about amino acid 134 and the IgV domain of SEQ ID NO: 6 is shown from about amino acid 19 to about amino acid 134. The IgC domain of SEQ ID NO: 4 is shown from about amino acid 135 to about amino acid 227 and the IgC domain of SEQ ID NO: 6 is shown from about amino acid 135 to about amino acid 227. The hydrophilic tail of the PD-L1 exemplified in SEQ ID NO: 4 comprises a hydrophilic tail shown from about amino acid 228 to about amino acid 245. The PD-L1 polypeptide exemplified in SEQ ID NO: 6 comprises a transmembrane domain shown from about amino acids 239 to about amino acid 259 of SEQ ID NO: 6 and a cytoplasmic domain shown from about 30 amino acid 260 to about amino acid 290 of SEQ ID NO: 6. In addition, nucleic acid and polypeptide sequences of PD-L1 orthologs in organisms other than humans are well known and include, for example, mouse PD-L1 (NM_021893.3 and NP_068693.1), rat PD-L1 (NM_001191954.1 and NP_001178883.1), dog PD-L1 (XM_541302.3 and XP_541302.3), cow PD-L1 (NM_001163412.1 and NP_001156884.1), and chicken PD-L1 (XM_424811.3 and XP_424811.3).

The term "PD-L2" refers to another specific PD-1 ligand. PD-L2 is a B7 family member expressed on various APCs, including dendritic cells, macrophages and bone-marrow derived mast cells (Zhong et al. (2007) Eur. J. Immunol. 37:2405). APC-expressed PD-L2 is able to both inhibit T cell activation through ligation of PD-1 and costimulate T cell activation, through a PD-1 independent mechanism (Shin et al. (2005) J. Exp. Med. 201:1531). In addition, ligation of dendritic cell-expressed PD-L2 results in enhanced dendritic cell cytokine expression and survival (Radhakrishnan et al. (2003) J. Immunol. 37:1827; Nguyen et al. (2002) J. Exp. Med. 196:1393). The nucleic acid and amino acid sequences of representative human PD-L2 biomarkers (e.g., SEQ ID NOs: 7 and 8) are well known in the art and are also available to the public at the GenBank database under NM_025239.3 and NP_079515.2. PD-L2 proteins are characterized by common structural elements. In some embodiments, PD-L2 proteins include at least one or more of the following domains: a signal peptide domain, a transmembrane domain, an IgV domain, an IgC domain, an extracellular domain, a transmembrane domain, and a cytoplasmic domain. For example, amino acids 1-19 of SEQ ID NO: 8 comprises a signal sequence. As used herein, a "signal sequence" or "signal peptide" serves to direct a polypeptide containing such a sequence to a lipid bilayer, and is cleaved in secreted and membrane bound polypeptides and includes a peptide containing about 15 or more amino acids which occurs at the N-terminus of secretory and membrane bound polypeptides and which contains a large number of hydrophobic amino acid residues. For example, a signal sequence contains at least about 10-30 amino acid residues, preferably about 15-25 amino acid residues, more preferably about 18-20 amino acid residues, and even more preferably about 19 amino acid residues, and has at least about 35-65%, preferably about 38-50%, and more preferably about 40-45% hydrophobic amino acid residues (e.g., valine, leucine, isoleucine or phenylalanine). In another embodiment, amino acid residues 220-243 of the native human PD-L2 polypeptide and amino acid residues 201-243 of the mature polypeptide comprise a transmembrane domain. As used herein, the term "transmembrane domain" includes an amino acid sequence of about 15 amino acid residues in length which spans the plasma membrane. More preferably, a transmembrane domain includes about at least 20, 25, 30, 35, 40, or 45 amino acid residues and spans the plasma membrane. Transmembrane domains are rich in hydrophobic residues, and typically have an alpha-helical structure. In a preferred embodiment, at least 50%, 60%, 70%, 80%, 90%, 95% or more of the amino acids of a transmembrane domain are hydrophobic, e.g., leucines, isoleucines, tyrosines, or tryptophans. Transmembrane domains are described in, for example, Zagotta, W. N. et al. (1996) Annu. Rev. Neurosci. 19: 235-263. In still another embodiment, amino acid residues 20-120 of the native human PD-L2 polypeptide and amino acid residues 1-101 of the mature polypeptide comprise an IgV domain. Amino acid residues 121-219 of the native human PD-L2 polypeptide and amino acid residues 102-200 of the mature polypeptide comprise an IgC domain. As used herein, IgV and IgC domains are recognized in the art as Ig superfamily member domains. These domains correspond to structural units that have distinct folding patterns called Ig folds. Ig folds are comprised of a sandwich of two β sheets, each consisting of antiparallel (3 strands of 5-10 amino acids with a conserved disulfide bond between the two sheets in most, but not all, domains. IgC domains of Ig, TCR, and MHC molecules share the same types of sequence patterns and are called the C1 set within the Ig superfamily. Other IgC domains fall within other sets. IgV domains also share sequence patterns and are called V set domains. IgV domains are longer than C-domains and form an additional pair of strands. In yet another embodiment, amino acid residues 1-219 of the native human PD-L2 polypeptide and amino acid residues 1-200 of the mature polypeptide comprise an extracellular domain. As used herein, the term "extracellular domain" represents the N-terminal amino acids which extend as a tail from the surface of a cell. An extracellular domain of the present invention includes an IgV domain and an IgC domain, and may include a signal peptide domain. In still another embodiment, amino acid residues 244-273 of the native human PD-L2 polypeptide and amino acid residues 225-273 of the mature polypeptide comprise a cytoplasmic domain. As used herein, the term "cytoplasmic domain" represents the C-terminal amino acids which extend as a tail into the cytoplasm of a cell. In addition, nucleic acid and polypeptide sequences of PD-L2 orthologs in organisms other than humans are well known and include, for example, mouse PD-L2 (NM_021396.2 and NP_067371.1), rat PD-L2 (NM_001107582.2 and NP_001101052.2), dog PD-L2 (XM_847012.2 and XP_852105.2), cow PD-L2 (XM_586846.5 and XP_586846.3), and chimpanzee PD-L2 (XM_001140776.2 and XP_001140776.1).

The term "PD-L2 activity," "biological activity of PD-L2," or "functional activity of PD-L2," refers to an activity exerted by a PD-L2 protein, polypeptide or nucleic acid molecule on a PD-L2-responsive cell or tissue, or on a PD-L2 polypeptide binding partner, as determined in vivo, or in vitro, according to standard techniques. In one embodiment, a PD-L2 activity is a direct activity, such as an association with a PD-L2 binding partner. As used herein, a "target molecule" or "binding partner" is a molecule with which a PD-L2 polypeptide binds or interacts in nature, such that PD-L2-mediated function is achieved. In an exemplary embodiment, a PD-L2 target molecule is the receptor RGMb. Alternatively, a PD-L2 activity is an indirect activity, such as a cellular signaling activity mediated by interaction of the PD-L2 polypeptide with its natural binding partner, e.g., RGMb. The biological activities of PD-L2 are described herein. For example, the PD-L2 polypeptides of the present invention can have one or more of the following activities: 1) bind to and/or modulate the activity of the receptor RGMb, PD-1, or other PD-L2 natural binding partners, 2) modulate intra- or intercellular signaling, 3) modulate activation of immune cells, e.g., T lymphocytes, and 4) modulate the immune response of an organism, e.g., a mouse or human organism.

The term "peripheral blood cell subtypes" refers to cell types normally found in the peripheral blood including, but is not limited to, eosinophils, neutrophils, T cells, monocytes, NK cells, granulocytes, and B cells.

The term "recombinant human antibody" includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable and constant regions derived from human germline and/or non-germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

The term "RGMb" refers to a glycosylphophatidylinositol (GPI)-anchored member of the repulsive guidance molecule family. Samad et al. in JBC Papers 2005, Vol. 280, 14122-14129 describe the interaction between RGMb and the Type I and Type II receptors of bone morphogenetic protein (BMP). However, the interaction between RGMb and PD-L2 was not previously known. The nucleic acid and amino acid sequences of representative human RGMb biomarkers (e.g., SEQ ID NOs: 9 and 10) are well known in the art and are also available to the public at the GenBank database under NM_025239.3 and NP_079515.2. RGMb proteins are characterized by common structural elements. In some embodiments, RGMb proteins comprise conserved domains with homology to notch-3, phosphatidylinositol-4-phosphate-5-kinase type II beta, insulin-like growth factor binding protein-2, thrombospondin, ephrin type-B receptor 3 precursor, and Slit-2, all of which are known to influence axonal guidance, neurite outgrowth, and other neuronal developmental functions. The C-terminus of RGMb also contains a hydrophobic domain indicative of a 21 amino acid extracellular GPI anchoring. In addition, nucleic acid and polypeptide sequences of RGMb orthologs in organisms other than humans are well known and include, for example, mouse RGMb (NM_178615.3 and NP_848730.2), chimpanzee RGMb (XM_517848.3 and XP_517848.2), cow RGMb (XM_002689413.1 and XP_002689459.1), chicken RGMb (XM_42860.3 and XP_424860.3), and zebrafish RGMb (NM_001001727.1 and NP_001001727.1).

The term "sample" used for detecting or determining the presence or level of at least one biomarker is typically whole blood, plasma, serum, saliva, urine, stool (e.g., feces), tears, and any other bodily fluid (e.g., as described above under the definition of "body fluids"), or a tissue sample (e.g., biopsy) such as a small intestine, colon sample, or surgical resection tissue. In certain instances, the method of the present invention further comprises obtaining the sample from the individual prior to detecting or determining the presence or level of at least one marker in the sample.

The term "small molecule" is a term of the art and includes molecules that are less than about 1000 molecular weight or less than about 500 molecular weight. In one embodiment, small molecules do not exclusively comprise peptide bonds. In another embodiment, small molecules are not oligomeric. Exemplary small molecule compounds which can be screened for activity include, but are not limited to, peptides, peptidomimetics, nucleic acids, carbohydrates, small organic molecules (e.g., polyketides) (Cane et al. 1998. Science 282:63), and natural product extract libraries. In another embodiment, the compounds are small, organic non-peptidic compounds. In a further embodiment, a small molecule is not biosynthetic.

The term "specific binding" refers to antibody binding to a predetermined antigen. Typically, the antibody binds with an affinity ($K_D$) of approximately less than $10^{-7}$ M, such as approximately less than $10^{-8}$ M, $10^{-9}$ M or $10^{-10}$ M or even lower when determined by surface plasmon resonance (SPR) technology in a BIACORE® assay instrument using human GaII as the analyte and the antibody as the ligand, and binds to the predetermined antigen with an affinity that is at least 1.1-, 1.2-, 1.3-, 1.4-, 1.5-, 1.6-, 1.7-, 1.8-, 1.9-, 2.0-, 2.5-, 3.0-, 3.5-, 4.0-, 4.5-, 5.0-, 6.0-, 7.0-, 8.0-, 9.0-, or 10.0-fold or greater than its affinity for binding to a non-specific antigen (e.g., BSA, casein) other than the predetermined antigen or a closely-related antigen. The phrases "an antibody recognizing an antigen" and "an antibody specific for an antigen" are used interchangeably herein with the term "an antibody which binds specifically to an antigen."

The term "subject" refers to any healthy animal, mammal or human, or any animal, mammal or human afflicted with a condition of interest (e.g., cancer). The term "subject" is interchangeable with "patient."

The term "substantially free of chemical precursors or other chemicals" includes preparations of antibody, polypeptide, peptide or fusion protein in which the protein is separated from chemical precursors or other chemicals which are involved in the synthesis of the protein. In one embodiment, the language "substantially free of chemical precursors or other chemicals" includes preparations of antibody, polypeptide, peptide or fusion protein having less than about 30% (by dry weight) of chemical precursors or non-antibody, polypeptide, peptide or fusion protein chemicals, more preferably less than about 20% chemical precursors or non-antibody, polypeptide, peptide or fusion protein chemicals, still more preferably less than about 10% chemical precursors or non-antibody, polypeptide, peptide or fusion protein chemicals, and most preferably less than about 5% chemical precursors or non-antibody, polypeptide, peptide or fusion protein chemicals.

A "transcribed polynucleotide" or "nucleotide transcript" is a polynucleotide (e.g. an mRNA, hnRNA, cDNA, mature miRNA, pre-miRNA, pri-miRNA, miRNA*, anti-miRNA, or a miRNA binding site, or a variant thereof or an analog of such RNA or cDNA) which is complementary to or homologous with all or a portion of a mature mRNA made by transcription of a marker of the invention and normal post-transcriptional processing (e.g. splicing), if any, of the RNA transcript, and reverse transcription of the RNA transcript.

The term "T cell" includes $CD4^+$ T cells and $CD8^+$ T cells. The term T cell also includes both T helper 1 type T cells and T helper 2 type T cells. The term "antigen presenting cell" includes professional antigen presenting cells (e.g., B lymphocytes, monocytes, dendritic cells, Langerhans cells), as well as other antigen presenting cells (e.g., keratinocytes, endothelial cells, astrocytes, fibroblasts, oligodendrocytes).

An "underexpression" or "significantly lower level of expression or copy number" of a marker (e.g., RGMb, PD-L2, or downstream signaling marker thereof) refers to an expression level or copy number in a test sample that is greater than the standard error of the assay employed to assess expression or copy number, but is preferably at least twice, and more preferably three, four, five or ten or more times less than the expression level or copy number of the marker in a control sample (e.g., sample from a healthy subject not afflicted with cancer) and preferably, the average expression level or copy number of the marker in several control samples.

The term "vector" refers to a nucleic acid capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" or simply "expression vectors". In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "tolerance" or "unresponsiveness" includes refractivity of cells, such as immune cells, to stimulation, e.g., stimulation via an activating receptor or a cytokine. Unresponsiveness can occur, e.g., because of exposure to immunosuppressants or exposure to high doses of antigen. Several independent methods can induce tolerance. One mechanism is referred to as "anergy," which is defined as a state where cells persist in vivo as unresponsive cells rather than differentiating into cells having effector functions. Such refractivity is generally antigen-specific and persists after exposure to the tolerizing antigen has ceased. For example, anergy in T cells is characterized by lack of cytokine production, e.g., IL-2. T cell anergy occurs when T cells are exposed to antigen and receive a first signal (a T cell receptor or CD-3 mediated signal) in the absence of a second signal (a costimulatory signal). Under these conditions, reexposure of the cells to the same antigen (even if reexposure occurs in the presence of a costimulatory polypeptide) results in failure to produce cytokines and, thus, failure to proliferate. Anergic T cells can, however, proliferate if cultured with cytokines (e.g., IL-2). For example, T cell anergy can also be observed by the lack of IL-2 production by T lymphocytes as measured by ELISA or by a proliferation assay using an indicator cell line. Alternatively, a reporter gene construct can be used. For example, anergic T cells fail to initiate IL-2 gene transcription induced by a heterologous promoter under the control of the 5' IL-2 gene enhancer or by a multimer of the API sequence that can be found within the enhancer (Kang et al. (1992) *Science* 257:1134). Another mechanism is referred to as "exhaustion." T cell exhaustion is a state of T cell dysfunction that arises during many chronic infections and cancer. It is defined by poor effector function, sustained expression of inhibitory receptors and a transcriptional state distinct from that of functional effector or memory T cells.

There is a known and definite correspondence between the amino acid sequence of a particular protein and the nucleotide sequences that can code for the protein, as defined by the genetic code (shown below). Likewise, there is a known and definite correspondence between the nucleotide sequence of a particular nucleic acid and the amino acid sequence encoded by that nucleic acid, as defined by the genetic code.

| GENETIC CODE | |
|---|---|
| Alanine (Ala, A) | GCA, GCC, GCG, GCT |
| Arginine (Arg, R) | AGA, ACG, CGA, CGC, CGG, CGT |
| Asparagine (Asn, N) | AAC, AAT |
| Aspartic acid (Asp, D) | GAC, GAT |
| Cysteine (Cys, C) | TGC, TGT |
| Glutamic acid (Glu, E) | GAA, GAG |
| Glutamine (Gln, Q) | CAA, CAG |
| Glycine (Gly, G) | GGA, GGC, GGG, GGT |
| Histidine (His, H) | CAC, CAT |
| Isoleucine (Ile, I) | ATA, ATC, ATT |
| Leucine (Leu, L) | CTA, CTC, CTG, CTT, TTA, TTG |
| Lysine (Lys, K) | AAA, AAG |
| Methionine (Met, M) | ATG |
| Phenylalanine (Phe, F) | TTC, TTT |
| Proline (Pro, P) | CCA, CCC, CCG, CCT |
| Serine (Ser, S) | AGC, AGT, TCA, TCC, TCG, TCT |
| Threonine (Thr, T) | ACA, ACC, ACG, ACT |
| Tryptophan (Trp, W) | TGG |
| Tyrosine (Tyr, Y) | TAC, TAT |
| Valine (Val, V) | GTA, GTC, GTG, GTT |
| Termination signal (end) | TAA, TAG, TGA |

An important and well known feature of the genetic code is its redundancy, whereby, for most of the amino acids used to make proteins, more than one coding nucleotide triplet may be employed (illustrated above). Therefore, a number of different nucleotide sequences may code for a given amino acid sequence. Such nucleotide sequences are considered functionally equivalent since they result in the production of the same amino acid sequence in all organisms (although certain organisms may translate some sequences more efficiently than they do others). Moreover, occasionally, a methylated variant of a purine or pyrimidine may be found in a given nucleotide sequence. Such methylations do not affect the coding relationship between the trinucleotide codon and the corresponding amino acid.

In view of the foregoing, the nucleotide sequence of a DNA or RNA coding for a fusion protein or polypeptide of the invention (or any portion thereof) can be used to derive the fusion protein or polypeptide amino acid sequence, using the genetic code to translate the DNA or RNA into an amino acid sequence. Likewise, for a fusion protein or polypeptide amino acid sequence, corresponding nucleotide sequences that can encode the fusion protein or polypeptide can be deduced from the genetic code (which, because of its redundancy, will produce multiple nucleic acid sequences for any given amino acid sequence). Thus, description and/or disclosure herein of a nucleotide sequence which encodes a fusion protein or polypeptide should be considered to also include description and/or disclosure of the amino acid sequence encoded by the nucleotide sequence. Similarly, description and/or disclosure of a fusion protein or polypeptide amino acid sequence herein should be considered to also include description and/or disclosure of all possible nucleotide sequences that can encode the amino acid sequence.

Finally, nucleic acid and amino acid sequence information for nucleic acid and polypeptide molecules useful in the present invention are well known in the art and readily available on publicly available databases, such as the National Center for Biotechnology Information (NCBI). For example, exemplary nucleic acid and amino acid sequences derived from publicly available sequence databases are provided in Table 1 below.

TABLE 1

SEQ ID NO: 1 Human PD-1 cDNA Sequence

```
cactctggtg gggctgctcc aggc atg cag atc cca cag gcg ccc tgg cca      51
                           Met Gln Ile Pro Gln Ala Pro Trp Pro
                            1               5

gtc gtc tgg gcg gtg cta caa ctg ggc tgg cgg cca gga tgg ttc tta      99
Val Val Trp Ala Val Leu Gln Leu Gly Trp Arg Pro Gly Trp Phe Leu
 10                  15                  20                  25

gac tcc cca gac agg ccc tgg aac ccc ccc acc ttc tcc cca gcc ctg     147
Asp Ser Pro Asp Arg Pro Trp Asn Pro Pro Thr Phe Ser Pro Ala Leu
                 30                  35                  40

ctc gtg gtg acc gaa ggg gac aac gcc acc ttc acc tgc agc ttc tcc     195
Leu Val Val Thr Glu Gly Asp Asn Ala Thr Phe Thr Cys Ser Phe Ser
             45                  50                  55

aac aca tcg gag agc ttc gtg cta aac tgg tac cgc atg agc ccc agc     243
Asn Thr Ser Glu Ser Phe Val Leu Asn Trp Tyr Arg Met Ser Pro Ser
         60                  65                  70

aac cag acg gac aag ctg gcc gcc ttc ccc gag gac cgc agc cag ccc     291
Asn Gln Thr Asp Lys Leu Ala Ala Phe Pro Glu Asp Arg Ser Gln Pro
     75                  80                  85

ggc cag gac tgc cgc ttc cgt gtc aca caa ctg ccc aac ggg cat gac     339
Gly Gln Asp Cys Arg Phe Arg Val Thr Gln Leu Pro Asn Gly Arg Asp
 90                  95                 100                 105

ttc cac atg agc gtg gtc agg gcc cgg cgc aat gac agc ggc acc tac     387
Phe His Met Ser Val Val Arg Ala Arg Arg Asn Asp Ser Gly Thr Tyr
                110                 115                 120

ctc tgt ggg gcc atc tcc ctg gcc ccc aag gcg cag atc aaa gag agc     435
Leu Cys Gly Ala Ile Ser Leu Ala Pro Lys Ala Gln Ile Lys Glu Ser
            125                 130                 135

ctg cgg gca gag ctc agg gtg aca gag aga agg gca gaa gtg ccc aca     483
Leu Arg Ala Glu Leu Arg Val Thr Glu Arg Arg Ala Glu Val Pro Thr
        140                 145                 150

gcc cac ccc agc ccc tca ccc agg tca gcc ggc cag ttc caa acc ctg     531
Ala His Pro Ser Pro Ser Pro Arg Ser Ala Gly Gln Phe Gln Thr Leu
    155                 160                 165

gtg gtt ggt gtc gtg ggc ggc ctg ctg ggc agc ctg gtg ctg cta gtc     579
Val Val Gly Val Val Gly Gly Leu Leu Gly Ser Leu Val Leu Leu Val
170                 175                 180                 185

tgg gtc ctg gcc gtc atc tgc tcc cgg gcc gca cga ggg aca ata gga     627
Trp Val Leu Ala Val Ile Cys Ser Arg Ala Ala Arg Gly Thr Ile Gly
                190                 195                 200

gcc agg cgc acc ggc cag ccc ctg aag gag gac ccc tca gcc gtg cct     675
Ala Arg Arg Thr Gly Gln Pro Leu Lys Glu Asp Pro Ser Ala Val Pro
            205                 210                 215

gtg ttc tct gtg gac tat ggg gag ctg gat ttc cag tgg cga gag aag     723
Val Phe Ser Val Asp Tyr Gly Glu Leu Asp Phe Gln Trp Arg Glu Lys
        220                 225                 230

acc ccg gag ccc ccc gtg ccc tgt gtc cct gag cag acg gag tat gcc     771
Thr Pro Glu Pro Pro Val Pro Cys Val Pro Glu Gln Thr Glu Tyr Ala
    235                 240                 245
```

TABLE 1-continued

```
acc att gtc ttt cct agc gga atg ggc acc tca tcc ccc gcc cgc agg    819
Thr Ile Val Phe Pro Ser Gly Met Gly Thr Ser Ser Pro Ala Arg Arg
250                 255                 260                 265

ggc tca gct gac ggc cct cgg agt gcc cag cca ctg agg cct gag gat    867
Gly Ser Ala Asp Gly Pro Arg Ser Ala Gln Pro Leu Arg Pro Glu Asp
                270                 275                 280

gga cac tgc tct tgg ccc ctc tgaccggctt ccttggccac cagtgttctg cag   921
Gly His Cys Ser Trp Pro Leu
            285
```

SEQ ID NO: 2 Human PD-1 Amino Acid Sequence

```
Met Gln Ile Pro Gln Ala Pro Trp Pro Val Val Trp Ala Val Leu Gln
  1               5                  10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
     50                  55                  60

Leu Asn Trp Tyr Arg Met Ser Pro Ser Asn Gln Thr Asp Lys Leu Ala
 65                  70                  75                  80

Ala Phe Pro Glu Asp Arg Ser Gln Pro Gly Gln Asp Cys Arg Phe Arg
                 85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Ser Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285
```

SEQ ID NO: 3 Han PD-L1S cDNA Acid Sequence

```
gcttcccgag gctccgcacc agccgcgctt ctgtccgcct gcagggcatt ccagaaag     58

atg agg ata ttt gct gtc ttt ata ttc atg accc tac tgg cat ttg ctg   106
Met Arg Ile Phe Ala Val Phe Ile Phe Met Thr Tyr Trp His Leu Leu
  1               5                  10                  15

aac gca ttt act gtc acg gtt ccc aag gac cta tat gtg gta gag tat    154
Asn Ala Phe Thr Val Thr Val Pro Lys Asp Leu Tyr Val Val Glu Tyr
             20                  25                  30
```

TABLE 1-continued

```
ggt agc aat atg aca att gaa tgc aaa ttc cca gta gaa aaa caa tta    202
Gly Ser Asn Met Thr Ile Glu Cys Lys Phe Pro Val Glu Lys Gln Leu
         35                  40                  45

gac ctg gct gca cta att gtc tat tgg gaa atg gag gat aag aac att    250
Asp Leu Ala Ala Leu Ile Val Tyr Trp Glu Met Glu Asp Lys Asn Ile
     50                  55                  60

att caa ttt gtg cat gga gag gaa gac ctg aag gtt cag cat agt agc    298
Ile Gln Phe Val His Gly Glu Glu Asp Leu Lys Val Gln His Ser Ser
 65                  70                  75                  80

tac aga cag agg gcc cgg ctg ttg aag gac cag ctc tcc ctg gga aat    346
Tyr Arg Gln Arg Ala Arg Leu Leu Lys Asp Gln Leu Ser Leu Gly Asn
                 85                  90                  95

gct gca ctt cag atc aca gat gtg aaa ttg cag gat gca ggg gtg tac    394
Ala Ala Leu Gln Ile Thr Asp Val Lys Leu Gln Asp Ala Gly Val Tyr
            100                 105                 110

cgc tgc atg atc agc tat ggt ggt gcc gac tac aag cga att act gtg    442
Arg Cys Met Ile Ser Tyr Gly Gly Ala Asp Tyr Lys Arg Ile Thr Val
        115                 120                 125

aaa gtc aat gcc cca tac aac aaa atc aac caa aga att ttg gtt gtg    490
Lys Val Asn Ala Pro Tyr Asn Lys Ile Asn Gln Arg Ile Leu Val Val
    130                 135                 140

gat cca gtc acc tct gaa cat gaa ctg aca tgt cag gct gag ggc tac    538
Asp Pro Val Thr Ser Glu His Glu Leu Thr Cys Gln Ala Glu Gly Tyr
145                 150                 155                 160

ccc aag gcc gaa gtc atc tgg aca agc agt gac cat caa gtc ctg agt    586
Pro Lys Ala Glu Val Ile Trp Thr Ser Ser Asp His Gln Val Leu Ser
                165                 170                 175

ggt aag acc acc acc acc aat tcc aag aga gag gag aag ctt ttc aat    634
Gly Lys Thr Thr Thr Thr Asn Ser Lys Arg Glu Glu Lys Leu Phe Asn
            180                 185                 190

gtg acc agc aca ctg aga atc aac aca aca act aat gag att ttc tac    682
Val Thr Ser Thr Leu Arg Ile Asn Thr Thr Thr Asn Glu Ile Phe Tyr
        195                 200                 205

tgc act ttt agg aga tta gat cct gag gaa aac cat aca gct gaa ttg    730
Cys Thr Phe Arg Arg Leu Asp Pro Glu Glu Asn His Thr Ala Glu Leu
    210                 215                 220

gtc atc cca ggt aat att ctg aat gtg tcc att aaa ata tgt cta aca    778
Val Ile Pro Gly Asn Ile Leu Asn Val Ser Ile Lys Ile Cys Leu Thr
225                 230                 235                 240

ctg tcc cct agc acc tagcatgatg tctgcctatc atagtcattc agtgattgtt    833
Leu Ser Pro Ser Thr
                245

gaataaatga atgaatgaat aacactatgt ttacaaaata tatcctaatt cctcacctcc  893

attcatccaa accatattgt tacttaataa acattcagca gatatttatg gaataaaaaa  953

aaaaaaaaaa aaaaa                                                   968
```

SEQ ID NO: 4 Human PD-L1S Amino Acid Sequence

```
Met Arg Ile Phe Ala Val Phe Ile Phe Met Thr Tyr Trp His Leu Leu
  1               5                  10                  15

Asn Ala Phe Thr Val Thr Val Pro Lys Asp Leu Tyr Val Val Glu Tyr
             20                  25                  30

Gly Ser Asn Met Thr Ile Glu Cys Lys Phe Pro Val Glu Lys Gln Leu
         35                  40                  45

Asp Leu Ala Ala Leu Ile Val Tyr Trp Glu Met Glu Asp Lys Asn Ile
     50                  55                  60

Ile Gln Phe Val His Gly Glu Glu Asp Leu Lys Val Gln His Ser Ser
 65                  70                  75                  80
```

TABLE 1-continued

```
Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Gly Asn Ile Leu Asn Val Ser Ile Lys Ile Cys Leu Thr
225                 230                 235                 240

Leu Ser Pro Ser Thr
                245
```

SEQ ID NO: 5 Hman PD-L1M cDNA Acid Sequence

```
cgaggctccg caccagccgc gcttctgtcc gcctgcaggg cattccagaa agatgagg      58
                                                      Met Arg
                                                        1

ata ttt gct gtc ttt ata ttc atg acc tac tgg cat ttg ctg aac gca     106
Ile Phe Ala Val Phe Ile Phe Met Thr Tyr Trp His Leu Leu Asn Ala
          5                  10                  15

ttt act gtc acg gtt ccc aag gac cta tat gtg gta gag tat ggt agc     154
Phe Thr Val Thr Val Pro Lys Asp Leu Tyr Val Val Glu Tyr Gly Ser
     20                  25                  30

aat atg aca att gaa tgc aaa ttc cca gta gaa aaa caa tta gac ctg     202
Asn Met Thr Ile Glu Cys Lys Phe Pro Val Glu Lys Gln Leu Asp Leu
 35                  40                  45                  50

gct gca cta att gtc tat tgg gaa atg gag gat aag aac att att caa     250
Ala Ala Leu Ile Val Tyr Trp Glu Met Glu Asp Lys Asn Ile Ile Gln
                55                  60                  65

ttt gtg cat gga gag gaa gac ctg aag gtt cag cat agt agc tac aga     298
Phe Val His Gly Glu Glu Asp Leu Lys Val Gln His Ser Ser Tyr Arg
            70                  75                  80

cag agg gcc cgg ctg ttg aag gac cag ctc tcc ctg gga aat gct gca     346
Gln Arg Ala Arg Leu Leu Lys Asp Gln Leu Ser Leu Gly Asn Ala Ala
        85                  90                  95

ctt cag atc aca gat gtg aaa ttg cag gat gca ggg gtg tac cgc tgc     394
Leu Gln Ile Thr Asp Val Lys Leu Gln Asp Ala Gly Val Tyr Arg Cys
    100                 105                 110

atg atc agc tat ggt ggt gcc gac tac aag cga att act gtg aaa gtc     442
Met Ile Ser Tyr Gly Gly Ala Asp Tyr Lys Arg Ile Thr Val Lys Val
115                 120                 125                 130

aat gcc cca tac aac aaa atc aac caa aga att ttg gtt gtg gat cca     490
Asn Ala Pro Tyr Asn Lys Ile Asn Gln Arg Ile Leu Val Val Asp Pro
                135                 140                 145

gtc acc tct gaa cat gaa ctg aca tgt cag gct gag ggc tac ccc aag     538
Val Thr Ser Glu His Glu Leu Thr Cys Gln Ala Glu Gly Tyr Pro Lys
            150                 155                 160
```

TABLE 1-continued

```
gcc gaa gtc atc tgg aca agc agt gac cat caa gtc ctg agt ggt aag     586
Ala Glu Val Ile Trp Thr Ser Ser Asp His Gln Val Leu Ser Gly Lys
        165                 170                 175

acc acc acc acc aat tcc aag aga gag gag aag ctt ttc aat gtg acc     634
Thr Thr Thr Thr Asn Ser Lys Arg Glu Glu Lys Leu Phe Asn Val Thr
    180                 185                 190

agc aca ctg aga atc aac aca aca act aat gag att ttc tac tgc act     682
Ser Thr Leu Arg Ile Asn Thr Thr Thr Asn Glu Ile Phe Tyr Cys Thr
195                 200                 205                 210

ttt agg aga tta gat cct gag gaa aac cat aca gct gaa ttg gtc atc     730
Phe Arg Arg Leu Asp Pro Glu Glu Asn His Thr Ala Glu Leu Val Ile
                215                 220                 225

cca gaa cta cct ctg gca cat cct cca aat gaa agg act cac ttg gta     778
Pro Glu Leu Pro Leu Ala His Pro Pro Asn Glu Arg Thr His Leu Val
            230                 235                 240

att ctg gga gcc atc tta tta tgc ctt ggt gta gca ctg aca ttc atc     826
Ile Leu Gly Ala Ile Leu Leu Cys Leu Gly Val Ala Leu Thr Phe Ile
        245                 250                 255

ttc cgt tta aga aaa ggg aga atg atg gat gtg aaa aaa tgt ggc atc     674
Phe Arg Leu Arg Lys Gly Arg Met Met Asp Val Lys Lys Cys Gly Ile
    260                 265                 270

caa gat aca aac tca aag aag caa agt gat aca cat ttg gag gag acg     922
Gln Asp Thr Asn Ser Lys Lys Gln Ser Asp Thr His Leu Glu Glu Thr
275                 280                 285                 290

taatccagca ttggaacttc tgatcttcaa gcagggattc tcaacctgtg gtttaggggt   982

tcatcggggc tgagcgtgac aagaggaagg aatgggcccg tgggatgcag gcaatgtggg  1042

acttaaaagg cccaagcact gaaaatggaa cctggcgaaa gcagaggagg agaatgaaga  1102

aagatggagt caaacaggga gcctggaggg agaccttgat actttcaaat gcctgagggg  1162

ctcatcgacg cctgtgacag ggagaaagga tacttctgaa caaggagcct ccaagcaaat  1222

catccattgc tcatcctagg aagacgggtt gagaatccct aatttgaggg tcagttcctg  1282

cagaagtgcc ctttgcctcc actcaatgcc tcaatttgtt ttctgcatga ctgagagtct  1342

cagtgttgga acgggacagt atttatgtat gagtttttcc tatttatttt gagtctgtga  1402

ggtcttcttg tcatgtgagt gtggttgtga atgatttctt ttgaagatat attgtagtag  1462

atgttacaat tttgtcgcca aactaaactt gctgcttaat gatttgctca catctagtaa  1522

aacatggagt atttgtaaaa aaaaaaaaaa a
```

SEQ ID NO: 6 Human PD-L1M Amino Acid Sequence

```
Met Arg Ile Phe Ala Val Phe Ile Phe Met Thr Tyr Trp His Leu Leu
  1               5                  10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
 65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125
```

TABLE 1-continued

```
Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
        275                 280                 285

Glu Thr
    290
```

SEQ ID NO: 7 Human PD-L2 cDNA Acid Sequence

```
atg atc ttc ctc ctg cta atg ttg agc ctg gaa ttg cag ctt cac cag      48
Met Ile Phe Leu Leu Leu Met Leu Ser Leu Glu Leu Gln Leu His Gln
 1               5                  10                  15

ata gca gct tta ttc aca gtg aca gtc cct aag gaa ctg tac ata ata      96
Ile Ala Ala Leu Phe Thr Val Thr Val Pro Lys Glu Leu Tyr Ile Ile
             20                  25                  30

gag cat ggc agc aat gtg acc ctg gaa tgc aac ttt gac act gga agt     144
Glu His Gly Ser Asn Val Thr Leu Glu Cys Asn Phe Asp Thr Gly Ser
         35                  40                  45

cat gtg aac ctt gga gca ata aca gcc agt ttg caa aag gtg gaa aat     192
His Val Asn Leu Gly Ala Ile Thr Ala Ser Leu Gln Lys Val Glu Asn
     50                  55                  60

gat aca tcc cca cac cgt gaa aga gcc act ttg ctg gag gag cag ctg     240
Asp Thr Ser Pro His Arg Glu Arg Ala Thr Leu Leu Glu Glu Gln Leu
 65                  70                  75                  80

ccc cta ggg aag gcc tcg ttc cac ata cct caa gtc caa gtg agg gac     288
Pro Leu Gly Lys Ala Ser Phe His Ile Pro Gln Val Gln Val Arg Asp
                 85                  90                  95

gaa gga cag tac caa tgc ata atc atc tat ggg gtc gcc tgg gac tac     336
Glu Gly Gln Tyr Gln Cys Ile Ile Ile Tyr Gly Val Ala Trp Asp Tyr
            100                 105                 110

aag tac ctg act ctg aaa gtc aaa gct tcc tac agg aaa ata aac act     384
Lys Tyr Leu Thr Leu Lys Val Lys Ala Ser Tyr Arg Lys Ile Asn Thr
        115                 120                 125

cac atc cta aag gtt cca gaa aca gat gag gta gag ctc acc tgc cag     432
His Ile Leu Lys Val Pro Glu Thr Asp Glu Val Glu Leu Thr Cys Gln
    130                 135                 140

gct aca ggt tat cct ctg gca gaa gta tcc tgg cca aac gtc agc gtt     480
Ala Thr Gly Tyr Pro Leu Ala Glu Val Ser Trp Pro Asn Val Ser Val
145                 150                 155                 160

cct gcc aac acc agc cac tcc agg acc cct gaa ggc ctc tac cag gtc     528
Pro Ala Asn Thr Ser His Ser Arg Thr Pro Glu Gly Leu Tyr Gln Val
                165                 170                 175
```

TABLE 1-continued

```
acc agt gtt ctg cgc cta aag cca ccc cct ggc aga aac ttc agc tgt    576
Thr Ser Val Leu Arg Leu Lys Pro Pro Pro Gly Arg Asn Phe Ser Cys
            180                 185                 190

gtg ttc tgg aat act cac gtg agg gaa ctt act ttg gcc agc att gac    624
Val Phe Trp Asn Thr His Val Arg Glu Leu Thr Leu Ala Ser Ile Asp
        195                 200                 205

ctt caa agt cag atg gaa ccc agg acc cat cca act tgg ctg ctt cac    672
Leu Gln Ser Gln Met Glu Pro Arg Thr His Pro Thr Trp Leu Leu His
    210                 215                 220

att ttc atc ccc tcc tgc atc att gct ttc att ttc ata gcc aca gtg    720
Ile Phe Ile Pro Ser Cys Ile Ile Ala Phe Ile Phe Ile Ala Thr Val
225                 230                 235                 240

ata gcc cta aga aaa caa ctc tgt caa aag ctg tat tct tca aaa gac    768
Ile Ala Leu Arg Lys Gln Leu Cys Gln Lys Leu Tyr Ser Ser Lys Asp
                245                 250                 255

aca aca aaa aga cct gtc acc aca aca aag agg gaa gtg aac agt gct    816
Thr Thr Lys Arg Pro Val Thr Thr Thr Lys Arg Glu Val Asn Ser Ala
            260                 265                 270

atc                                                                819
Ile
```

SEQ ID NO: 8 Human PD-L2 amino Acid Sequence

```
Met Ile Phe Leu Leu Leu Met Leu Ser Leu Glu Leu Gln Leu His Gln
 1               5                  10                  15

Ile Ala Ala Leu Phe Thr Val Thr Val Pro Lys Glu Leu Tyr Ile Ile
            20                  25                  30

Glu His Gly Ser Asn Val Thr Leu Glu Cys Asn Phe Asp Thr Gly Ser
        35                  40                  45

His Val Asn Leu Gly Ala Ile Thr Ala Ser Leu Gln Lys Val Glu Asn
    50                  55                  60

Asp Thr Ser Pro His Arg Glu Arg Ala Thr Leu Leu Glu Glu Gln Leu
65                  70                   75                  80

Pro Leu Gly Lys Ala Ser Phe His Ile Pro Gln Val Gln Val Arg asp
                85                  90                  95

Glu Gly Gln Tyr Gln Cys Ile Ile Ile Tyr Gly Val Ala Trp Asp Tyr
            100                 105                 110

Lys Tyr Leu Thr Leu Lys Val Lys Ala Ser Tyr Arg Lys Ile Asn Thr
        115                 120                 125

His Ile Leu Lys Val Pro Glu Thr Asp Glu Val Glu Leu Thr Cys Gln
    130                 135                 140

Ala Thr Gly Tyr Pro Leu Ala Glu Val Ser Trp Pro Asn Val Ser Val
145                 150                 155                 160

Pro Ala Asn Thr Ser His Ser Arg Thr Pro Glu Gly Leu Tyr Gln Val
                165                 170                 175

Thr Ser Val Leu Arg Leu Lys Pro Pro Pro Gly Arg Asn Phe Ser Cys
            180                 185                 190

Val Phe Trp Asn Thr His Val Arg Glu Leu Thr Leu Ala Ser Ile Asp
        195                 200                 205

Leu Gln Ser Gln Met Glu Pro Arg Thr His Pro Thr Trp Leu Leu His
    210                 215                 220

Ile Phe Ile Pro Ser Cys Ile Ile Ala Phe Ile Phe Ile Ala Thr Val
225                 230                 235                 240
```

TABLE 1-continued

```
Ile Ala Leu Arg Lys Gln Leu Cys Gln Lys Leu Tyr Ser Ser Lys Asp
                245                 250                 255

Thr Thr Lys Arg Pro Val Thr Thr Thr Lys Arg Glu Val Asn Ser Ala
            260                 265                 270

Ile
```

SEQ ID NO: 9 Human RGMb cDNA Sequence

```
   1 atgataagga agaagaggaa gcgaagcgcg ccccccggcc catgccgcag ccacgggccc
  61 agacccgcca cggcgcccgc gccgccgccc tcgccggagc ccacgagacc tgcatggacg
 121 ggcatgggct tgagagcagc accttccagc gccgccgctg ccgccgccga ggttgagcag
 181 cgccgcagcc ccgggctctg ccccccgccg ctggagctgc tgctgctgct gctgttcagc
 241 ctcgggctgc tccacgcagg tgactgccaa cagccagccc aatgtcgaat ccagaaatgc
 301 accacggact tcgtgtccct gacttctcac ctgaactctg ccgttgacgg ctttgactct
 361 gagttttgca aggccttgcg tgcctatgct ggctgcaccc agcgaacttc aaaagcctgc
 421 cgtggcaacc tggtatacca ttctgccgtg ttgggtatca gtgacctcat gagccagagg
 481 aattgttcca aggatggacc cacatcctct accaaccccg aagtgaccca tgatccttgc
 541 aactatcaca gccacgctgg agccagggaa cacaggagag gggaccagaa tgatccttgc
 601 taccttttt gtggcttgtt tggagatcct cacctcagaa ctttcaagga taacttccaa
 661 acatgcaaag tagaaggggc ctggccactc atagataata attatctttc agttcaagtg
 721 acaaacgtac ctgtggtccc tggatccagt gctactgcta caaataagat cactattatc
 781 ttcaaagccc accatgagtg tacagatcag aaagtctacc aagctgtgac agatgacctg
 841 ccggccgcct ttgtggatgg caccaccagt ggtggggaca gcgatgccaa gagcctgcgt
 901 atcgtggaaa gggagagtgg ccactatgtg gagatgcacg cccgctatat agggaccaca
 961 gtgtttgtgc ggcaggtggg tcgctacctg acccttgcca tccgtatgcc tgaagacctg
1021 gccatgtcct acgaggagag ccaggacctg cagctgtgcg tgaacggctg ccccctgagt
1081 gaacgcatcg atgacgggca gggccaggtg tctgccatcc tgggacacag cctgcctcgc
1141 acctccttgg tgcaggcctg gcctggctac acactggaga ctgccaacac tcaatgccat
1201 gagaagatgc cagtgaagga catctatttc cagtcctgtg tcttcgacct gctcaccact
1261 ggtgatgcca actttactgc cgcagcccac agtgccttgg aggatgtgga ggccctgcac
1321 ccaaggaagg aacgctggca cattttcccc agcagtggca atgggactcc ccgtggaggc
1381 agtgatttgt ctgtcagtct aggactcacc tgcttgatcc ttatcgtgtt tttgtag
```

SEQ ID NO: 10 Human RGMb Amino Acid Sequence

```
  1 mirkkrkrsa ppgpcrshgp rpatapappp speptrpawt gmglraapss aaaaaaeveq
 61 rrspglcppp lelllllfs lgllhagdcq qpapcriqkc ttdfvsltsh lnsavdgfds
121 efckalraya gctqrtskac rgnlvyhsav lgisdlmsqr ncskdgptss tnpevthdpc
181 nyhshagare hrrgdqnpps ylfcglfgdp hlrtfkdnfq tckvegawpl idnnylsvqv
241 tnvpvvpgss atatnkitii fkahhectdq kvyqavtddl paafvdgtts ggdsdakslr
301 iveresghyv emharyigtt vfvrqvgryl tlairmpedl amsyeesqdl qlcvngcpls
361 eriddgqgqv sailghslpr tslvqawpgy tletantqch ekmpvkdiyf qscvfdlltt
421 gdanftaaah saledvealh prkerwhifp ssgngtprgg sdlsvslglt clilivfl
```

II. Agents that Modulate Immune Cell Activation

It is demonstrated herein that PD-L2 binds to both RGMb and PD-1, although the binding of RGMb to PD-L2 is weaker than that of PD-L2 binding to PD-1. Thus, the agents of the present invention described herein that modulate the interaction between RGMb and PD-1, whether directly or indirectly, can upregulate or downregulate the immune system and, thereby, upregulate or downregulate an immune response. Thus, modulation of the interaction between RGMb and PD-L2 results in modulation of the immune response. Agents that modulate such an interaction can do so either directly or indirectly.

The interaction between an RGMb polypeptide and a PD-L2 polypeptide results in the delivery of a co-inhibitory immune signal. Thus, in one embodiment, agents which directly block the interaction between RGMb and PD-L2 (e.g., anti-RGMb and/or anti-PD-L2 blocking antibodies) can prevent inhibitory signaling and upregulate an immune response. Alternatively, agents that indirectly block the interaction between RGMb and PD-L2 can prevent inhibitory signaling and upregulate an immune response. For example, PD-L2, by binding to a PD-1 polypeptide indirectly reduces the effective concentration of PD-L2 polypeptide available to bind to RGMb. Exemplary agents for upregulating an immune response include antibodies against RGMb or PD-L2 that block the interaction between RGMb and PD-L2; a non-activating form of RGMb or PD-L2 (e.g., a dominant negative polypeptide), small molecules or peptides that block the interaction between RGMb and PD-L2; fusion proteins (e.g. the extracellular portion of RGMb or PD-L2 fused to the Fe portion of an antibody or immunoglobulin) that bind to RGMb or PD-L2 and inhibit the interaction between RGMb and PD-L2; nucleic acid molecules that block RGMb and/or PD-L2 transcription or translation; a non-activating form of a natural RGMb ligand, a soluble form of a natural RGMb ligand, and a natural RGMb ligand fusion protein. Natural RGMb ligands are well known in the art and include, for example, BMP2, BMP4, and BMP receptors (Samad et al. (2005) *J. Biol. Chem.* 280:14122-1412).

In another embodiment, agents that promote the binding of an RGMb polypeptide to a PD-L2 polypeptide promote an inhibitory signal to an immune cell. Agents that modulate such an interaction can do so either directly or indirectly. Thus, in one embodiment, agents which directly enhance the interaction between RGMb and PD-L2 (RGMb agonists and/or PD-L2 agonists) can promote inhibitory signaling and downregulate an immune response. Alternatively, agents that block PD-1 binding of PD-L2 increase the effective concentration of PD-L2 available to bind to RGMb. Exemplary agents for downregulating an immune response include antibodies against RGMb or PD-L2 that activate or promote the interaction between RGMb and PD-L2; small molecules or peptides that activate or promote the interaction between RGMb and PD-L2; and blocking antibodies that bind PD-1 and inhibit the interaction between PD-1 and PD-L2.

Additional agents useful in the methods of the present invention include antibodies, small molecules, peptides, peptidomimetics, natural ligands, and derivatives of natural ligands, that can either bind and/or activate or inhibit protein biomarkers of the invention, including the biomarkers listed in Table 1, or fragments thereof; RNA interference, antisense, nucleic acid aptamers, etc. that can downregulate the expression and/or activity of the biomarkers of the invention, including the biomarkers listed in Table 1, or fragments thereof.

In one embodiment, isolated nucleic acid molecules that specifically hybridize with or encode one or more biomarkers listed in Table 1 or biologically active portions thereof. As used herein, the term "nucleic acid molecule" is intended to include DNA molecules (i.e., cDNA or genomic DNA) and RNA molecules (i.e., mRNA) and analogs of the DNA or RNA generated using nucleotide analogs. The nucleic acid molecule can be single-stranded or double-stranded, but preferably is double-stranded DNA. An "isolated" nucleic acid molecule is one which is separated from other nucleic acid molecules which are present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated nucleic acid molecules corresponding to the one or more biomarkers listed in Table 1 can contain less than about 5 kb, 4kb, 3kb, 2kb, 1 kb, 0.5 kb or 0.1 kb of nucleotide sequences which naturally flank the nucleic acid molecule in genomic DNA of the cell from which the nucleic acid is derived (i.e., a lymphoma cell). Moreover, an "isolated" nucleic acid molecule, such as a cDNA molecule, can be substantially free of other cellular material, or culture medium when produced by recombinant techniques, or chemical precursors or other chemicals when chemically synthesized.

A nucleic acid molecule of the present invention, e.g., a nucleic acid molecule having the nucleotide sequence of one or more biomarkers listed in Table 1 or a nucleotide sequence which is at least about 50%, preferably at least about 60%, more preferably at least about 70%, yet more preferably at least about 80%, still more preferably at least about 90%, and most preferably at least about 95% or more (e.g., about 98%) homologous to the nucleotide sequence of one or more biomarkers listed in Table 1 or a portion thereof (i.e., 100, 200, 300, 400, 450, 500, or more nucleotides), can be isolated using standard molecular biology techniques and the sequence information provided herein. For example, a human cDNA can be isolated from a human cell line (from Stratagene, LaJolla, Calif., or Clontech, Palo Alto, Calif.) using all or portion of the nucleic acid molecule, or fragment thereof, as a hybridization probe and standard hybridization techniques (i.e., as described in Sambrook, J., Fritsh, E. F., and Maniatis, *T. Molecular Cloning: A Laboratory Manual. 2nd, ed., Cold Spring Harbor Laboratory*, Cold Spring Harbor Laboratory Press, Cold Spring Harbor, N.Y., 1989). Moreover, a nucleic acid molecule encompassing all or a portion of the nucleotide sequence of one or more biomarkers listed in Table 1 or a nucleotide sequence which is at least about 50%, preferably at least about 60%, more preferably at least about 70%, yet more preferably at least about 80%, still more preferably at least about 90%, and most preferably at least about 95% or more homologous to the nucleotide sequence, or fragment thereof, can be isolated by the polymerase chain reaction using oligonucleotide primers designed based upon the sequence of the one or more biomarkers listed in Table 1, or fragment thereof, or the homologous nucleotide sequence. For example, mRNA can be isolated from muscle cells (i.e., by the guanidinium-thiocyanate extraction procedure of Chirgwin et al. (1979) *Biochemistry* 18: 5294-5299) and cDNA can be prepared using reverse transcriptase (i.e., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for PCR amplification can be designed according to well known methods in the art. A nucleic acid of the invention can be amplified using cDNA or, alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to the nucleotide sequence of one or more biomarkers listed in Table 1 can be prepared by standard synthetic techniques, i.e., using an automated DNA synthesizer.

Probes based on the nucleotide sequences of one or more biomarkers listed in Table 1 can be used to detect or confirm the desired transcripts or genomic sequences encoding the same or homologous proteins. In preferred embodiments, the probe further comprises a label group attached thereto, i.e., the label group can be a radioisotope, a fluorescent compound, an enzyme, or an enzyme co-factor. Such probes can be used as a part of a diagnostic test kit for identifying cells or tissue which express one or more biomarkers listed in Table 1, such as by measuring a level of one or more biomarkers nucleic acid in a sample of cells from a subject, i.e., detecting mRNA levels of one or more biomarkers listed in Table 1.

Nucleic acid molecules encoding proteins corresponding to one or more biomarkers listed in Table 1 from different species are also contemplated. For example, rat or monkey cDNA can be identified based on the nucleotide sequence of a human and/or mouse sequence and such sequences are well known in the art. In one embodiment, the nucleic acid molecule(s) of the invention encodes a protein or portion thereof which includes an amino acid sequence which is sufficiently homologous to an amino acid sequence of one or more biomarkers listed in Table 1, such that the protein or portion thereof modulates (e.g., enhance), one or more of the following biological activities: a) binding to the biomarker; b) modulating the copy number of the biomarker; c) modulating the expression level of the biomarker; and d) modulating the activity level of the biomarker.

As used herein, the language "sufficiently homologous" refers to proteins or portions thereof which have amino acid sequences which include a minimum number of identical or equivalent (e.g., an amino acid residue which has a similar side chain as an amino acid residue in one or more biomarkers listed in Table 1, or fragment thereof) amino acid residues to an amino acid sequence of the biomarker, or fragment thereof, such that the protein or portion thereof modulates (e.g., enhance) one or more of the following biological activities: a) binding to the biomarker; b) modulating the copy number of the biomarker; c) modulating the expression level of the biomarker; and d) modulating the activity level of the biomarker.

In another embodiment, the protein is at least about 50%, preferably at least about 60%, more preferably at least about 70%, 75%, 80%, 85%, 90%, 91%, 92%, 93%, 94%, 95%, 96%, 97%, 98%, 99% or more homologous to the entire amino acid sequence of the biomarker, or a fragment thereof.

Portions of proteins encoded by nucleic acid molecules of the one or more biomarkers listed in Tables 1-9 are preferably biologically active portions of the protein. As used herein, the term "biologically active portion" of one or more biomarkers listed in Table 1 is intended to include a portion, e.g., a domain/motif, that has one or more of the biological activities of the full-length protein.

Standard binding assays, e.g., immunoprecipitations and yeast two-hybrid assays, as described herein, or functional assays, e.g., RNAi or overexpression experiments, can be performed to determine the ability of the protein or a biologically active fragment thereof to maintain a biological activity of the full-length protein.

The invention further encompasses nucleic acid molecules that differ from the nucleotide sequence of the one or more biomarkers listed in Table 1, or fragment thereof due to degeneracy of the genetic code and thus encode the same protein as that encoded by the nucleotide sequence, or fragment thereof. In another embodiment, an isolated nucleic acid molecule of the invention has a nucleotide sequence encoding a protein having an amino acid sequence of one or more biomarkers listed in Table 1, or fragment thereof, or a protein having an amino acid sequence which is at least about 70%, 75%, 80%, 85%, 90%, 91%, 92%. 93%, 94%, 95%. 96%, 97%, 98%, 99% or more homologous to the amino acid sequence of the one or more biomarkers listed in Table 1, or fragment thereof. In another embodiment, a nucleic acid encoding a polypeptide consists of nucleic acid sequence encoding a portion of a full-length fragment of interest that is less than 195, 190, 185, 180, 175, 170, 165, 160, 155, 150, 145, 140, 135, 130, 125, 120, 115, 110, 105, 100, 95, 90, 85, 80, 75, or 70 amino acids in length.

It will be appreciated by those skilled in the art that DNA sequence polymorphisms that lead to changes in the amino acid sequences of the one or more biomarkers listed in Table 1 may exist within a population (e.g., a mammalian and/or human population). Such genetic polymorphisms may exist among individuals within a population due to natural allelic variation. As used herein, the terms "gene" and "recombinant gene" refer to nucleic acid molecules comprising an open reading frame encoding one or more biomarkers listed in Table 1, preferably a mammalian, e.g., human, protein. Such natural allelic variations can typically result in 1-5% variance in the nucleotide sequence of the one or more biomarkers listed in Table 1. Any and all such nucleotide variations and resulting amino acid polymorphisms in the one or more biomarkers listed in Table 1 that are the result of natural allelic variation and that do not alter the functional activity of the one or more biomarkers listed in Table 1 are intended to be within the scope of the invention. Moreover, nucleic acid molecules encoding one or more biomarkers listed in Table 1 proteins from other species.

In addition to naturally-occurring allelic variants of the one or more biomarkers listed in Table 1 sequence that may exist in the population, the skilled artisan will further appreciate that changes can be introduced by mutation into the nucleotide sequence, or fragment thereof, thereby leading to changes in the amino acid sequence of the encoded one or more biomarkers listed in Table 1, without altering the functional ability of the one or more biomarkers listed in Table 1. For example, nucleotide substitutions leading to amino acid substitutions at "non-essential" amino acid residues can be made in the sequence, or fragment thereof. A "non-essential" amino acid residue is a residue that can be altered from the wild-type sequence of the one or more biomarkers listed in Table 1 without altering the activity of the one or more biomarkers listed in Table 1, whereas an "essential" amino acid residue is required for the activity of the one or more biomarkers listed in Table 1. Other amino acid residues, however, (e.g., those that are not conserved or only semi-conserved between mouse and human) may not be essential for activity and thus are likely to be amenable to alteration without altering the activity of the one or more biomarkers listed in Table 1.

The term "sequence identity or homology" refers to the sequence similarity between two polypeptide molecules or between two nucleic acid molecules. When a position in both of the two compared sequences is occupied by the same base or amino acid monomer subunit, e.g., if a position in each of two DNA molecules is occupied by adenine, then the molecules are homologous or sequence identical at that position. The percent of homology or sequence identity between two sequences is a function of the number of matching or homologous identical positions shared by the two sequences divided by the number of positions compared×100. For example, if 6 of 10, of the positions in two sequences are the same then the two sequences are 60% homologous or have 60% sequence identity. By way of example, the DNA sequences ATTGCC and TATGGC share 50% homology or sequence identity. Generally, a comparison is made when two sequences are aligned to give maximum homology. Unless otherwise specified "loop out regions", e.g., those arising from, from deletions or insertions in one of the sequences are counted as mismatches.

The comparison of sequences and determination of percent homology between two sequences can be accomplished using a mathematical algorithm. Preferably, the alignment can be performed using the Clustal Method. Multiple alignment parameters include GAP Penalty=10, Gap Length Penalty=10. For DNA alignments, the pairwise alignment parameters can be Htuple=2, Gap penalty=5, Window-4, and Diagonal saved=4. For protein alignments, the pairwise alignment parameters can be Ktuple=1, Gap penalty=3, Window=5, and Diagonals Saved=5.

In a preferred embodiment, the percent identity between two amino acid sequences is determined using the Needleman and Wunsch (*J. Mol. Biol.* (48):444-453 (1970)) algorithm which has been incorporated into the GAP program in the GCG software package (available online), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available online), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (CABIOS, 4:11-17 (1989)) which has been incorporated into the ALIGN program (version 2.0) (available online), using a PAM120 weight residue table, a gap length penalty of 12 and a gap penalty of 4.

An isolated nucleic acid molecule encoding a protein homologous to one or more biomarkers listed in Table 1, or fragment thereof, can be created by introducing one or more nucleotide substitutions, additions or deletions into the nucleotide sequence, or fragment thereof, or a homologous nucleotide sequence such that one or more amino acid substitutions, additions or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), branched side chains (e.g., threonine, valine, isoleucine) and aromatic side chains (e.g., tyrosine, phenylalanine, tryptophan, histidine). Thus, a predicted nonessential amino acid residue in one or more biomarkers listed in Table 1 is preferably replaced with another amino acid residue from the same side chain family. Alternatively, in another embodiment, mutations can be introduced randomly along all or part of the coding sequence of the one or more biomarkers listed in Table 1, such as by saturation mutagenesis, and the resultant mutants can be screened for an activity described herein to identify mutants that retain desired activity. Following mutagenesis, the encoded protein can be expressed recombinantly according to well known methods in the art and the activity of the protein can be determined using, for example, assays described herein.

The levels of one or more biomarkers listed in Table 1 levels may be assessed by any of a wide variety of well known methods for detecting expression of a transcribed molecule or protein. Non-limiting examples of such methods include immunological methods for detection of proteins, protein purification methods, protein function or activity assays, nucleic acid hybridization methods, nucleic acid reverse transcription methods, and nucleic acid amplification methods.

In preferred embodiments, the levels of one or more biomarkers listed in Table 1 levels are ascertained by measuring gene transcript (e.g., mRNA), by a measure of the quantity of translated protein, or by a measure of gene product activity. Expression levels can be monitored in a variety of ways, including by detecting mRNA levels, protein levels, or protein activity, any of which can be measured using standard techniques. Detection can involve quantification of the level of gene expression (e.g., genomic DNA, cDNA, mRNA, protein, or enzyme activity), or, alternatively, can be a qualitative assessment of the level of gene expression, in particular in comparison with a control level. The type of level being detected will be clear from the context.

In a particular embodiment, the mRNA expression level can be determined both by in situ and by in vitro formats in a biological sample using methods known in the art. The term "biological sample" is intended to include tissues, cells, biological fluids and isolates thereof, isolated from a subject, as well as tissues, cells and fluids present within a subject. Many expression detection methods use isolated RNA. For in vitro methods, any RNA isolation technique that does not select against the isolation of mRNA can be utilized for the purification of RNA from cells (see, e.g., Ausubel et al., ed., *Current Protocols in Molecular Biology*, John Wiley & Sons, New York 1987-1999). Additionally, large numbers of tissue samples can readily be processed using techniques well known to those of skill in the art, such as, for example, the single-step RNA isolation process of Chomczynski (1989, U.S. Pat. No. 4,843,155).

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length cDNA, or a portion thereof, such as an oligonucleotide of at least 7, 15, 30, 50, 100, 250 or 500 nucleotides in length and sufficient to specifically hybridize under stringent conditions to a mRNA or genomic DNA encoding One or more biomarkers listed in Table 1. Other suitable probes for use in the diagnostic assays of the invention are described herein. Hybridization of an mRNA with the probe indicates that One or more biomarkers listed in Table 1 is being expressed.

In one format, the mRNA is immobilized on a solid surface and contacted with a probe, for example by running the isolated mRNA on an agarose gel and transferring the mRNA from the gel to a membrane, such as nitrocellulose. In an alternative format, the probe(s) are immobilized on a solid surface and the mRNA is contacted with the probe(s), for example, in a gene chip array, e.g., an Affymetrix™ gene chip array. A skilled artisan can readily adapt known mRNA detection methods for use in detecting the level of the One or more biomarkers listed in Table 1 mRNA expression levels.

An alternative method for determining mRNA expression level in a sample involves the process of nucleic acid amplification, e.g., by RT-PCR (the experimental embodiment set forth in Mullis, 1987, U.S. Pat. No. 4,683,202), ligase chain reaction (Barany, 1991, *Proc. Natl. Acad. Sci. USA,* 88:189-193), self sustained sequence replication (Guatelli et al., 1990, *Proc. Natl. Acad. Sci. USA* 87:1874-1878), transcriptional amplification system (Kwoh et al., 1989, *Proc. Natl. Acad. Sci. USA* 86:1173-1177), Q-Beta Replicase (Lizardi et al., 1988, *Bio/Technology* 6:1197), rolling circle replication (Lizardi et al., U.S. Pat. No. 5,854,033) or any other nucleic acid amplification method, followed by the detection of the amplified molecules using techniques well-known to those of skill in the art. These detection schemes are especially useful for the detection of nucleic acid molecules if such molecules are present in very low numbers. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, mRNA does not need to be isolated from the cells prior to detection. In such methods, a cell or tissue sample is prepared/processed using known histological methods. The sample is then immobilized on a support, typically a glass slide, and then contacted with a probe that can hybridize to the One or more biomarkers listed in Table 1 mRNA.

As an alternative to making determinations based on the absolute expression level, determinations may be based on the normalized expression level of one or more biomarkers listed in Table 1. Expression levels are normalized by correcting the absolute expression level by comparing its expression to the expression of a non-biomarker gene, e.g., a housekeeping gene that is constitutively expressed. Suitable genes for normalization include housekeeping genes such as the actin gene, or epithelial cell-specific genes. This normalization allows the comparison of the expression level in one sample, e.g., a subject sample, to another sample, e.g., a normal sample, or between samples from different sources.

The level or activity of a protein corresponding to one or more biomarkers listed in Table 1 can also be detected and/or quantified by detecting or quantifying the expressed polypeptide. The polypeptide can be detected and quantified by any of a number of means well known to those of skill in the art. These may include analytic biochemical methods such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunoelectrophoresis, radioimmunoassay (RIA), enzyme-linked immunosorbent assays (ELISAs), immunofluorescent assays, Western blotting, and the like. A skilled artisan can readily adapt known protein/antibody detection methods for use in determining whether cells express the biomarker of interest.

The present invention further provides soluble, purified and/or isolated polypeptide forms of one or more biomarkers listed in Table 1, or fragments thereof. In addition, it is to be understood that any and all attributes of the polypeptides described herein, such as percentage identities, polypeptide lengths, polypeptide fragments, biological activities, antibodies, etc. can be combined in any order or combination with respect to any biomarker listed in Table 1 and combinations thereof.

In one aspect, a polypeptide may comprise a full-length amino acid sequence corresponding to one or more biomarkers listed in Table 1 or a full-length amino acid sequence with 1 to about 20 conservative amino acid substitutions. An amino acid sequence of any described herein can also be at least 50, 55, 60, 65, 70, 75, 80, 85, 90, 91, 92, 93, 94, 95, 96, 97, 98, 99, or 99.5% identical to the full-length sequence of one or more biomarkers listed in Table 1, which is either described herein, well known in the art, or a fragment thereof. In another aspect, the present invention contemplates a composition comprising an isolated polyeptide corresponding to one or more biomarkers listed in Table 1 polypeptide and less than about 25%, or alternatively 15%, or alternatively 5%, contaminating biological macromolecules or polypeptides.

The present invention further provides compositions related to producing, detecting, or characterizing such polypeptides, or fragment thereof, such as nucleic acids, vectors, host cells, and the like. Such compositions may serve as compounds that modulate the expression and/or activity of one or more biomarkers listed in Table 1.

An isolated polypeptide or a fragment thereof (or a nucleic acid encoding such a polypeptide) corresponding to one or more biomarkers of the invention, including the biomarkers listed in Table 1 or fragments thereof, can be used as an immunogen to generate antibodies that bind to said immunogen, using standard techniques for polyclonal and monoclonal antibody preparation according to well known methods in the art. An antigenic peptide comprises at least 8 amino acid residues and encompasses an epitope present in the respective full length molecule such that an antibody raised against the peptide forms a specific immune complex with the respective full length molecule. Preferably, the antigenic peptide comprises at least 10 amino acid residues. In one embodiment such epitopes can be specific for a given polypeptide molecule from one species, such as mouse or human (i.e., an antigenic peptide that spans a region of the polypeptide molecule that is not conserved across species is used as immunogen; such non conserved residues can be determined using an alignment such as that provided herein).

In one embodiment, an antibody binds substantially specifically to PD-L2 and inhibits or enhances the interaction of PD-L2 with RGMb without inhibiting or enhancing the interaction of PD-L2 with PD-1. In another embodiment, an antibody binds substantially specifically to PD-L2 and inhibits or enhances both the interaction of PD-L2 with RGMb and the interaction of PD_l2 with PD-1. In a preferred embodiment, an antibody binds to a PD-L2 polypeptide and blocks the interaction between PD-L2 and RGMb without blocking the interaction between PD-L2 and PD-1. In another preferred embodiment, an antibody binds to a PD-L2 polypeptide and blocks the interaction between both PD-L2 and RGMb and PD-L2 and PD-1. In still another embodiment, an antibody binds substantially specifically to RGMb and inhibits or enhances the interaction of PD-L2 with RGMb.

For example, a polypeptide immunogen typically is used to prepare antibodies by immunizing a suitable subject (e.g., rabbit, goat, mouse or other mammal) with the immunogen. An appropriate immunogenic preparation can contain, for example, a recombinantly expressed or chemically synthesized molecule or fragment thereof to which the immune response is to be generated. The preparation can further include an adjuvant, such as Freund's complete or incomplete adjuvant, or similar immunostimulatory agent. Immunization of a suitable subject with an immunogenic preparation induces a polyclonal antibody response to the antigenic peptide contained therein.

Polyclonal antibodies can be prepared as described above by immunizing a suitable subject with a polypeptide immunogen. The polypeptide antibody titer in the immunized subject can be monitored over time by standard techniques, such as with an enzyme linked immunosorbent assay (ELISA) using immobilized polypeptide. If desired, the antibody directed against the antigen can be isolated from the mammal (e.g., from the blood) and further purified by well known techniques, such as protein A chromatography, to obtain the IgG fraction. At an appropriate time after immunization, e.g., when the antibody titers are highest, antibody-producing cells can be obtained from the subject and used to prepare monoclonal antibodies by standard techniques, such as the hybridoma technique (originally described by Kohler and Milstein (1975) *Nature* 256:495-497) (see also Brown et al. (1981) *J. Immunol.* 127:539-46; Brown et al. (1980) *J. Biol. Chem.* 255:4980-83; Yeh et al. (1976) *Proc. Natl. Acad. Sci.* 76:2927-31; Yeh et al. (1982) *Int. J. Cancer* 29:269-75), the more recent human B cell hybridoma technique (Kozbor et al. (1983) *Immunol. Today* 4:72), the EBV-hybridoma technique (Cole et al. (1985) *Monoclonal Antibodies and Cancer Therapy*, Alan R. Liss, Inc., pp. 77-96) or trioma techniques. The technology for producing monoclonal antibody hybridomas is well known (see generally Kenneth, R. H. in *Monoclonal Antibodies: A New Dimension In Biological Analyses*, Plenum Publishing Corp., New York, N.Y. (1980); Lerner, E. A. (1981) *Yale J. Biol. Med.* 54:387-402; Gefter, M. L. et al. (1977) *Somatic Cell Genet.* 3:231-36). Briefly, an immortal cell line (typically a myeloma) is fused to lymphocytes (typically splenocytes) from a mammal immunized with an immunogen as described above, and the culture supernatants of the resulting hybridoma cells are screened to identify a hybridoma producing a monoclonal antibody that binds to the polypeptide antigen, preferably specifically.

Any of the many well known protocols used for fusing lymphocytes and immortalized cell lines can be applied for the purpose of generating a monoclonal antibody against one or more biomarkers of the invention, including the biomarkers listed in Table 1, or a fragment thereof (see, e.g., Galfre, G. et al. (1977) *Nature* 266:55052; Gefter et al. (1977) supra; Lerner (1981) supra; Kenneth (1980) supra). Moreover, the ordinary skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from the American Type Culture Collection (ATCC), Rockville, Md. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind a given polypeptide, e.g., using a standard ELISA assay.

As an alternative to preparing monoclonal antibody-secreting hybridomas, a monoclonal specific for one of the above described polypeptides can be identified and isolated by screening a recombinant combinatorial immunoglobulin library (e.g., an antibody phage display library) with the appropriate polypeptide to thereby isolate immunoglobulin library members that bind the polypeptide. Kits for generating and screening phage display libraries are commercially available (e.g., the Pharmacia *Recombinant Phage Antibody System*, Catalog No. 27-9400-01; and the Stratagene *SurfZAP*™ Phage Display Kit, Catalog No. 240612). Additionally, examples of methods and reagents particularly amenable for use in generating and screening an antibody display library can be found in, for example, Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Biotechnology* (NY) 9:1369-1372; Hay et al. (1992) *Hum. Antibod. Hybridomas* 3:81-85; Huse et al. (1989) *Science* 246:1275-1281; Griffiths et al. (1993) *EMBO J.* 12:725-734; Hawkins et al. (1992) *J. Mol. Biol.* 226:889-896; Clarkson et al. (1991) *Nature* 352:624-628; Gram et al. (1992) *Proc. Natl. Acad. Sci. USA* 89:3576-3580; Garrard et al. (1991) *Biotechnology* (NY) 9:1373-1377; Hoogenboom et al. (1991) *Nucleic Acids Res.* 19:4133-4137: Barbas et al. (1991) *Proc. Natl. Acad Sci. USA* 88:7978-7982; and McCafferty et al. (1990) *Nature* 348:552-554.

Since it is well known in the art that antibody heavy and light chain CDR3 domains play a particularly important role in the binding specificity/affinity of an antibody for an antigen, the recombinant monoclonal antibodies of the present invention prepared as set forth above preferably comprise the heavy and light chain CDR3s of variable regions of the present invention (e.g., including the sequences of Table 3, or portions thereof). The antibodies further can comprise the CDR2s of variable regions of the present invention (e.g., including the sequences of Table 3, or portions thereof). The antibodies further can comprise the CDR is of variable regions of the present invention (e.g., including the sequences of Table 3, or portions thereof). In other embodiments, the antibodies can comprise any combinations of the CDRs.

The CDR1, 2, and/or 3 regions of the engineered antibodies described above can comprise the exact amino acid sequence(s) as those of variable regions of the present invention (e.g., including the sequences of Table 3, or portions thereof) disclosed herein. However, the ordinarily skilled artisan will appreciate that some deviation from the exact CDR sequences may be possible while still retaining the ability of the antibody to bind RGMb or PD-L2 effectively (e.g., conservative sequence modifications). Accordingly, in another embodiment, the engineered antibody may be composed of one or more CDRs that are, for example, 50%, 60%, 70%, 80%, 85%, 90%, 91%, 92%, 93%, 94%, 95%, 96%, 97%, 98%, 99%, or 99.5% identical to one or more CDRs of the present invention (e.g., including the sequences of Table 3, or portions thereof).

The structural features of non-human or human antibodies (e.g., a rat anti-mouse/anti-human RGMb antibody described herein) can be used to create structurally related human antibodies that retain at least one functional property of the antibodies of the present invention, such as binding to PD-L2 and/or RGMb. Another functional property includes inhibiting binding of the original known, non-human or human antibodies in a competition ELISA assay.

In some embodiments, monoclonal antibodies capable of binding human PD-L2 and/or RGMb are provided, comprising a heavy chain wherein the variable domain comprises at least a CDR having a sequence that is at least 80%, 85%, 90%, 91%, 92%, 93%, 94%. 95%, 96%, 97%. 98%, 99%, 99.5% or 100% identical from the group of heavy chain variable domain CDRs presented in Table 3.

Similarly, monoclonal antibodies capable of binding human PD-L2 and/or RGMb, comprising a light chain wherein the variable domain comprises at least a CDR having a sequence that is at least 80%, 85%, 90%, 91%, 92%, 93%, 94%, 95%, 96%, 97%, 98%, 99%, 99.5% or 100% identical from the group of light chain variable domain CDRs presented in Table 3, are also provided.

Monoclonal antibodies capable of binding human PD-L2 and/or RGMb, comprising a heavy chain wherein the variable domain comprises at least a CDR having a sequence that is at least 80%, 85%, 90%, 91%, 92%, 93%, 94%, 95%, 96%, 97%, 98%, 99%, 99.5% or 100% identical from the group of heavy chain variable domain CDRs presented in Table 3; and comprising a light chain wherein the variable domain comprises at least a CDR having a sequence that is at least 80%, 85%, 90%, 91%, 92%, 93%, 94%, 95%, 96%, 97%, 98%, 99%, 99.5% or 100% identical from the group of light chain variable domain CDRs presented in Table 3, are also provided.

A skilled artisan will note that such percentage homology is equivalent to and can be achieved by introducing 1, 2, 3, 4, 5, 6, 7, 8, 9, 10, or more conservative amino acid substitutions within a given CDR.

The monoclonal antibodies of the present invention can comprise a heavy chain, wherein the variable domain comprises at least a CDR having a sequence selected from the group consisting of the heavy chain variable domain CDRs presented in Table 3 and a light chain, wherein the variable domain comprises at least a CDR having a sequence selected from the group consisting of the light chain variable domain CDRs presented in Table 3.

Such monoclonal antibodies can comprise a light chain, wherein the variable domain comprises at least a CDR having a sequence selected from the group consisting of CDR-L1, CDR-L2, and CDR-L3, as described herein; and/or a heavy chain, wherein the variable domain comprises at least a CDR having a sequence selected from the group consisting of CDR-H1, CDR-H2, and CDR-H3, as described herein. In some embodiments, the monoclonal antibodies capable of binding human Gall comprises or consists of CDR-L1, CDR-L2, CDR-L3, CDR-H1. CDR-H2, and CDR-H3, as described herein.

The heavy chain variable domain of the monoclonal antibodies of the present invention can comprise or consist of the vH amino acid sequence set forth in Table 3 and/or the light chain variable domain of the monoclonal antibodies of the present invention can comprise or consist of the vκ amino acid sequence set forth in Table 3.

The present invention further provides fragments of said monoclonal antibodies which include, but are not limited to, Fv, Fab, F(ab')2, Fab', dsFv, scFv, sc(Fv)2 and diabodies; and multispecific antibodies formed from antibody fragments. For example, a number of immunoinhibitory molecules, such as PD-L1, PD-1, CTLA-4, and the like, can be bound in a bispecific or multispecific manner.

Other fragments of the monoclonal antibodies of the present invention are also contemplated. For example, individual immunoglobulin heavy and/or light chains are provided, wherein the variable domains thereof comprise at least a CDR presented in Table 3. In one embodiment, the immunoglobulin heavy chain comprises at least a CDR having a sequence that is at least 80%, 85%, 90%, 91%, 92%, 93%, 94%, 95%, 96%, 97%, 98%, 99%, 99.5% or 100% identical from the group of heavy chain or light chain variable domain CDRs presented in Table 3. In another embodiment, an immunoglobulin light chain comprises at least a CDR having a sequence that is at least 80%, 85%, 90%, 919%, 92%, 93%, 94%, 95%, 96%, 97%, 98%, 99%, 99.5% or 100% identical from the group of light chain or heavy chain variable domain CDRs described herein (e.g., presented in Table 3), are also provided.

In some embodiments, the immunoglobulin heavy and/or light chain comprises a variable domain comprising at least one of CDR-L1, CDR-L2, CDR-L3, CDR-H1, CDR-H2, or CDR-H3 described herein. Such immunoglobulin heavy chains can comprise or consist of at least one of CDR-H1, CDR-H2, and CDR-H3. Such immunoglobulin light chains can comprise or consist of at least one of CDR-L1, CDR-L2, and CDR-L3.

In other embodiments, an immunoglobulin heavy and/or light chain according to the present invention comprises or consists of a vH or vκ variable domain sequence, respectively, provided in Table 3.

The present invention further provides polypeptides which have a sequence selected from the group consisting of vH variable domain, vu variable domain, CDR-L1, CDR-L2, CDR-L3, CDR-H1, CDR-H2, and CDR-H3 sequences described herein.

Antibodies, immunoglobulins, and polypeptides of the invention can be use in an isolated (e.g., purified) form or contained in a vector, such as a membrane or lipid vesicle (e.g. a liposome).

Amino acid sequence modification(s) of the antibodies described herein are contemplated. For example, it may be desirable to improve the binding affinity and/or other biological properties of the antibody. It is known that when a humanized antibody is produced by simply grafting only CDRs in VH and VL of an antibody derived from a non-human animal in FRs of the VH and VL of a human antibody, the antigen binding activity is reduced in comparison with that of the original antibody derived from a non-human animal. It is considered that several amino acid residues of the VH and VL of the non-human antibody, not only in CDRs but also in FRs, are directly or indirectly associated with the antigen binding activity. Hence, substitution of these amino acid residues with different amino acid residues derived from FRs of the VH and VL of the human antibody would reduce binding activity and can be corrected by replacing the amino acids with amino acid residues of the original antibody derived from a non-human animal.

Modifications and changes may be made in the structure of the antibodies of the present invention, and in the DNA sequences encoding them, and still obtain a functional molecule that encodes an antibody and polypeptide with desirable characteristics. For example, certain amino acids may be substituted by other amino acids in a protein structure without appreciable loss of activity. Since the interactive capacity and nature of a protein define the protein's biological functional activity, certain amino acid substitutions can be made in a protein sequence, and, of course, in its DNA encoding sequence, while nevertheless obtaining a protein with like properties. It is thus contemplated that various changes may be made in the antibodies sequences of the invention, or corresponding DNA sequences which encode said polypeptides, without appreciable loss of their biological activity.

In making the changes in the amino sequences of polypeptide, the hydropathic index of amino acids may be considered. The importance of the hydropathic amino acid index in conferring interactive biologic function on a protein is generally understood in the art. It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of their hydrophobicity and charge characteristics these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophane (−0.9); tyrosine (−1.3); proline (−1.6); histidine (−3.2); glutamate (−3.5); glutamine (−3.5); aspartate (<RTI 3.5); asparagine (−3.5); lysine (−3.9); and arginine (−4.5).

It is known in the art that certain amino acids may be substituted by other amino acids having a similar hydropathic index or score and still result in a protein with similar biological activity, i.e. still obtain a biological functionally equivalent protein.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

Another type of amino acid modification of the antibody of the invention may be useful for altering the original glycosylation pattern of the antibody to, for example, increase stability. By "altering" is meant deleting one or more carbohydrate moieties found in the antibody, and/or adding one or more glycosylation sites that are not present in the antibody. Glycosylation of antibodies is typically N-linked. "N-linked" refers to the attachment of the carbohydrate moiety to the side chain of an asparagine residue. The tripeptide sequences asparagine-X-serine and asparagines-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. Addition of glycosylation sites to the antibody is conveniently accomplished by altering the amino acid sequence such that it contains one or more of the above-described tripeptide sequences (for N-linked glycosylation sites). Another type of covalent modification involves chemically or enzymatically coupling glycosides to the antibody. These procedures are advantageous in that they do not require production of the antibody in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, orhydroxyproline, (e) aromatic residues such as those of phenylalanine, tyrosine, or tryptophan, or (f) the amide group of glutamine. For example, such methods are described in WO87/05330.

Similarly, removal of any carbohydrate moieties present on the antibody may be accomplished chemically or enzymatically. Chemical deglycosylation requires exposure of the antibody to the compound trifluoromethanesulfonic acid, or an equivalent compound. This treatment results in the cleavage of most or all sugars except the linking sugar (N-acetylglucosamine or N-acetylgalactosamine), while leaving the antibody intact. Chemical deglycosylation is described by Sojahr et al. (1987) and by Edge et al. (1981). Enzymatic cleavage of carbohydrate moieties on antibodies can be achieved by the use of a variety of endo- and exo-glycosidases as described by Thotakura et al. (1987).

Other modifications can involve the formation of immunoconjugates. For example, in one type of covalent modification, antibodies or proteins are covalently linked to one of a variety of non proteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

Conjugation of antibodies or other proteins of the present invention with heterologous agents can be made using a variety of bifunctional protein coupling agents including but not limited to N-succinimidyl (2-pyridyldithio) propionate (SPDP), succinimidyl (N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6diisocyanate), and bis-active fluorine compounds (such as 1,5-difluoro-2,4-dinitrobenzene). For example, carbon labeled 1-isothiocyanatobenzyl methyldiethylene triaminepentaacetic acid (MX-DTPA) is an exemplary chelating agent for conjugation of radionucleotide to the antibody (WO 94/11026).

In another aspect, the present invention features antibodies conjugated to a therapeutic moiety, such as a cytotoxin, a drug, and/or a radioisotope. When conjugated to a cytotoxin, these antibody conjugates are referred to as "immunotoxins." A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). An antibody of the present invention can be conjugated to a radioisotope, e.g., radioactive iodine, to generate cytotoxic radiopharmaceuticals for treating a related disorder, such as a cancer.

Conjugated antibodies can be used diagnostically or prognostically to monitor polypeptide levels in tissue as part of a clinical testing procedure, e.g., to determine the efficacy of a given treatment regimen. Detection can be facilitated by coupling (i e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, P-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate (FITC), rhodamine, dichlorotriazinylamine fluorescein, dansyl chloride or phycoerythrin (PE); an example of a luminescent material includes luminol; examples of bioluminescent materials include luciferase, luciferin, and aequorin, and examples of suitable radioactive material include $^{125}I$, $^{131}I$, $^{35}S$, or $^{3}H$. [0134] As used herein, the term "labeled", with regard to the antibody, is intended to encompass direct labeling of the antibody by coupling (i.e., physically linking) a detectable substance, such as a radioactive agent or a fluorophore (e.g. fluorescein isothiocyanate (FITC) or phycoerythrin (PE) or Indocyanine (Cy5)) to the antibody, as well as indirect labeling of the antibody by reactivity with a detectable substance.

The antibody conjugates of the present invention can be used to modify a given biological response. The therapeutic moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, *Pseudomonas* exotoxin, or diphtheria toxin; a protein such as tumor necrosis factor or interferon-.gamma.; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other cytokines or growth factors.

Techniques for conjugating such therapeutic moiety to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243 56 (Alan R. Liss, Inc. 1985); Hellstrom et al., "Antibodies For Drug Delivery", in Controlled Drug Delivery (2nd Ed.), Robinson et al. (eds.), pp. 623 53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475 506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303 16 (Academic Press 1985), and Thorpe et al., "The Preparation And Cytotoxic Properties Of Antibody-Toxin Conjugates", Immunol. Rev., 62:119 58 (1982).

In some embodiments, conjugations can be made using a "cleavable linker" facilitating release of the cytotoxic agent or growth inhibitory agent in a cell. For example, an acid-labile linker, peptidase-sensitive linker, photolabile linker, dimethyl linker or disulfide-containing linker (See e.g. U.S. Pat. No. 5,208,020) may be used. Alternatively, a fusion protein comprising the antibody and cytotoxic agent or growth inhibitory agent may be made, by recombinant techniques or peptide synthesis. The length of DNA may comprise respective regions encoding the two portions of the conjugate either adjacent one another or separated by a region encoding a linker peptide which does not destroy the desired properties of the conjugate.

Additionally, recombinant polypeptide antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Patent Publication PCT/US86/02269; Akira et al. European Patent Application 184,187; Taniguchi, M. European Patent Application 171,496; Morrison et al. European Patent Application 173,494; Neuberger et al. PCT Application WO 86/01533; Cabilly et al. U.S. Pat. No. 4,816,567; Cabilly et al. European Patent Application 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci.* 84:214-218; Nishimura et al. (1987) *Cancer Res.* 47:999-1005; Wood et al. (1985) *Nature* 314:446-449; Shaw et al. (1988) *J. Natl. Cancer Inst.* 80:1553-1559); Morrison, S. L. (1985) *Science* 229:1202-1207; Oi et al. (1986) *Biotechniques* 4:214; Winter U.S. Pat. No. 5,225,539; Jones et al. (1986) *Nature* 321:552-525; Verhoeyan et al. (1988) *Science* 239:1534; and Beidler et al. (1988) *J. Immunol.* 141:4053-4060.

In addition, humanized antibodies can be made according to standard protocols such as those disclosed in U.S. Pat. No. 5,565,332. In another embodiment, antibody chains or specific binding pair members can be produced by recombination between vectors comprising nucleic acid molecules encoding a fusion of a polypeptide chain of a specific binding pair member and a component of a replicable generic display package and vectors containing nucleic acid molecules encoding a second polypeptide chain of a single binding pair member using techniques known in the art, e.g., as described in U.S. Pat. Nos. 5,565,332, 5,871,907, or 5,733,743. The use of intracellular antibodies to inhibit protein function in a cell is also known in the art (see e.g., Carlson, J. R. (1988) *Mol. Cell. Biol.* 8:2638-2646; Biocca, S. et al. (1990) *EMBO J.* 9:101-108; Werge, T. M. et al. (1990) *FEBS Lett.* 274:193-198; Carlson, J. R. (1993) *Proc. Natl. Acad. Sci. USA* 90:7427-7428; Marasco, W. A. et al. (1993) *Proc. Natl. Acad. Sci. USA* 90:7889-7893; Biocca, S. et al. (1994) *Biotechnology* (NY) 12:396-399; Chen, S-Y. et al. (1994) *Hum. Gene Ther.* 5:595-601; Duan, L et al. (1994)

*Proc. Natl. Acad Sci. USA* 91:5075-5079; Chen, S-Y. et al. (1994) *Proc. Natl. Acad. Sci. USA* 91:5932-5936; Beerli, R. R. et al. (1994) *J. Biol. Chem.* 269:23931-23936; Beerli, R. R. et al. (1994) *Biochem. Biophys. Res. Commun.* 204:666-672; Mhashilkar, A. M. et al. (1995) *EMBO J.* 14:1542-1551; Richardson, J. H. et al. (1995) *Proc. Natl. Acad. Sci. USA* 92:3137-3141; PCT Publication No. WO 94/02610 by Marasco et al.; and PCT Publication No. WO 95/03832 by Duan et al.).

Additionally, fully human antibodies could be made against biomarkers of the invention, including the biomarkers listed in Table 1, or fragments thereof. Fully human antibodies can be made in mice that are transgenic for human immunoglobulin genes, e.g. according to Hogan, et al., "Manipulating the Mouse Embryo: A Laboratory Manuel," Cold Spring Harbor Laboratory. Briefly, transgenic mice are immunized with purified immunogen. Spleen cells are harvested and fused to myeloma cells to produce hybridomas. Hybridomas are selected based on their ability to produce antibodies which bind to the immunogen. Fully human antibodies would reduce the immunogenicity of such antibodies in a human.

In one embodiment, an antibody for use in the instant invention is a bispecific antibody. A bispecific antibody has binding sites for two different antigens within a single antibody polypeptide. Antigen binding may be simultaneous or sequential. Triomas and hybrid hybridomas are two examples of cell lines that can secrete bispecific antibodies. Examples of bispecific antibodies produced by a hybrid hybridoma or a trioma are disclosed in U.S. Pat. No. 4,474,893. Bispecific antibodies have been constructed by chemical means (Staerz et al. (1985) *Nature* 314:628, and Perez et al. (1985) *Nature* 316:354) and hybridoma technology (Staerz and Bevan (1986) *Proc. Natl. Acad. Sci. USA,* 83:1453, and Staerz and Bevan (1986) *Immunol. Today* 7:241). Bispecific antibodies are also described in U.S. Pat. No. 5,959,084. Fragments of bispecific antibodies are described in U.S. Pat. No. 5,798,229.

Bispecific agents can also be generated by making heterohybridomas by fusing hybridomas or other cells making different antibodies, followed by identification of clones producing and co-assembling both antibodies. They can also be generated by chemical or genetic conjugation of complete immunoglobulin chains or portions thereof such as Fab and Fv sequences. The antibody component can bind to a polypeptide or a fragment thereof of one or more biomarkers of the invention, including one or more biomarkers listed in Table 1, or a fragment thereof. In one embodiment, the bispecific antibody could specifically bind to both a polypeptide or a fragment thereof and its natural binding partner (s) or a fragment(s) thereof.

In another aspect of this invention, peptides or peptide mimetics can be used to antagonize or agonize the activity of one or more biomarkers of the invention, including one or more biomarkers listed in Table 1, or a fragment(s) thereof. In one embodiment, variants of one or more biomarkers listed in Table 1 which function as a modulating agent for the respective full length protein, can be identified by screening combinatorial libraries of mutants, e.g., truncation mutants, for antagonist activity. In one embodiment, a variegated library of variants is generated by combinatorial mutagenesis at the nucleic acid level and is encoded by a variegated gene library. A variegated library of variants can be produced, for instance, by enzymatically ligating a mixture of synthetic oligonucleotides into gene sequences such that a degenerate set of potential polypeptide sequences is expressible as individual polypeptides containing the set of polypeptide sequences therein. There are a variety of methods which can be used to produce libraries of polypeptide variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential polypeptide sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of a polypeptide coding sequence can be used to generate a variegated population of polypeptide fragments for screening and subsequent selection of variants of a given polypeptide. In one embodiment, a library of coding sequence fragments can be generated by treating a double stranded PCR fragment of a polypeptide coding sequence with a nuclease under conditions wherein nicking occurs only about once per polypeptide, denaturing the double stranded DNA, renaturing the DNA to form double stranded DNA which can include sense/antisense pairs from different nicked products, removing single stranded portions from reformed duplexes by treatment with Si nuclease, and ligating the resulting fragment library into an expression vector. By this method, an expression library can be derived which encodes N-terminal, C-terminal and internal fragments of various sizes of the polypeptide.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of polypeptides. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of interest (Arkin and Youvan (1992) *Proc. Natl. Acad. Sci. USA* 89:7811-7815: Delagrave et al. (1993) *Protein Eng.* 6(3): 327-331). In one embodiment, cell based assays can be exploited to analyze a variegated polypeptide library. For example, a library of expression vectors can be transfected into a cell line which ordinarily synthesizes one or more biomarkers of the invention, including one or more biomarkers listed in Table 1, or a fragment thereof. The transfected cells are then cultured such that the full length polypeptide and a particular mutant polypeptide are produced and the effect of expression of the mutant on the full length polypeptide activity in cell supernatants can be detected, e.g., by any of a number of functional assays. Plasmid DNA can then be recovered from the cells which score for inhibition, or alternatively, potentiation of full length polypeptide activity, and the individual clones further characterized.

Systematic substitution of one or more amino acids of a polypeptide amino acid sequence with a D-amino acid of the same type (e.g., D-lysine in place of L-lysine) can be used to generate more stable peptides. In addition, constrained peptides comprising a polypeptide amino acid sequence of interest or a substantially identical sequence variation can be generated by methods known in the art (Rizo and Gierasch (1992) *Annu. Rev. Biochem.* 61:387, incorporated herein by reference); for example, by adding internal cysteine residues capable of forming intramolecular disulfide bridges which cyclize the peptide.

The amino acid sequences disclosed herein will enable those of skill in the art to produce polypeptides corresponding peptide sequences and sequence variants thereof. Such polypeptides can be produced in prokaryotic or eukaryotic host cells by expression of polynucleotides encoding the peptide sequence, frequently as part of a larger polypeptide. Alternatively, such peptides can be synthesized by chemical methods. Methods for expression of heterologous proteins in recombinant hosts, chemical synthesis of polypeptides, and in vitro translation are well known in the art and are described further in Maniatis et al. *Molecular Cloning: A Laboratory Manual* (1989), 2nd Ed., Cold Spring Harbor, N.Y.; Berger and Kimmel, Methods in Enzymology, Volume 152, Guide to Molecular Cloning Techniques (1987). Academic Press, Inc., San Diego, Calif.; Merrifield, J. (1969) *J. Am. Chem. Soc.* 91:501; Chaiken I. M. (1981) *CRC Crit. Rev. Biochem.* 11: 255; Kaiser et al. (1989) *Science* 243:187; Merrifield, B. (1986) *Science* 232:342; Kent, S. B. H. (1988) *Annu. Rev. Biochem.* 57:957; and Offord, R. E. (1980) *Semisynthetic Proteins*, Wiley Publishing, which are incorporated herein by reference).

Peptides can be produced, typically by direct chemical synthesis. Peptides can be produced as modified peptides, with nonpeptide moieties attached by covalent linkage to the N-terminus and/or C-terminus. In certain preferred embodiments, either the carboxy-terminus or the amino-terminus, or both, are chemically modified. The most common modifications of the terminal amino and carboxyl groups are acetylation and amidation, respectively. Amino-terminal modifications such as acylation (e.g., acetylation) or alkylation (e.g., methylation) and carboxy-terminal-modifications such as amidation, as well as other terminal modifications, including cyclization, can be incorporated into various embodiments of the invention. Certain amino-terminal and/or carboxy-terminal modifications and/or peptide extensions to the core sequence can provide advantageous physical, chemical, biochemical, and pharmacological properties, such as: enhanced stability, increased potency and/or efficacy, resistance to serum proteases, desirable pharmacokinetic properties, and others. Peptides disclosed herein can be used therapeutically to treat disease, e.g., by altering costimulation in a patient.

Peptidomimetics (Fauchere, J. (1986) *Adv. Drug Res.* 15:29; Veber and Freidinger (1985) TINS p. 392; and Evans et al. (1987) *J. Med. Chem.* 30:1229, which are incorporated herein by reference) are usually developed with the aid of computerized molecular modeling. Peptide mimetics that are structurally similar to therapeutically useful peptides can be used to produce an equivalent therapeutic or prophylactic effect. Generally, peptidomimetics are structurally similar to a paradigm polypeptide (i.e., a polypeptide that has a biological or pharmacological activity), but have one or more peptide linkages optionally replaced by a linkage selected from the group consisting of: —CH2NH—, —CH2S—, —CH2-CH2-, —CH═CH— (cis and trans), —COCH2-, —CH(OH)CH2-, and —CH2SO—, by methods known in the art and further described in the following references: Spatola, A. F. in "*Chemistry and Biochemistry of Amino Acids, Peptides, and Proteins*" Weinstein, B., ed., Marcel Dekker, New York, p. 267 (1983); Spatola, A. F., Vega Data (March 1983), Vol. 1, Issue 3, "Peptide Backbone Modifications" (general review); Morley, J. S. (1980) *Trends Pharm. Sci. pp.* 463-468 (general review); Hudson, D. et al. (1979) *Int. J. Pept. Prot. Res.* 14:177-185 (—CH2NH—, CH2CH2-); Spatola. A. F. et al. (1986) *Life Sci.* 38:1243-1249 (—CH2-S); Hann, M. M. (1982) *J. Chem. Soc. Perkin Trans. I.* 307-314 (—CH—CH—, cis and trans); Almquist, R. G. et al. (190) *J. Med. Chem.* 23:1392-1398 (—COCH2-); Jennings-White, C. et al. (1982) *Tetrahedron Lett.* 23:2533 (—COCH2-); Szelke, M. et al. European Appln. EP 45665 (1982) CA: 97:39405 (1982)(—CH(OH) CH2-); Holladay, M. W. et al. (1983) *Tetrahedron Lett.* (1983) 24:4401-4404 (—C(OH)CH2-); and Hruby, V. J. (1982) *Life Sci.* (1982) 31:189-199 (—CH2-S—); each of which is incorporated herein by reference. A particularly preferred non-peptide linkage is —CH2NH—. Such peptide mimetics may have significant advantages over polypeptide embodiments, including, for example: more economical production, greater chemical stability, enhanced pharmacological properties (half-life, absorption, potency, efficacy, etc.), altered specificity (e.g., a broad-spectrum of biological activities), reduced antigenicity, and others. Labeling of peptidomimetics usually involves covalent attachment of one or more labels, directly or through a spacer (e.g., an amide group), to non-interfering position(s) on the peptidomimetic that are predicted by quantitative structure-activity data and/or molecular modeling. Such non-interfering positions generally are positions that do not form direct contacts with the macropolypeptides(s) to which the peptidomimetic binds to produce the therapeutic effect. Derivitization (e.g., labeling) of peptidomimetics should not substantially interfere with the desired biological or pharmacological activity of the peptidomimetic.

Also encompassed by the present invention are small molecules which can modulate (either enhance or inhibit) interactions, e.g., between biomarkers listed in Table 1 and their natural binding partners. The small molecules of the present invention can be obtained using any of the numerous approaches in combinatorial library methods known in the art, including: spatially addressable parallel solid phase or solution phase libraries; synthetic library methods requiring deconvolution; the 'one-bead one-compound' library method; and synthetic library methods using affinity chromatography selection. (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. LISA* 90:6909; Erb et al. (1994) *Proc. Natl. Acad. Sci. USA* 91:11422; Zuckermann et al. (1994) *J. Med. Chem.* 37:2678; Cho et al. (1993) *Science* 261:1303; Carrell et al. (1994) *Angew. Chem. Int. Ed. Engl.* 33:2059: Carell et al. (1994) *Angew. Chem. Int. Ed Engl.* 33:2061; and in Gallop et al. (1994) *J. Med. Chem.* 37:1233.

Libraries of compounds can be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner USP '409), plasmids (Cull et al. (1992) *Proc. Natl. Acad. Sci. USA* 89:1865-1869) or on phage (Scott and Smith (1990) *Science* 249:386-390); (Devlin (1990) *Science* 249:404-406); (Cwirla et al. (1990) *Proc. Natl. Acad. Sci. USA* 87:6378-6382); (Felici (1991) *J. Mol. Biol.* 222:301-310); (Ladner supra.). Compounds can be screened in cell based or non-cell based assays. Compounds can be screened in pools (e.g. multiple compounds in each testing sample) or as individual compounds.

The invention also relates to chimeric or fusion proteins of the biomarkers of the invention, including the biomarkers listed in Table 1, or fragments thereof. As used herein, a "chimeric protein" or "fusion protein" comprises one or more biomarkers of the invention, including one or more biomarkers listed in Table 1, or a fragment thereof, operatively linked to another polypeptide having an amino acid sequence corresponding to a protein which is not substantially homologous to the respective biomarker. In a preferred embodiment, the fusion protein comprises at least one biologically active portion of one or more biomarkers of the invention, including one or more biomarkers listed in Table 1, or fragments thereof. Within the fusion protein, the term "operatively linked" is intended to indicate that the biomarker sequences and the non-biomarker sequences are fused in-frame to each other in such a way as to preserve functions exhibited when expressed independently of the fusion. The "another" sequences can be fused to the N-terminus or C-terminus of the biomarker sequences, respectively.

Such a fusion protein can be produced by recombinant expression of a nucleotide sequence encoding the first peptide and a nucleotide sequence encoding the second peptide. The second peptide may optionally correspond to a moiety that alters the solubility, affinity, stability or valency of the first peptide, for example, an immunoglobulin constant region. In another preferred embodiment, the first peptide consists of a portion of a biologically active molecule (e.g. the extracellular portion of the polypeptide or the ligand binding portion). The second peptide can include an immunoglobulin constant region, for example, a human Cγ1 domain or Cγ4 domain (e.g., the hinge. CH2 and CH3 regions of human IgCγ1, or human IgCγ4, see e.g., Capon et al. U.S. Pat. Nos. 5,116,964; 5,580,756; 5,844,095 and the like, incorporated herein by reference). Such constant regions may retain regions which mediate effector function (e.g. Fc receptor binding) or may be altered to reduce effector function. A resulting fusion protein may have altered solubility, binding affinity, stability and/or valency (i.e., the number of binding sites available per polypeptide) as compared to the independently expressed first peptide, and may increase the efficiency of protein purification. Fusion proteins and peptides produced by recombinant techniques can be secreted and isolated from a mixture of cells and medium containing the protein or peptide. Alternatively, the protein or peptide can be retained cytoplasmically and the cells harvested, lysed and the protein isolated. A cell culture typically includes host cells, media and other byproducts. Suitable media for cell culture are well known in the art. Protein and peptides can be isolated from cell culture media, host cells, or both using techniques known in the art for purifying proteins and peptides. Techniques for transfecting host cells and purifying proteins and peptides are known in the art.

Preferably, a fusion protein of the invention is produced by standard recombinant DNA techniques. For example. DNA fragments coding for the different polypeptide sequences are ligated together in-frame in accordance with conventional techniques, for example employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example. *Current Protocols in Molecular Biology*, eds. Ausubel et al. John Wiley & Sons: 1992).

Particularly preferred Ig fusion proteins include the extracellular domain portion or variable region-like domain of human RGMb, PD-L2, PD-1, or other biomarker listed in Table 1, coupled to an immunoglobulin constant region (e.g., the Fc region). The immunoglobulin constant region may contain genetic modifications which reduce or eliminate effector activity inherent in the immunoglobulin structure. For example, DNA encoding the extracellular portion of a polypeptide of interest can be joined to DNA encoding the hinge. CH2 and CH3 regions of human IgGγ1 and/or IgGγ4 modified by site directed mutagenesis, e.g., as taught in WO 97/28267.

In another embodiment, the fusion protein contains a heterologous signal sequence at its N-terminus. In certain host cells (e.g., mammalian host cells), expression and/or secretion of a polypeptide can be increased through use of a heterologous signal sequence.

The fusion proteins of the invention can be used as immunogens to produce antibodies in a subject. Such antibodies may be used to purify the respective natural polypeptides from which the fusion proteins were generated, or in screening assays to identify polypeptides which inhibit the interactions between one or more biomarkers polypeptide or a fragment thereof and its natural binding partner(s) or a fragment(s) thereof.

Also provided herein are compositions comprising one or more nucleic acids comprising or capable of expressing at least 1, 2, 3, 4, 5, 10, 20 or more small nucleic acids or antisense oligonucleotides or derivatives thereof, wherein said small nucleic acids or antisense oligonucleotides or derivatives thereof in a cell specifically hybridize (e.g., bind) under cellular conditions, with cellular nucleic acids (e.g., small non-coding RNAS such as miRNAs, pre-miRNAs, pri-miRNAs, miRNA*, anti-miRNA, a miRNA binding site, a variant and/or functional variant thereof, cellular mRNAs or a fragments thereof). In one embodiment, expression of the small nucleic acids or antisense oligonucleotides or derivatives thereof in a cell can enhance or upregulate one or more biological activities associated with the corresponding wild-type, naturally occurring, or synthetic small nucleic acids. In another embodiment, expression of the small nucleic acids or antisense oligonucleotides or derivatives thereof in a cell can inhibit expression or biological activity of cellular nucleic acids and/or proteins, e.g., by inhibiting transcription, translation and/or small nucleic acid processing of, for example, one or more biomarkers of the invention, including one or more biomarkerss listed in Table 1, or fragment(s) thereof. In one embodiment, the small nucleic acids or antisense oligonucleotides or derivatives thereof are small RNAs (e.g., microRNAs) or complements of small RNAs. In another embodiment, the small nucleic acids or antisense oligonucleotides or derivatives thereof can be single or double stranded and are at least six nucleotides in length and are less than about 1000, 900, 800, 700, 600, 500, 400, 300, 200, 100, 50, 40, 30, 25, 24, 23, 22, 21, 20, 19, 18, 17, 16, 15, or 10 nucleotides in length. In another embodiment, a composition may comprise a library of nucleic acids comprising or capable of expressing small nucleic acids or antisense oligonucleotides or derivatives thereof, or pools of said small nucleic acids or antisense oligonucleotides or derivatives thereof. A pool of nucleic acids may comprise about 2-5, 5-10, 10-20, 10-30 or more nucleic acids comprising or capable of expressing small nucleic acids or antisense oligonucleotides or derivatives thereof.

In one embodiment, binding may be by conventional base pair complementarity, or, for example, in the case of binding to DNA duplexes, through specific interactions in the major groove of the double helix. In general, "antisense" refers to the range of techniques generally employed in the art, and includes any process that relies on specific binding to oligonucleotide sequences.

It is well known in the art that modifications can be made to the sequence of a miRNA or a pre-miRNA without disrupting miRNA activity. As used herein, the term "functional variant" of a miRNA sequence refers to an oligonucleotide sequence that varies from the natural miRNA sequence, but retains one or more functional characteristics of the miRNA (e.g. cancer cell proliferation inhibition, induction of cancer cell apoptosis, enhancement of cancer cell susceptibility to chemotherapeutic agents, specific miRNA target inhibition). In some embodiments, a functional variant of a miRNA sequence retains all of the functional characteristics of the miRNA. In certain embodiments, a functional variant of a miRNA has a nucleobase sequence that is a least about 60%, 65%, 70%, 75%, 80%, 85%, 90%, 91%, 92%, 93%, 94%, 95%, 96%, 97%, 98% or 99% identical to the miRNA or precursor thereof over a region of about 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleobases, or that the functional variant hybridizes to the complement of the miRNA or precursor thereof under stringent hybridization conditions. Accordingly, in certain embodiments the nucleobase sequence of a functional variant is capable of hybridizing to one or more target sequences of the miRNA.

miRNAs and their corresponding stem-loop sequences described herein may be found in miRBase, an online searchable database of miRNA sequences and annotation, found on the world wide web at microrna.sanger.ac.uk. Entries in the miRBase Sequence database represent a predicted hairpin portion of a miRNA transcript (the stem-loop), with information on the location and sequence of the mature miRNA sequence. The miRNA stem-loop sequences in the database are not strictly precursor miRNAs (pre-miRNAs), and may in some instances include the pre-miRNA and some flanking sequence from the presumed primary transcript. The miRNA nucleobase sequences described herein encompass any version of the miRNA, including the sequences described in Release 10.0 of the miRBase sequence database and sequences described in any earlier Release of the miRBase sequence database. A sequence database release may result in the re-naming of certain miRNAs. A sequence database release may result in a variation of a mature miRNA sequence.

In some embodiments, miRNA sequences of the invention may be associated with a second RNA sequence that may be located on the same RNA molecule or on a separate RNA molecule as the miRNA sequence. In such cases, the miRNA sequence may be referred to as the active strand, while the second RNA sequence, which is at least partially complementary to the miRNA sequence, may be referred to as the complementary strand. The active and complementary strands are hybridized to create a double-stranded RNA that is similar to a naturally occurring miRNA precursor. The activity of a miRNA may be optimized by maximizing uptake of the active strand and minimizing uptake of the complementary strand by the miRNA protein complex that regulates gene translation. This can be done through modification and/or design of the complementary strand.

In some embodiments, the complementary strand is modified so that a chemical group other than a phosphate or hydroxyl at its 5' terminus. The presence of the 5' modification apparently eliminates uptake of the complementary strand and subsequently favors uptake of the active strand by the miRNA protein complex. The 5' modification can be any of a variety of molecules known in the art, including $NH_2$, $NHCOCH_3$, and biotin. In another embodiment, the uptake of the complementary strand by the miRNA pathway is reduced by incorporating nucleotides with sugar modifications in the first 2-6 nucleotides of the complementary strand. It should be noted that such sugar modifications can be combined with the 5' terminal modifications described above to further enhance miRNA activities.

In some embodiments, the complementary strand is designed so that nucleotides in the 3' end of the complementary strand are not complementary to the active strand. This results in double-strand hybrid RNAs that are stable at the 3' end of the active strand but relatively unstable at the 5' end of the active strand. This difference in stability enhances the uptake of the active strand by the miRNA pathway, while reducing uptake of the complementary strand, thereby enhancing miRNA activity.

Small nucleic acid and/or antisense constructs of the methods and compositions presented herein can be delivered, for example, as an expression plasmid which, when transcribed in the cell, produces RNA which is complementary to at least a unique portion of cellular nucleic acids (e.g., small RNAs, mRNA, and/or genomic DNA). Alternatively, the small nucleic acid molecules can produce RNA which encodes mRNA, miRNA, pre-miRNA, pri-miRNA, miRNA*, anti-miRNA, or a miRNA binding site, or a variant thereof. For example, selection of plasmids suitable for expressing the miRNAs, methods for inserting nucleic acid sequences into the plasmid, and methods of delivering the recombinant plasmid to the cells of interest are within the skill in the art. See, for example, Zeng et al. (2002), Molecular Cell 9:1327-1333; Tuschl (2002), Nat. Biotechnol, 20:446-448; Brummelkamp et al. (2002), Science 296: 550-553; Miyagishi et al. (2002), Nat. Biotechnol. 20:497-500: Paddison et al. (2002), Genes Dev. 16:948-958; Lee et al. (2002), Nat. Biotechnol. 20:500-505: and Paul et al. (2002), Nat. Biotechnol. 20:505-508, the entire disclosures of which are herein incorporated by reference.

Alternatively, small nucleic acids and/or antisense constructs are oligonucleotide probes that are generated ex vivo and which, when introduced into the cell, results in hybridization with cellular nucleic acids. Such oligonucleotide probes are preferably modified oligonucleotides that are resistant to endogenous nucleases, e.g., exonucleases and/or endonucleases, and are therefore stable in vivo. Exemplary nucleic acid molecules for use as small nucleic acids and/or antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by Van der Krol et al. (1988) BioTechniques 6:958-976; and Stein et al. (1988) Cancer Res 48:2659-2668.

Antisense approaches may involve the design of oligonucleotides (either DNA or RNA) that are complementary to cellular nucleic acids (e.g., complementary to biomarkers listed in Table 1). Absolute complementarity is not required. In the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with a nucleic acid (e.g., RNA) it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the mRNA, e.g., the 5' untranslated sequence up to and including the AUG initiation codon, should work most efficiently at inhibiting translation. However, sequences complementary to the 3' untranslated sequences of mRNAs have recently been shown to be effective at inhibiting translation of mRNAs as well (Wagner, R. (1994) Nature 372:333). Therefore, oligonucleotides complementary to either the 5' or 3' untranslated, non-coding regions of genes could be used in an antisense approach to inhibit translation of endogenous mRNAs. Oligonucleotides complementary to the 5' untranslated region of the mRNA may include the complement of the AUG start codon. Antisense oligonucleotides complementary to mRNA coding regions are less efficient inhibitors of translation but could also be used in accordance with the methods and compositions presented herein. Whether designed to hybridize to the 5', 3' or coding region of cellular mRNAs, small nucleic acids and/or antisense nucleic acids should be at least six nucleotides in length, and can be less than about 1000, 900, 800, 700, 600, 500, 400, 300, 200, 100, 50, 40, 30, 25, 24, 23, 22, 21, 20, 19, 18, 17, 16, 15, or 10 nucleotides in length.

Regardless of the choice of target sequence, it is preferred that in vitro studies are first performed to quantitate the ability of the antisense oligonucleotide to inhibit gene expression. In one embodiment these studies utilize controls that distinguish between antisense gene inhibition and nonspecific biological effects of oligonucleotides. In another embodiment these studies compare levels of the target nucleic acid or protein with that of an internal control nucleic acid or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

Small nucleic acids and/or antisense oligonucleotides can be DNA or RNA or chimeric mixtures or derivatives or modified versions thereof, single-stranded or double-stranded. Small nucleic acids and/or antisense oligonucleotides can be modified at the base moiety, sugar moiety, or phosphate backbone, for example, to improve stability of the molecule, hybridization, etc., and may include other appended groups such as peptides (e.g., for targeting host cell receptors), or agents facilitating transport across the cell membrane (see, e.g., Letsinger et al. (1989) Proc. Natl. Acad. Sci. U.S.A. 86:6553-6556; Lemaitre et al. (1987) Proc. Natl. Acad. Sci. 84:648-652; PCT Publication No. WO88/09810, published Dec. 15, 1988) or the blood-brain barrier (see, e.g., PCT Publication No. WO89/10134, published Apr. 25, 1988), hybridization-triggered cleavage agents. (See, e.g., Krol et al. (1988) BioTechniques 6:958-976) or intercalating agents. (See, e.g., Zon (1988), Pharm. Res. 5:539-549). To this end, small nucleic acids and/or antisense oligonucleotides may be conjugated to another molecule, e.g., a peptide, hybridization triggered cross-linking agent, transport agent, hybridization-triggered cleavage agent, etc.

Small nucleic acids and/or antisense oligonucleotides may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxytiethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Small nucleic acids and/or antisense oligonucleotides may also comprise at least one modified sugar moiety selected from the group including but not limited to arabinose, 2-fluoroarabinose, xylulose, and hexose.

In certain embodiments, a compound comprises an oligonucleotide (e.g., a miRNA or miRNA encoding oligonucleotide) conjugated to one or more moieties which enhance the activity, cellular distribution or cellular uptake of the resulting oligonucleotide. In certain such embodiments, the moiety is a cholesterol moiety (e.g., antagomirs) or a lipid moiety or liposome conjugate. Additional moieties for conjugation include carbohydrates, phospholipids, biotin, phenazine, folate, phenanthridine, anthraquinone, acridine, fluoresceins, rhodamines, coumarins, and dyes. In certain embodiments, a conjugate group is attached directly to the oligonucleotide. In certain embodiments, a conjugate group is attached to the oligonucleotide by a linking moiety selected from amino, hydroxyl, carboxylic acid, thiol, unsaturations (e.g., double or triple bonds), 8-amino-3,6-dioxaoctanoic acid (ADO), succinimidyl 4-(N-maleimidomethyl) cyclohexane-1-carboxylate (SMCC), 6-aminohexanoic acid (AHEX or AHA), substituted C1-C10 alkyl, substituted or unsubstituted C2-C10 alkenyl, and substituted or unsubstituted C2-C10 alkynyl. In certain such embodiments, a substituent group is selected from hydroxyl, amino, alkoxy, carboxy, benzyl, phenyl, nitro, thiol, thioalkoxy, halogen, alkyl, aryl, alkenyl and alkynyl.

In certain such embodiments, the compound comprises the oligonucleotide having one or more stabilizing groups that are attached to one or both termini of the oligonucleotide to enhance properties such as, for example, nuclease stability. Included in stabilizing groups are cap structures. These terminal modifications protect the oligonucleotide from exonuclease degradation, and can help in delivery and/or localization within a cell. The cap can be present at the 5'-terminus (5'-cap), or at the 3'-terminus (3'-cap), or can be present on both termini. Cap structures include, for example, inverted deoxy abasic caps.

Suitable cap structures include a 4',5'-methylene nucleotide, a 1-(beta-D-erythrofuranosyl) nucleotide, a 4'-thio nucleotide, a carbocyclic nucleotide, a 1,5-anhydrohexitol nucleotide, an L-nucleotide, an alpha-nucleotide, a modified base nucleotide, a phosphorodithioate linkage, a threopentofuranosyl nucleotide, an acyclic 3',4'-seco nucleotide, an acyclic 3,4-dihydroxybutyl nucleotide, an acyclic 3,5-dihydroxypentyl nucleotide, a 3'-3'-inverted nucleotide moiety, a 3'-3'-inverted abasic moiety, a 3'-2'-inverted nucleotide moiety, a 3'-2'-inverted abasic moiety, a 1,4-butanediol phosphate, a 3'-phosphoramidate, a hexylphosphate, an aminohexyl phosphate, a 3'-phosphate, a 3'-phosphorothioate, a phosphorodithioate, a bridging methylphosphonate moiety, and a non-bridging methylphosphonate moiety 5'-amino-alkyl phosphate, a 1,3-diamino-2-propyl phosphate, 3-aminopropyl phosphate, a 6-aminohexyl phosphate, a 1,2-aminododecyl phosphate, a hydroxypropyl phosphate, a 5'-5'-inverted nucleotide moiety, a 5'-5'-inverted abasic moiety, a 5'-phosphoramidate, a 5'-phosphorothioate, a 5'-amino, a bridging and/or non-bridging 5'-phosphoramidate, a phosphorothioate, and a 5'-mercapto moiety.

Small nucleic acids and/or antisense oligonucleotides can also contain a neutral peptide-like backbone. Such molecules are termed peptide nucleic acid (PNA)-oligomers and are described, e.g., in Perry-O'Keefe et al. (1996) Proc. Natl. Acad. Sci. U.S.A. 93:14670 and in Eglom et al. (1993) Nature 365:566. One advantage of PNA oligomers is their capability to bind to complementary DNA essentially independently from the ionic strength of the medium due to the neutral backbone of the DNA. In yet another embodiment, small nucleic acids and/or antisense oligonucleotides comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In a further embodiment, small nucleic acids and/or antisense oligonucleotides are α-anomeric oligonucleotides. An α-anomeric oligonucleotide forms specific double-stranded hybrids with complementary RNA in which, contrary to the usual b-units, the strands run parallel to each other (Gautier et al. (1987) Nucl. Acids Res. 15:6625-6641). The oligonucleotide is a 2'-O-methylribonucleotide (Inoue et al. (1987) Nucl. Acids Res. 15:6131-6148), or a chimeric RNA-DNA analogue (Inoue et al. (1987) FEBS Lett. 215: 327-330).

Small nucleic acids and/or antisense oligonucleotides of the methods and compositions presented herein may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein et al. (1988) Nucl. Acids Res. 16:3209, methylphosphonate oligonucleotides can be prepared by use of controlled pore glass polymer supports (Sarin et al. (1988) Proc. Natl. Acad. Sci. U.S.A. 85:7448-7451), etc. For example, an isolated miRNA can be chemically synthesized or recombinantly produced using methods known in the art. In some instances, miRNA are chemically synthesized using appropriately protected ribonucleoside phosphoramidites and a conventional DNA/RNA synthesizer. Commercial suppliers of synthetic RNA molecules or synthesis reagents include, e.g., Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA). Cruachem (Glasgow. UK), and Exiqon (Vedbaek, Denmark).

Small nucleic acids and/or antisense oligonucleotides can be delivered to cells in vivo. A number of methods have been developed for delivering small nucleic acids and/or antisense oligonucleotides DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systematically.

In one embodiment, small nucleic acids and/or antisense oligonucleotides may comprise or be generated from double stranded small interfering RNAs (siRNAs), in which sequences fully complementary to cellular nucleic acids (e.g. mRNAs) sequences mediate degradation or in which sequences incompletely complementary to cellular nucleic acids (e.g., mRNAs) mediate translational repression when expressed within cells. In another embodiment, double stranded siRNAs can be processed into single stranded antisense RNAs that bind single stranded cellular RNAs (e.g., microRNAs) and inhibit their expression. RNA interference (RNAi) is the process of sequence-specific, post-transcriptional gene silencing in animals and plants, initiated by double-stranded RNA (dsRNA) that is homologous in sequence to the silenced gene. in vivo, long dsRNA is cleaved by ribonuclease III to generate 21- and 22-nucleotide siRNAs. It has been shown that 21-nucleotide siRNA duplexes specifically suppress expression of endogenous and heterologous genes in different mammalian cell lines, including human embryonic kidney (293) and HeLa cells (Elbashir et al. (2001) *Nature* 411:494-498). Accordingly, translation of a gene in a cell can be inhibited by contacting the cell with short double stranded RNAs having a length of about 15 to 30 nucleotides or of about 18 to 21 nucleotides or of about 19 to 21 nucleotides. Alternatively, a vector encoding for such siRNAs or short hairpin RNAs (shRNAs) that are metabolized into siRNAs can be introduced into a target cell (see, e.g., McManus et al. (2002) RNA 8:842; Xia et al. (2002) Nature Biotechnology 20:1006; and Brummelkamp et al. (2002) Science 296:550). Vectors that can be used are commercially available, e.g., from OligoEngine under the name pSuper RNAi System™.

Ribozyme molecules designed to catalytically cleave cellular mRNA transcripts can also be used to prevent translation of cellular mRNAs and expression of cellular polypeptides, or both (See, e.g., PCT International Publication WO90/11364, published Oct. 4, 1990; Sarver et al. (1990) Science 247:1222-1225 and U.S. Pat. No. 5,093,246). While ribozymes that cleave mRNA at site specific recognition sequences can be used to destroy cellular mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach (1988) Nature 334:585-591. The ribozyme may be engineered so that the cleavage recognition site is located near the 5' end of cellular mRNAs; i.e., to increase efficiency and minimize the intracellular accumulation of non-functional mRNA transcripts.

The ribozymes of the methods and compositions presented herein also include RNA endoribonucleases (hereinafter "Cech-type ribozymes") such as the one which occurs naturally in *Tetrahymena thermophila* (known as the IVS, or L-19 IVS RNA) and which has been extensively described by Thomas Cech and collaborators (Zaug, et al. (1984) Science 224:574-578; Zaug, et al. (1986) Science 231:470-475; Zaug, et al. (1986) Nature 324:429-433; published International patent application No. WO88/04300 by University Patents Inc.; Been, et al. (1986) Cell 47:207-216). The Cech-type ribozymes have an eight base pair active site which hybridizes to a target RNA sequence whereafter cleavage of the target RNA takes place. The methods and compositions presented herein encompasses those Cech-type ribozymes which target eight base-pair active site sequences that are present in cellular genes.

As in the antisense approach, the ribozymes can be composed of modified oligonucleotides (e.g., for improved stability, targeting, etc.). A preferred method of delivery involves using a DNA construct "encoding" the ribozyme under the control of a strong constitutive pol III or pol II promoter, so that transfected cells will produce sufficient quantities of the ribozyme to destroy endogenous cellular messages and inhibit translation. Because ribozymes unlike antisense molecules, are catalytic, a lower intracellular concentration is required for efficiency.

Nucleic acid molecules to be used in triple helix formation for the inhibition of transcription of cellular genes are preferably single stranded and composed of deoxyribonucleotides. The base composition of these oligonucleotides should promote triple helix formation via Hoogsteen base pairing rules, which generally require sizable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC pairs, in which the majority of the purine residues are located on a single strand of the targeted duplex, resulting in CGC triplets across the three strands in the triplex.

Alternatively, the potential sequences that can be targeted for triple helix formation may be increased by creating a so called "switchback" nucleic acid molecule. Switchback molecules are synthesized in an alternating 5'-3', 3'-5' manner, such that they base pair with first one strand of a duplex and then the other, eliminating the necessity for a sizable stretch of either purines or pyrimidines to be present on one strand of a duplex.

Small nucleic acids (e.g., miRNAs, pre-miRNAs, pri-miRNAs, miRNA*, anti-miRNA, or a miRNA binding site, or a variant thereof), antisense oligonucleotides, ribozymes, and triple helix molecules of the methods and compositions presented herein may be prepared by any method known in the art for the synthesis of DNA and RNA molecules. These include techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Moreover, various well-known modifications to nucleic acid molecules may be introduced as a means of increasing intracellular stability and half-life. Possible modifications include but are not limited to the addition of flanking sequences of ribonucleotides or deoxyribonucleotides to the 5' and/or 3' ends of the molecule or the use of phosphorothioate or 2' O-methyl rather than phosphodiesterase linkages within the oligodeoxyribonucleotide backbone. One of skill in the art will readily understand that polypeptides, small nucleic acids, and antisense oligonucleotides can be further linked to another peptide or polypeptide (e.g., a heterologous peptide), e.g., that serves as a means of protein detection. Non-limiting examples of label peptide or polypeptide moieties useful for detection in the invention include, without limitation, suitable enzymes such as horseradish peroxidase, alkaline phosphatase, beta-galactosidase, or acetylcholinesterase; epitope tags, such as FLAG, MYC, HA, or HIS tags; fluorophores such as green fluorescent protein; dyes; radioisotopes; digoxygenin; biotin; antibodies; polymers; as well as others known in the art, for example, in Principles of Fluorescence Spectroscopy, Joseph R. Lakowicz (Editor), Plenum Pub Corp, 2nd edition (July 1999).

The modulatory agents described herein (e.g., antibodies, small molecules, peptides, fusion proteins, or small nucleic acids) can be incorporated into pharmaceutical compositions and administered to a subject in vivo. The compositions may contain a single such molecule or agent or any combination of agents described herein. "Single active agents" described herein can be combined with other pharmacologically active compounds ("second active agents") known in the art according to the methods and compositions provided herein. It is believed that certain combinations work synergistically in the treatment of conditions that would benefit from the mouldation of immune responses. Second active agents can be large molecules (e.g., proteins) or small molecules (e.g., synthetic inorganic, organometallic, or organic molecules). For example, anti-RGMb antibodies can be combined with anti-PD-1, anti-PD-L1, anti-PD-L2, anti-CTLA4, etc. antibodies and in any combination therein.

Examples of large molecule active agents include, but are not limited to, hematopoietic growth factors, cytokines, and monoclonal and polyclonal antibodies.

Typical large molecule active agents are biological molecules, such as naturally occurring or artificially made proteins. Proteins that are particularly useful in this invention include proteins that stimulate the survival and/or proliferation of hematopoietic precursor cells and immunologically active poietic cells in vitro or in vivo. Others stimulate the division and differentiation of committed crythroid progenitors in cells in vitro or in vivo. Particular proteins include, but are not limited to: interleukins, such as IL-2 (including recombinant IL-II ("rIL2") and canarypox IL-2), IL-10, IL-12, and IL-18; interferons, such as interferon alfa-2a, interferon alfa-2b, interferon alpha-n1, interferon alpha-n3, interferon beta-Ia, and interferon gamma-1b: GM-CF and GM-CSF; and EPO.

Particular proteins that can be used in the methods and compositions provided herein include, but are not limited to: filgrastim, which is sold in the United States under the trade name Neupogen® (Amgen, Thousand Oaks, Calif.); sargramostim, which is sold in the United States under the trade name Leukine® (Immunex, Seattle, Wash.); and recombinant EPO, which is sold in the United States under the trade name Epogen® (Amgen, Thousand Oaks, Calif.). Recombinant and mutated forms of GM-CSF can be prepared as described in U.S. Pat. Nos. 5,391,485; 5,393,870; and 5,229,496; all of which are incorporated herein by reference. Recombinant and mutated forms of G-CSF can be prepared as described in U.S. Pat. Nos. 4,810,643; 4,999,291; 5,528,823; and 5,580,755; all of which are incorporated herein by reference.

III. Methods of Selecting Agents that Modulate Immune Cell Activation

Another aspect of the invention relates to methods of selecting agents (e.g., antibodies, fusion proteins, peptides, or small molecules) which modulate an immune response by modulating costimulation, such as agents that inhibit or promote the interaction of RGMb with PD-L2. Such methods utilize screening assays, including cell based and non-cell based assays. In one embodiment, the assays provide a method for identifying agents that inhibit the interaction of RGMb with PD-L2 (e.g., with or without inhibiting the interaction of PD-1 with PD-L2).

In one embodiment, the invention relates to assays for screening candidate or test compounds that bind to, or modulate the activity of, RGMb and/or PD-L2. In one embodiment, a method for identifying an agent to modulate an immune response entails determining the ability of the agent to modulate, e.g. enhance or inhibit, the interaction between RGMb and PD-L2, and further determining the ability of the agent to modulate the interaction between a PD-1 and PD-L2. In one embodiment, an agent that modulates the interaction between RGMB and PD-L2 (e.g., without modulating the interaction between PD-1 and PD-L2) is selected. In another embodiment, an agent that modulates both the interaction between RGMb and PD-L2 and the interaction between PD-1 and PD-L2 is selected. Such agents include, without limitation, antibodies, proteins, fusion proteins, small molecules, and nucleic acids.

In one embodiment, a method for identifying an agent which enhances an immune response entails determining the ability of the candidate agent to enhance the interaction between RGMb and PD-L2 (e.g., with or without modulating the interaction between PD-1 and PD-L2).

In another embodiment, a method for identifying an agent to upregulate an immune response entails determining the ability of a candidate agent to inhibit the interaction between RGMb and PD-L2 (e.g., with or without modulating the interaction between PD-1 and PD-L2) and selecting an agent that inhibits the interaction between RGMb and PD-L2. In another embodiment, a method for identifying an agent to downregulate an immune response entails determining the ability of the candidate agent to enhance the interaction between RGMb and PD-L2 (e.g., with or without modulating the interaction between PD-1 and PD-L2) and selecting an agent that enhances the interaction between RGMb and PD-L2.

In one embodiment, an assay is a cell-based assay, comprising contacting (a) a cell expressing PD-L2 with an RGMb protein; (b) a cell expressing RGMb with a PD-L2 protein; or (c) a cell expressing PDL-2 with a cell expressing RGMb, with a test compound and determining the ability of the test compound to modulate (e.g. stimulate or inhibit) the binding between PD-L2 and RGMb. Determining the ability of the polypeptides to bind to, or interact with, each other can be accomplished, e.g., by measuring direct binding or by measuring a parameter of immune cell activation.

For example, in a direct binding assay, the polypeptides can be coupled with a radioisotope or enzymatic label such that binding of RGMb and PD-L2 can be determined by detecting the labeled protein in a complex. For example, the polypeptides can be labeled with $^{125}I$, $^{35}S$, $^{14}C$, or $^{3}H$, either directly or indirectly, and the radioisotope detected by direct counting of radioemmission or by scintillation counting. Alternatively, the polypeptides can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound to modulate the interaction between RGMb and PD-L2, without the labeling of any of the interactants. For example, a microphysiometer can be used to detect the interaction of RGMb and PD-L2 without the labeling of either polypeptide (McConnell, H. M. et al. (1992) *Science* 257:1906-1912). As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between compound and receptor.

In a preferred embodiment, determining the ability of the blocking agents (e.g. antibodies, fusion proteins, peptides, or small molecules) to antagonize the interaction between a given set of polypeptides can be accomplished by determining the activity of one or more members of the set of polypeptides. For example, the activity of RGMb or PD-L2 can be determined by detecting induction of a cellular second messenger (e.g., tyrosine kinase activity), detecting catalytic/enzymatic activity of an appropriate substrate, detecting the induction of a reporter gene (comprising a target-responsive regulatory element operatively linked to a nucleic acid encoding a detectable marker, e.g., chloramphenicol acetyl transferase), or detecting a cellular response regulated by RGMb and/or PD-L2. Determining the ability of the blocking agent to bind to or interact with said polypeptide can be accomplished, for example, by measuring the ability of a compound to modulate immune cell costimulation or inhibition in a proliferation assay, or by interfering with the ability of said polypeptide to bind to antibodies that recognize a portion thereof. In one embodiment, ability of the test compound to modulate one or more signaling activities selected from the group consisting of modulating FoxP3 expression, modulating phosphorylation of ERK1 or ERK2, modulating phosphorylation of PKC-θ, modulating phosphorylation of SHP-2, modulating cytokine production, and modulating cellular proliferation, is determined. In some embodiments, the test compound has an effect selected from the group consisting of (a) upregulates PD-L2/RGMb signaling and thereby downregulates ERK 1 or ERK 2 phosphorylation: (b) downregulates PD-L2/RGMb signaling and thereby upregulates ERK 1 or ERK 2 phosphorylation; (c) upregulates PD-L2/RGMb signaling and thereby downregulates PKC-θ phosphorylation; (d) downregulates PD-L2/RGMb signaling and thereby upregulates PKC-θ phosphorylation: (e) upregulates PD-L2/RGMb signaling and thereby upregulates SHSP-2 phosphorylation; and (f) downregulates PD-L2/RGMb signaling and thereby downregulates SHP-2 phosphorylation.

FoxP3, ERK1/ERK2, PKC-θ, and SHP-2 are well known in the art. For example, FOXP3 has a role in regulating the development of B cells, T cells and CD25+/CD4+ regulatory T cells. It is expressed in adult T-cell leukaemiallymphoma and is widely used as a marker of a population of regulatory T cells (Tregs) that control immunotolerance and enable tumour cells to evade the host response (Bignone and Banham (2008) EOBT 8:1897-1920). SHP-2 (also known as Syp, SHPTP2, PTP2C, PTPN11, PTP1D and BPTP3) is a member of the family of non-membrane tyrosine phosphatases (U.S. Pat. No. 5,589,375, and U.S. Pat. No. 5,831, 009). The SHP-2 protein contains two src homology 2 (SH2) domains, conserved regions of approximately 100 amino acids originally identified in Src protein tyrosine kinases, that promote protein-protein interactions through phosphotyrosyl residue binding (Neel, Semin. *Cell. Biol.* 4: 419-432 (1993)). These two domains have been shown to display differential functions in the regulation of the SHP-2 phosphatase and consequently affect different signaling pathways. The N-terminal SH2 domain serves as a regulatory and recruiting domain, producing an autoinhibitory effect through intramolecular interactions with the internal catalytic phosphatase domain. While the C-terminal SH2 domain acts merely to recruit other proteins for intermolecular interactions necessary for signal transduction (Pei et al., *Proc. Natl. Acad. Sci. U.S.A.* 93: 1141-1145 20 (1996)). The phosphorylation state of the SHP-2 molecule regulates its phosphatase activity. Protein-tyrosine phosphatases, including SH2-containing phosphatases, are highly conserved among eukaryotes from such diverse species as mammals, including humans, to yeast and *Xenopus*. SHP-2 has been shown to play a critical role in aberrant immunological responses (e.g., in the allergic response. (Pazdrak et al., *J. Exp.* 30 *Med.* 186: 561-568 (1997)). SHP-2 phosphorylation is easily detectable by methods known in the art, including, without limitation, the detection of altered mobility of the SHP-2 molecule on a PAGE gel, phosphorylation assays, and assays which measure the activity of the SHP-2 molecule. Detection of SHP-2 phosphorylation may be direct, or alternatively may be indirect, e.g., detection of a downstream activity or event.

ERK1 and ERK2 (also known as MAPK1 and MAPK2) are themselves kinases (Boulton, et al., *Cell* 65: 663-675, (1991)). Activation of the ERK molecule is via serine/threonine phosphorylation or tyrosine phosphorylation. Inhibition of ERK 1 and 2 activation may result from inhibition of upstream phosphorylation of the ERK 1 and 2 molecules, or may result from the activation of a phosphatase which dephosphorylates ERK1 and 2, to reduce activity. The ERK proteins are known to be activated by phosphorylation by the MEK molecule, a dual-specificity kinase. Upon activation, ERK1 and ERK2 translocate to the nucleus where they can directly phosphorylate and activate a variety of transcription 20 factors including c-Myc, C/EBP~, p62, TCF/Elk-1, ATF-2 and c-Jun. The phosphorylation state/activation state of the ERK1 and 2 molecules upon T cell activation is an indication of signaling via PD-1. The phosphorylation state/state of activation of ERK 1 and 2 can readily be determined by the skilled practitioner using assays readily available in the art. For instance, the phosphorylation state of the ERK1 25 and 2 molecules can be determined using an antibody specific for the phosphorylated form of the p42/44 ERK.1/2 proteins (phospho-Thr202/Tyr204 specific), several of which are commercially available. Alternatively, the phosphorylation state of the ERK.1 and 2 molecules can be determined by their mobility on a gel, using an antibody which recognizes ERK1 and 2, regardless of the phosphorylation state) for identification. Alternatively, the activation state of ERK.1 and 2 can be determined by assaying kinase activity of the ERK.1 and 2 molecules. Determination of the ERK1 and 2 phosphorylation/activation state may also by indirect methods, e.g., detection of a downstream activity or event.

The PKC isoenzymes play an important role in many cell signaling events. PKC-θ (also known as PKC-θ, PKCT, PRKCT, nPKC-θ and PRKCQ) is a calcium-independent isoform of the PKC family of serine-threonine kinases. Transient overexpression of the PKC-θ protein in murine thymoma cells resulted in transcriptional activation of an interleukin-2 promoter-driven construct (Baier et al., *Eur.* 15 *J Biochem.* 225: 195-203(1994)), indicating a role for PKC-θ in T-cell signaling pathways. PKC-θ has also been shown to be activated in the course of T cell receptor mediated T cell activation, and this activation correlates with translocation of the PKC-θ molecule to the plasma membrane at the site of APC contact (U.S. Pat. No. 6,040,152). PKC-θ has also been implicated in other cellular processes including apoptosis (Datta et al., *J Biol. Chem.* 272: 20317-20320 (1997)), cytoskeletal arrangement (Pietromonaco et al., *J Biol. Chem.* 273: 7594-7603 (1998); Simons et al., *Biochem. Biop~ys. Res. Commun.* 253: 561-565 (1998)), proliferation (Passalacqua et al., *Biochem. J* 337: 113-118 (1999)), and angiogenesis and wound repair (Tang et al., *J Biol. Chem.* 272: 28704-25 28711 (1997)). The phosphorylation state reflects the activation state of the PKC-θ molecule with phosphorylation indicating activation. The phosphorylation state/state of activation or PKC-θ can readily be determined by the skilled practitioner using assays readily available in the art. For instance, the phosphorylation state of the PKC-θ molecule can be determined using an antibody specific for the phosphorylated form of the PKC-θ protein (e.g., anti-phospho T538), which is commercially available. Alternatively, the phosphorylation state of the PKC-θ molecule can be determined by its mobility on a gel, using an antibody which recognizes PKC-θ (regardless of the phosphorylation state) for detection. Alternatively, the activation state of PKC-θ can be determined by assaying kinase activity of the PKC-θ molecule (Kupfer et al., U.S. Pat. No. 6,040,152), or by assaying for translocation to the membrane at the point of APC contact (Kupfer et al., U.S. Pat. No. 6,040,152). Determination of the PKC-θ phosphorylation/activation state may also be by indirect methods, e.g., detection of a downstream activity or event.

Agents that enhance interactions between RGMb and PD-L2 or block or inhibit interaction of PD-L2 with a costimulatory receptor can be identified by their ability to inhibit immune cell proliferation, and/or effector function, or to induce anergy, clonal deletion, and/or exhaustion when added to an in vitro assay. For example, cells can be cultured in the presence of an agent that stimulates signal transduction via an activating receptor. A number of recognized readouts of cell activation can be employed to measure, cell proliferation or effector function (e.g., antibody production, cytokine production, phagocytosis) in the presence of the activating agent. The ability of a test agent to block this activation can be readily determined by measuring the ability of the agent to effect a decrease in proliferation or effector function being measured, using techniques known in the art.

For example, agents of this invention can be tested for the ability to inhibit or enhance costimulation in a T cell assay, as described in Freeman et al. (2000) *J. Exp. Med.* 192:1027 and Latchman et al. (2001) *Nat. Immunol.* 2:261. CD4+ T cells can be isolated from human PBMCs and stimulated with activating anti-CD3 antibody. Proliferation of T cells can be measured by $^{3}$H thymidine incorporation. An assay can be performed with or without CD28 costimulation in the assay. Similar assays can be performed with Jurkat T cells and PHA-blasts from PBMCs.

Alternatively, agents of the present invention can be tested for the ability to modulate cellular production of cytokines which are produced by or whose production is enhanced or inhibited in immune cells in response to modulation of RGMb/PD-L2 activity. For example, immune cells expressing RGMb can be suboptimally stimulated in vitro with a primary activation signal, for example, T cells can be stimulated with phorbol ester, anti-CD3 antibody or preferably antigen in association with an MHC class II molecule, and given a costimulatory signal, e.g., by a stimulatory form of B7 family antigen, for instance by a cell transfected with nucleic acid encoding a B7 polypeptide and expressing the peptide on its surface or by a soluble, stimulatory form of the peptide. Known cytokines released into the media can be identified by ELISA or by the ability of an antibody which blocks the cytokine to inhibit immune cell proliferation or proliferation of other cell types that is induced by the cytokine. For example, an IL-4 ELISA kit is available from Genzyme (Cambridge Mass.), as is an IL-7 blocking antibody. Blocking antibodies against IL-9 and IL-12 are available from Genetics Institute (Cambridge, Mass.). The effect of stimulating or blocking the interaction of RGMb and PD-L2 on the cytokine profile can then be determined. An in vitro immune cell costimulation assay as described above can also be used in a method for identifying novel cytokines which can be modulated by modulation of RGMb/PD-L2 activity. For example, if a particular activity induced upon costimulation, e.g., immune cell proliferation, cannot be inhibited by addition of blocking antibodies to known cytokines, the activity may result from the action of an unknown cytokine. Following costimulation, this cytokine can be purified from the media by conventional methods and its activity measured by its ability to induce immune cell proliferation. To identify cytokines which may play a role the induction of tolerance, an in vitro T cell costimulation assay as described above can be used. In this case, T cells would be given the primary activation signal and contacted with a selected cytokine, but would not be given the costimulatory signal. After washing and resting the immune cells, the cells would be rechallenged with both a primary activation signal and a costimulatory signal. If the immune cells do not respond (e.g., proliferate or produce cytokines) they have become tolerized and the cytokine has not prevented the induction of tolerance. However, if the immune cells respond, induction of tolerance has been prevented by the cytokine. Those cytokines which are capable of preventing the induction of tolerance can be targeted for blockage in vivo in conjunction with reagents which block B lymphocyte antigens as a more efficient means to induce tolerance in transplant recipients or subjects with autoimmune diseases.

In yet another embodiment, an assay of the present invention is a cell-free for screening for compounds which modulate the binding of PD-L2 to RGMb comprising contacting a PD-L2 or RGMb protein, or biologically active portion thereof, with a test compound and determining the ability of the test compound to modulate the binding between the PD-L2 or RGMb protein, or biologically active portion thereof. Binding of the test compound can be determined either directly or indirectly as described above. In a preferred embodiment, the assay includes contacting the polypeptide, or biologically active portion thereof, with its binding partner to form an assay mixture, contacting the assay mixture with a test compound, and determining the ability of the test compound to interact with the polypeptide in the assay mixture, wherein determining the ability of the test compound to interact with the polypeptide comprises determining the ability of the test compound to preferentially bind to the polypeptide or biologically active portion thereof, as compared to the binding partner.

For example. RGMb and PD-L2 can be used to form an assay mixture and the ability of a polypeptide to block this interaction can be tested by determining the ability of RGMb to bind PD-L2 by one of the methods described above for determining direct binding. In some embodiments, whether for cell-based or cell-free assays, the test compound can further be assayed to determine whether it affects binding and/or activity of the interaction between PD-1 and PD-L2. Other useful binding analysis methods include the use of real-time Biomolecular Interaction Analysis (BIA) (Sjolander, S. and Urbaniczky, C. (1991) *Anal. Chem.* 63:2338-2345 and Szabo et al. (1995) *Curr. Opin. Struct. Biol.* 5:699-705). As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological polypeptides. Polypeptides of interest can be immobilized on a BIAcore chip and multiple agents (blocking antibodies, fusion proteins, peptides, or small molecules) can be tested for binding to the polypeptide of interest. An example of using the BIA technology is described by Fitz et al. (1997) *Oncogene* 15:613.

The cell-free assays of the present invention are amenable to use of both soluble and/or membrane-bound forms of proteins. In the case of cell-free assays in which a membrane-bound form protein is used (e.g., a cell surface RGMb or PD-L2) it may be desirable to utilize a solubilizing agent such that the membrane-bound form of the protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)n, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

In one or more embodiments of the above described assay methods, it may be desirable to immobilize either polypeptides to facilitate separation of complexed from uncomplexed forms of one or both of the proteins, as well as to accommodate automation of the assay. Binding of a test compound to a polypeptide, can be accomplished in any vessel suitable for containing the reactants. Examples of such vessels include microtiter plates, test tubes, and microcentrifuge tubes. In one embodiment, a fusion protein can be provided which adds a domain that allows one or both of the proteins to be bound to a matrix. For example, glutathione-S-transferase/RGMb polypeptide fusion proteins, or glutathione-S-transferase/target fusion proteins, can be adsorbed onto glutathione sepharose beads (Sigma Chemical, St. Louis, Mo.) or glutathione derivatized microtiter plates, which are then combined with the test compound, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of polypeptide binding or activity determined using standard techniques.

In an alternative embodiment, determining the ability of the test compound to modulate the activity of a polypeptide of interest (e.g., RGMb or PD-L2) can be accomplished as described above for cell-based assays, such as by determining the ability of the test compound to modulate the activity of a polypeptide that functions downstream of the polypeptide. For example, levels of second messengers can be determined, the activity of the interactor polypeptide on an appropriate target can be determined, or the binding of the interactor to an appropriate target can be determined as previously described.

This invention further pertains to novel agents identified by the above-described screening assays. Accordingly, it is within the scope of this invention to further use an agent identified as described herein in an appropriate animal model. For example, an agent identified as described herein can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

IV. Pharmaceutical Compositions

A agents that modulate (e.g., inhibit or promote) the interaction of RGMb and PD-L2, with or without blocking the interaction between PD-1 and PD-L2, including, e.g., blocking antibodies, peptides, fusion proteins, or small molecules, can be incorporated into pharmaceutical compositions suitable for administration to a subject. Such compositions typically comprise the antibody, peptide, fusion protein or small molecule and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition should be sterile and should be fluid to the extent that easy syringeability exists. It must be stable under the conditions of manufacture and storage and should be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it is preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, modulatory agents are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations should be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by, and directly dependent on, the unique characteristics of the active compound, the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

The above described modulating agents may be administered it he form of expressible nucleic acids which encode said agents. Such nucleic acids and compositions in which they are contained, are also encompassed by the present invention. For instance, the nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The modulatory agents described herein can be used according to a number of methods related to the modulation of the interaction between RGMb and PD-L2 and corresponding modulation (e.g., upregulation or downregulation) of immune responses.

1. Prophylactic Methods

In one aspect, the present invention provides a method for preventing in a subject, a disease or condition associated with an unwanted or less than desirable immune response. Subjects at risk for a disease that would benefit from treatment with the claimed agents or methods can be identified, for example, by any or a combination of diagnostic or prognostic assays known in the art. Administration of a prophylactic agent can occur prior to the manifestation of symptoms associated with an unwanted or less than desirable immune response. The appropriate agent used for treatment (e.g. antibodies, peptides, fusion proteins or small molecules) can be determined based on clinical indications and can be identified, e.g., using screening assays described herein.

2. Therapeutic Methods

Another aspect of the invention pertains to therapeutic methods of modulating an immune response, e.g., by modulating the interaction between RGMb and PD-L2.

Modulatory methods of the present invention involve contacting a cell with an agent that modulates the interaction between RGMb and PD-L2. Exemplary agent that modulates the interaction between RGMb and PD-L2 have been described above. For example, an agent that modulates RGMb or PD-L2 polypeptide activity includes a nucleic acid or a protein molecule, a naturally-occurring target molecule of RGMb or PD-L2 protein (e.g., PD-1. BMP-2, BMP-4, BMP receptors), an anti-RGMb or anti-PD-L2 antibody, RGMb or PD-L2 agonists or antagonist (e.g., antisense nucleic acid molecule, triplex oligonucleotide, and ribozymes), a peptidomimetic of a RGMb or PD-L2 agonist or antagonist, nucleic acid agonists or antagonists of RGMb or PD-L2 expression or activity, or other small molecule.

In a preferred embodiment, an agent that modulates the expression of RGMb or PD-L2 is, e.g., an antisense nucleic acid molecule, triplex oligonucleotide, a ribozyme, or a recombinant vector for expression of a RGMb or PD-L2 protein.

These modulatory agents can be administered in vitro (e.g., by contacting the cell with the agent) or, alternatively, in vivo (e.g., by administering the agent to a subject). As such, the present invention relates to methods of treating an individual afflicted with a disease or disorder that would benefit from modulation of an immune response, e.g., by modulation of the interaction between RGMb and PD-L2.

3. Downregulation of Immune Responses by Modulating RGMb/PD-L2 Interactions

There are numerous embodiments of the invention for upregulating the inhibitory function resulting from the interaction of RGMb with PD-L2 to thereby downregulate immune responses (e.g., agents that promote the binding of PD-L1 to RGMb). Downregulation can be in the form of inhibiting or blocking an immune response already in progress, or may involve preventing the induction of an immune response. The functions of activated immune cells can be inhibited by down-regulating immune cell responses, or by inducing specific anergy in immune cells, or both.

In one embodiment of the invention, tolerance is induced against specific antigens by co-administering an antigen with an agent (e.g. antibody, peptide, fusion protein, or small molecule) that blocks the interaction between RGMb and PD-L2. For example, tolerance can be induced to specific proteins. In one embodiment, immune responses to allergens (e.g., food allergens), or to foreign proteins to which an immune response is undesirable, can be inhibited. For example, patients that receive Factor VIII frequently generate antibodies against this clotting factor. Co-administration of an agent that enhances a RGMb/PD-L2-mediated inhibitory signal in combination with recombinant factor VIII (or by physically linked to Factor VIII, e.g., by cross-linking) can result in downmodulation. In similar manners, reduced clonal deletion and/or increased exhaustion (e.g., T cell exhaustion) can be induced.

In another embodiment, treatment methods may further use agents that block an activity of costimulatory pathways, such as that of other B lymphocyte antigen like B7-1, B7-2, or B7-3) to further downmodulate immune responses. Two separate agents that downmodulate immune responses can be combined as a single composition or administered separately (simultaneously or sequentially) to more effectively downregulate immune cell mediated immune responses in a subject. Furthermore, a therapeutically active amount of one or more of the subject agents, can be used in conjunction with other downmodulating reagents to influence immune responses. Examples of other immunomodulating reagents include, without limitation, antibodies that block a costimulatory signal, (e.g., against CD28 or ICOS), antibodies that act as agonists of CTLA4, and/or antibodies against other immune cell markers (e.g., against CD40, against CD40 ligand, or against cytokines), fusion proteins (e.g., CTLA4-Fc), and immunosuppressive drugs, (e.g., rapamycin, cyclosporine A or FK506).

Downregulating immune responses is useful for treating a number of conditions, e.g., in situations of tissue, skin and organ transplantation, in graft-versus-host disease (GVHD), or in autoimmune diseases such as systemic lupus erythematosus, multiple sclerosis, allergy, a transplant, hypersensitivity response, a disorder requiring increased CD4+ T cell production or function, a disorder requiring improved vaccination efficiency, a disorder requiring increased regulatory T cell production or function, and a disorder requiring improved vaccination efficiency. For example, blockage of immune cell function results in reduced tissue destruction in tissue transplantation. Typically, in tissue transplants, rejection of the transplant is initiated through its recognition as foreign by immune cells, followed by an immune reaction that destroys the transplant. The administration of an agent described herein prior to or at the time of transplantation can promote the generation of an inhibitory signal. Moreover, inhibition may also be sufficient to anergize the immune cells, thereby inducing tolerance in a subject. Induction of long-term tolerance avoids the necessity of repeated administration of these blocking reagents.

Downmodulation of immune responses are also useful in treating autoimmune disease. Many autoimmune disorders are the result of inappropriate activation of immune cells that are reactive against self tissue and which promote the production of cytokines and autoantibodies involved in the pathology of the diseases. Preventing the activation of autoreactive immune cells may reduce or eliminate disease symptoms. Administration of agents described herein are useful for preventing the generating of autoantibodies or cytokines which may be involved in the disease process. Additionally, agents that promote an inhibitory function mediated by the interaction between RGMb and PD-L2 may induce antigen-specific tolerance of autoreactive immune cells, which could lead to long-term relief from the disease. The efficacy of reagents in preventing or alleviating autoimmune disorders can be determined using a number of well-characterized animal models of human autoimmune diseases. Examples include murine experimental autoimmune encephalitis, systemic lupus erythematosus in MRL/lpr/lpr mice or NZB hybrid mice, murine autoimmune collagen arthritis, diabetes mellitus in NOD mice and BB rats, and murine experimental myasthenia gravis (see, e.g., Paul ed., *Fundamental Immunology*, Raven Press, New York, Third Edition 1993, chapter 30).

Inhibition of immune cell activation is also useful therapeutically in the treatment of allergy and allergic reactions, e.g., by inhibiting IgE production. Allergic reactions can be systemic or local in nature, depending on the route of entry of the allergen and the pattern of deposition of IgE on mast cells or basophils. Thus, inhibition of immune cell mediated allergic responses (e.g., to food) locally or systemically by administration of an agent described herein that promotes an inhibitory function mediated by RGMb and PD-L2.

Inhibition of immune cell activation may also be important therapeutically in parasitic and viral infections of immune cells. For example, in the acquired immune deficiency syndrome (AIDS), viral replication is stimulated by immune cell activation. Modulation of these interactions may result in inhibition of viral replication and thereby ameliorate the course of AIDS. Modulation of these interactions may also be useful in promoting the maintenance of pregnancy. Females at risk for spontaneous abortion (e.g., those who have previously had a spontaneous abortion or those who have had difficulty conceiving) because of immunologic rejection of the embryo or fetus can be treated with agents that modulate these interactions.

Downregulation of an immune response by modulating the interaction between RGMb and PD-L2 may also be useful in treating an autoimmune attack of autologous tissues. It is therefore within the scope of the invention to modulate conditions exacerbated by autoimmune attack, such as autoimmune disorders, as well as conditions such as heart disease, myocardial infarction, and atherosclerosis.

4. Upregulation of Immune Responses by Modulating RGMb/PD-L2 Interactions

Agents described herein can also be used to upregulate immune responses. In one embodiment, blockage of the interaction between RGMb and PD-L2 results in upregulation of an immune response. Upregulation of immune responses can be in the form of enhancing an existing immune response or eliciting an initial immune response. For instance, enhancing an immune response using the subject compositions and methods is useful in treating cancer, an infectious disease (e.g., bacteria, viruses, or parasites), a parasitic infection, asthma associated with impaired airway tolerance, a neurological disease, and an immunosuppressive disease.

Exemplary infectious disorders include viral skin diseases, such as Herpes or shingles, in which case such an agent can be delivered topically to the skin. In addition, systemic viral diseases, such as influenza, the common cold, and encephalitis might be alleviated by systemic administration of such agents. In one preferred embodiment, agents that upregulate the immune response described herein are useful for modulating the arginase/iNOS balance during

*Trypanosoma cruzi* infection in order to facilitate a protective immune response against the parasite.

Alternatively, immune responses can be enhanced in an infected patient through an ex vivo approach, for instance, by removing immune cells from the patient, contacting immune cells in vitro with an agent that modulate the interaction between RGMb and PD-L2 and reintroducing the in vitro stimulated immune cells into the patient.

In certain instances, it may be desirable to further administer other agents that upregulate immune responses, for example, forms of other B7 family members that transduce signals via costimulatory receptors, in order to further augment the immune response.

Agents that upregulate an immune response can be used prophylactically in vaccines against various polypeptides (e.g., polypeptides derived from pathogens). Immunity against a pathogen (e.g., a virus) can be induced by vaccinating with a viral protein along with an agent that upregulates an immune response, in an appropriate adjuvant.

In another embodiment, upregulation or enhancement of an immune response function, as described herein, is useful in the induction of tumor immunity.

In another embodiment, the immune response can be stimulated by the methods described herein, such that preexisting tolerance, clonal deletion, and/or exhaustion (e.g., T cell exhaustion) is overcome. For example, immune responses against antigens to which a subject cannot mount a significant immune response, e.g., to an autologous antigen, such as a tumor specific antigens can be induced by administering appropriate agents described herein that upregulate the immune response. In one embodiment, an autologous antigen, such as a tumor-specific antigen, can be coadministered. In another embodiment, an immune response can be stimulated against an antigen (e.g., an autologous antigen) to treat a neurological disorder. In another embodiment, the subject agents can be used as adjuvants to boost responses to foreign antigens in the process of active immunization.

In one embodiment, immune cells are obtained from a subject and cultured ex vivo in the presence of an agent as described herein, to expand the population of immune cells and/or to enhance immune cell activation. In a further embodiment the immune cells are then administered to a subject. Immune cells can be stimulated in vitro by, for example, providing to the immune cells a primary activation signal and a costimulatory signal, as is known in the art. Various agents can also be used to costimulate proliferation of immune cells. In one embodiment immune cells are cultured ex vivo according to the method described in PCT Application No. WO 94/29436. The costimulatory polypeptide can be soluble, attached to a cell membrane, or attached to a solid surface, such as a bead.

In still another embodiment, agents described herein useful for upregulating immune responses can further be linked, or operatively attached, to toxins using techniques that are known in the art, e.g., crosslinking or via recombinant DNA techniques. Such agents can result in cellular destruction of desired cells. In one embodiment, a toxin can be conjugated to an antibody, such as a bispecific antibody. Such antibodies are useful for targeting a specific cell population, e.g., using a marker found only on a certain type of cell, e.g., RGMb- and/or PD-L2-expressing cell. The preparation of immunotoxins is, in general, well known in the art (see, e.g., U.S. Pat. No. 4,340,535, and EP 44167). Numerous types of disulfide-bond containing linkers are known which can successfully be employed to conjugate the toxin moiety with a polypeptide. In one embodiment, linkers that contain a disulfide bond that is sterically "hindered" are preferred, due to their greater stability in vivo, thus preventing release of the toxin moiety prior to binding at the site of action. A wide variety of toxins are known that may be conjugated to polypeptides or antibodies of the invention. Examples include: numerous useful plant-, fungus- or even bacteria-derived toxins, which, by way of example, include various A chain toxins, particularly ricin A chain, ribosome inactivating proteins such as saporin or gelonin, α-sarcin, aspergillin, restrictocin, ribonucleases, such as placental ribonuclease, angiogenic, diphtheria toxin, and *Pseudomonas* exotoxin, etc. A preferred toxin moiety for use in connection with the invention is toxin A chain which has been treated to modify or remove carbohydrate residues, deglycosylated A chain. (U.S. Pat. No. 5,776,427). Infusion of one or a combination of such cytotoxic agents, (e.g., ricin fusions) into a patient may result in the death of immune cells.

V. Administration of Agents

The immune modulating agents of the invention are administered to subjects in a biologically compatible form suitable for pharmaceutical administration in vivo, to either enhance or suppress immune cell mediated immune responses. By "biologically compatible form suitable for administration in vivo" is meant a form of the protein to be administered in which any toxic effects are outweighed by the therapeutic effects of the protein. The term "subject" is intended to include living organisms in which an immune response can be elicited, e.g., mammals. Examples of subjects include humans, dogs, cats, mice, rats, and transgenic species thereof. Administration of an agent as described herein can be in any pharmacological form including a therapeutically active amount of an agent alone or in combination with a pharmaceutically acceptable carrier.

Administration of a therapeutically active amount of the therapeutic composition of the present invention is defined as an amount effective, at dosages and for periods of time necessary, to achieve the desired result. For example, a therapeutically active amount of an agent may vary according to factors such as the disease state, age, sex, and weight of the individual, and the ability of peptide to elicit a desired response in the individual. Dosage regimens can be adjusted to provide the optimum therapeutic response. For example, several divided doses can be administered daily or the dose can be proportionally reduced as indicated by the exigencies of the therapeutic situation.

The agents or the invention described herein can be administered in a convenient manner such as by injection (subcutaneous, intravenous, etc.), oral administration, inhalation, transdermal application, or rectal administration. Depending on the route of administration, the active compound can be coated in a material to protect the compound from the action of enzymes, acids and other natural conditions which may inactivate the compound. For example, for administration of agents, by other than parenteral administration, it may be desirable to coat the agent with, or co-administer the agent with, a material to prevent its inactivation.

An agent can be administered to an individual in an appropriate carrier, diluent or adjuvant, co-administered with enzyme inhibitors or in an appropriate carrier such as liposomes. Pharmaceutically acceptable diluents include saline and aqueous buffer solutions. Adjuvant is used in its broadest sense and includes any immune stimulating compound such as interferon. Adjuvants contemplated herein include resorcinols, non-ionic surfactants such as polyoxyethylene oleyl ether and n-hexadecyl polyethylene ether.

Enzyme inhibitors include pancreatic trypsin inhibitor, diisopropylfluorophosphate (DEEP) and trasylol. Liposomes include water-in-oil-in-water emulsions as well as conventional liposomes (Sterna et al. (1984) *J. Neuroimmunol.* 7:27).

The agent may also be administered parenterally or intraperitoneally. Dispersions can also be prepared in glycerol, liquid polyethylene glycols, and mixtures thereof, and in oils. Under ordinary conditions of storage and use, these preparations may contain a preservative to prevent the growth of microorganisms.

Pharmaceutical compositions of agents suitable for injectable use include sterile aqueous solutions (where water soluble) or dispersions and sterile powders for the extemporaneous preparation of sterile injectable solutions or dispersion. In all cases the composition will preferably be sterile and must be fluid to the extent that easy syringeability exists. It will preferably be stable under the conditions of manufacture and storage and preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it is preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating an agent of the invention (e.g., an antibody, peptide, fusion protein or small molecule) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the agent plus any additional desired ingredient from a previously sterile-filtered solution thereof.

When the agent is suitably protected, as described above, the protein can be orally administered, for example, with an inert diluent or an assimilable edible carrier. As used herein "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic compositions is contemplated. Supplementary active compounds can also be incorporated into the compositions.

It is especially advantageous to formulate parenteral compositions in dosage unit form for ease of administration and uniformity of dosage. "Dosage unit form", as used herein, refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by, and directly dependent on, (a) the unique characteristics of the active compound and the particular therapeutic effect to be achieved, and (b) the limitations inherent in the art of compounding such an active compound for the treatment of sensitivity in individuals.

In one embodiment, an agent of the invention is an antibody. As defined herein, a therapeutically effective amount of antibody (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an antibody can include a single treatment or, preferably, can include a series of treatments. In a preferred example, a subject is treated with antibody in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody used for treatment may increase or decrease over the course of a particular treatment. Changes in dosage may result from the results of diagnostic assays.

This invention is further illustrated by the following examples which should not be construed as limiting. The contents of all references, patents and published patent applications cited throughout this application, as well as the Figures, are incorporated herein by reference.

EXAMPLES

Example 1

Materials and Methods for Examples 2-12

A. Mice

Wild type (WT) BALB/cJ mice, BALB/cByJ mice and C57BL/6 mice were purchased from the Jackson Laboratory. PD-L2 KO mice on BALB/c background have been described (Keir et al. (2008) *Annu. Rev. Immunol.* 26:677-704). OVA TCR-transgenic DO11.10 mice were used as donors of OVA-specific CD4+ T cells (Tsitoura el al. (1999) *J. Immunol.* 163:2592-2600). Age-matched female mice were used at 6-12 weeks. Animal protocols were approved by The Animal Care and Use Committees at Boston Children's Hospital, the Dana-Farber Cancer Institute, and Harvard Medical School.

B. Cells and Culture Media

Mouse pre-B cell line 300 cells were transfected by electroporation with mRGMb or hRGMb cDNA in the pEFGF-Puro expression vector. Cells were selected in media containing puromycin, sorted, and subcloned. Cell-surface expression of mRGMb and hRGMb was verified by flow cytometry using an mRGMb polyclonal antibody (R&D) and an hRGMb mAb (R&D), respectively. Other transfected cells, such as 300-mPD-L2, 300-mPDL 1, 300-mPD-1, and Jurkat-hPD-1, have been made previously using the same method. Cells were cultured in RPMI-1640 (Mediatech) supplemented with 10% heat-inactivated FBS (Invitrogen), 1% streptomycin/penicillin, 15 μg/ml gentamicin (Invitrogen), 1% glutamax (Invitrogen), and 50 μM β-mercaptoethanol (Sigma-Aldrich) at 37° C. with 5% $CO_2$.

The cell lines used herein were purchased from American Type Culture Collection (ATCC), except for SN12C which was obtained from the National Cancer Institute (NCI).

Mouse spleen or LN cells for tolerance experiments were cultured in high-glucose DMEM (Invitrogen) supplemented with 10% FBS, 1% glutamax, 50 μM β-mercaptoethanol at 37° C. in a 10% $CO_2$ incubator.

C. COS Cell Expression Cloning of RGMb

A panel of murine activated lymphocyte cDNA expression libraries were transiently transfected into COS cells using DEAE-Dextran or Lipofectamine as facilitator (Freeman et al. (1989) *J. Immunol.* 143:2714-2722). After 44 hours, COS cells were harvested and panned on mPD-L2-mIgG2a/IgA coated petri plates. Episomal DNA was recovered and electroporated into *E. coli* DH10B/P3. Spheroplast fusion was used to reintroduce the plasmids into COS cells for subsequent rounds of expression and panning. Before the second and third rounds, COS cells expressing PD-1 were removed by incubating with PD-1 mAb followed by depletion with goat anti-rat IgG magnetic beads. After the third round of panning, individual plasmids were transfected into COS cells and binding of PD-L2-Ig to RGMb was verified by flow cytometry on mRGMb transiently transfected COS cells. At least four independent mRGMb cDNA clones were isolated.

D. Generation of Antibodies

Rats were immunized 3 times via intramuscular and intravenous injection of mRGMb plasmid cDNA (Latchman et al. (2001) *Nat. Immunol.* 2:261-268), and boosted 3 times with recombinant mRGMb-HIS (R&D) via i.p. and s.c. injection. Hybridoma supernatants were screened by flow cytometry on mRGMb transfected 300 cells or ELISA on plates coated with recombinant mRGMb (R&D). Hybridomas were subcloned to stability and antibodies were purified from culture supernatants by protein G affinity chromatography, and verified to have endotoxin levels less than 2 EU/mg protein. Clones 307.9D1 (rat IgG2a) and 307.1H6 (rat IgG2a) were selected for use in the Examples described herein. In addition, Table 2 provides a summary of the blocking capacities of various mRGMb and mPD-L2 monoclonal antibodies.

TABLE 2

Blocking capacities of mRGMb and mPD-L2 mAbs

| Antibodies | mRGMb to mPD-L2 | mPD-L2 to mPD-1 | mRGMb to mBMP-2/4 |
|---|---|---|---|
| mRGMb mAbs | | | |
| 307.9D1, 307.8B2 | Yes | N.A. | Yes |
| 307.1H6, 307.9D3, 307.5G1 | No | N.A. | No |
| mPD-L2 mAbs | | | |
| GF17.2C9 | Yes | No | N.A. |
| 3.2. TY25 | Yes | Yes | N.A. |

N.A.: Not applicable

Finally, Table 3 provides sequences for the isolated rat anti-mouse/anti-human RGMb 9D1 monoclonal antibody. Briefly, the variable domain of the light and heavy chains of the 9D1 mAb have been sequenced and the complementarity determining regions (CDR) domains thereof are provided. Numbering is shown according to nucleic acid positions and the corresponding amino acid residues, corresponding to CDRs, for example, can easily be identified based on the provided translations.

TABLE 3

9D1 mAb sequences

9D1 Light Chain Variable (vK) DNA and Amino Acid Seqences

```
Locus 9D1_LS-VK 378 bp DNA linear
DEFINITION 9D1, DNA 378 bases.
FEATURES    Location/Qualifiers
J_segment   348 . . . 378
            /label = JK
V_segment   325 . . . 348
            /label = CDR3
V_region    229. . . 324
            /label = FWR3
V_segment   208 . . . 228
            /label = CDR2
V_region    163 . . . 207
            /label = FWR2
V_segment   130 . . . 162
            /label = CDR1
V_region    61 . . . 129
            /label = FWR1
sig_peptide 1. . . 60
            /vntifkey = "94"
            /label = LS
CDS         1 . . . 378
            /label = 9D1\LS-VK
/translation = "MMAAVQLLGLLLLCLRAMRCDIQMTQSPSHLSASVGDRVT

LSCKVSQNIYKYLNWYQQKLGEAPKLLIYYTSFLQTGIPSRFSGSGSGTDYTLT

ISSLQPEDVATYFCQKYYSGWTFGGGTKLELK"  (SEQ ID NO: 12)

BASE COUNT      103 a       91 c       89 g        95 t
ORIGIN
```

TABLE 3-continued

| 9D1 mAb sequences |
|---|
| (SEQ ID NO: 11)<br>1 atgatggctg cagttcagct cttagggctt ttgctgctct gcctccgagc catgagatgt<br>61 gacatccaga tgacccagtc tccttcacac ctgtcagcat ctgtgggaga cagagtcact<br>121 ctcagctgca aagtaagtca gaatatttac aagtacttaa actggtatca gcaaaaactt<br>181 ggagaagctc ccaaactcct gatatattat acaagctttt tgcaaacggg catcccgtca<br>241 aggttcagtg gcagtggatc tggtacagat tacacactca ccatcagcag cctgcagcct<br>301 gaagatgttg ccacatattt ctgccagaag tattatagcg ggtggacgtt cggtggaggc<br>361 accaagctgg aattgaaa |
| 9D1 Heavy Chain Variable DNA and Amino Acid Sequences |
| LOCUS 9D1_LS-VH 408 bp DNA linear<br>DEFINITION 9D1, DNA 408 bases.<br>FEATURES Location/Qualifiers<br>J_segment 376 . . . 408<br>/label = JH<br>V_segment 352 . . . 375<br>/label = CDR3<br>V_region 256. . . 351<br>/label = FWR3<br>V_segment 205 . . . 255<br>/label = CDR2<br>V_region 163 . . . 204<br>/label = FWR2<br>V_segment 148 . . . 162<br>/label = CDR1<br>V_region 88 . . . 147<br>/label = FWR1<br>sig_peptide 1. . . 87<br>/label = LS<br>CDS 1 . . . 408<br>/label = 9D1\LS-VH<br>/translation = "MGWSQIILFLVAATTCVHSQVQLQQSGTELVKPGSSVKIS<br>CKASGDTFTSDYMHWIRQQPGSGLEWIGWIYPGNGNTKYNQKFDGKATLTADKS<br>SSTAYLQLSLLTSEDYAVYFCARQTEGYFDYWGQGVMTVSS" (SEQ ID NO: 14)<br>BASE COUNT 107 a 97 c 106 g 98 t<br>ORIGIN<br>(SEQ ID NO: 13)<br>1 atgggatgga gccagatcat tctctttctg gtggcagcaa ctacatgtgt ccactcccag<br>61 gtacagctac agcaatcagg gactgaactg gtgaagcctg ggtcctcagt gaaaatttcc<br>121 tgcaaggctt ctggcgacac cttcaccagt gactatatgc actggataag gcagcagcct<br>181 ggaagtggcc ttgagtggat tgggtggatt tatcctggaa atggtaatac taagtacaat<br>241 caaaagttcg atgggaaggc aacactcact gcagacaaat cctccagcac agcctatttg<br>301 cagctcagcc tcctgacatc tgaggactat gcagtctatt tctgtgcaag acagacggag<br>361 gggtactttg attactgggg ccaaggagtc atggtcacag tctcctca |

E. Generation of Ig Fusion Proteins mRGMb-Ig fusion proteins were generated by joining the extracellular domain of mRGMb to the Fc portion of mouse IgG2a protein, mutated to reduce FcR binding (Latchman et al. (2001) *Nat. Immunol.* 2:261-268). mPD-L2-hIgG1/IgA fusion proteins 50 were generated by joining the extracellular domain of PD-L2 with the Fc portion of hIgG1 and the tail piece of hIgA. Fc fusion proteins were purified from CHO cell culture supernatants by protein A or protein G affinity chromatography and verified to have endotoxin levels less than 2 EU/mg protein. Other Ig fusion proteins used have been described previously (Latchman et al. (2001) *Nat. Immunol.* 2:261-268).

F. Cell Conjugation Assay

An assay for receptor-ligand binding was developed based on cell to cell binding as determined by flow cytometry. One transfected cell type was labelled with the red dye PKH26 (Sigma) and the other transfected cell with the green dye PKH67 (Sigma) according to the manufacturer's instructions. Red dye-labelled and green dye-labelled cells (105 each cell type) were incubated in 200 μl of HBSS buffer without calcium and magnesium (GIBCO) supplemented with 10% heat-inactivated FBS (Invitrogen), 15 μg/ml gentamicin (Invitrogen) and 1% HEPES (Invitrogen) in a round bottom 96-well plate for 45 min at 37° C. When the cell conjugation assay was used to test the blocking capacity of antibodies, one transfected cell type was pre-incubated 30 min at RT with antibodies before adding the other type of transfected cells. Conjugate formation was analyzed immediately by flow cytometry using the PE channel for the red dye and the FITC channel for the green dye. The automated plate harvester of the FACSCanto (BD Biosciences) was used for uniformity of cell processing. The instrument settings were as follows, throughput mode: standard, loader settings: sample flow rate at 0.5 μl/second, sample volume and mixing volume at 100 μl, mixing speed at 50 μl/second, number of mixes at 2, and wash volume at 400 μl.

G. Flow Cytometry

Cells were stained with target antibodies and isotype controls using standard flow cytometry procedures, and analyzed on a FACSCanto (BD Biosciences) and FlowJo 9.2 software (TreeStar).

To initially verify RGMb expression on mRGMb or hRGMb transfected cells, sheep anti-mRGMb (R&D) or sheep IgG (SouthernBiotech) plus donkey anti-sheep IgG-PE (Jackson ImmunoResearch Laboratories) and mouse anti-hRGMb (mAb, R&D) plus goat anti-mouse IgG-PE (SouthernBiotech) were used, respectively, all at 10 g/ml.

To test the binding specificities of mRGMb antibodies, mRGMb or hRGMb transfected 300 cells were incubated with serial dilutions of sera, culture supernatants or purified antibodies, then binding was detected with 5 μg/ml of goat anti-rat IgG-PE (SouthernBiotech). For biotin-conjugated mRGMb mAb 9D1, 1.4 μg/ml of streptavidin-PE was used.

For receptor-ligand binding assay, mRGMb or hRGMb transfected 300 cells and control cells (300 cells and hPD-1 transfected Jurkat T cells) were stained with serial dilutions of mPD-L2-hIgG1/gA or control-hIgG1/IgA plus 5 μg/ml of Fab2 goat anti-hIgG-PE (mouse-absorbed, SouthernBiotech), or with serial dilutions of mPD-L1-mIgG2a or control-mIgG2a plus 10 μg/ml of goat anti-mIgG2a-PE (SouthernBiotech). mPD-L2 transfected 300 cells and 300 cells were stained with serial dilutions of mRGMb-mIgG2a or control-mIgG2a plus 5 μg/ml of Fab2 goat anti-mIgG2a-PE (SouthernBiotech).

To assess cell surface expression of RGMb and PD-L2 on mouse cell lines RAW264.7, J774.1 and C2C12, PE-conjugated mRGMb mAb 9D1, mPD-L2 mAb TY25 or rat IgG2a at 5 μg/ml were used; RAW264.7 and J774.1 cell lines were preincubated with mouse Fe receptor mAb (2.4 G2).

To analyze cell surface expression of RGMb on human cancer cell lines, mRGMb mAb 1H6 or rat IgG2a at 10 μg/ml plus goat anti-rat IgG-PE (SouthernBiotech) at 5 μg/ml were used.

For intracellular flow cytometry analyses of RGMb expression in primary cells from spleen, thymus, and lung, cells were first stained with LIVE/DEAD® Fixable Near-IR (Invitrogen) at 1:1000. After preincubation with mouse Fe receptor mAb (2.4 G2), cells were stained for surface markers with different combinations of the following antibodies (BioLegend): CD3-Pacific Blue, CD4-PE-cy7, CD8-allophycocyanin (APC), CD19-PE-cy7, CD11c-APC and F4/80-APC. Then cells were permeabilized using BD Cytofix/Cytoperm™ Fixation/Permeabilization Kit. PBS containing 3% BSA and 0.1% Triton X-100 was used for wash and antibody incubation in the following procedures. If biotin-conjugated antibodies were used, endogenous biotin was blocked with Endogenous Biotin-Blocking kit (Molecular Probes), according to the manufacturer's instruction. Cells were stained with PE-conjugated mRGMb mAb 9D1 or rat IgG2a at 5 μg/ml, or biotin-conjugated mRGMb mAb 9D1 or rat IgG2a at 2.5 μg/ml plus streptavidin-PE or -APC (BD Biosciences) at 1 μg/ml after preincubation with mouse Fe receptor mAb (2.4 G2) and hIgG (Jackson ImmunoResearch Laboratories). For Foxp3 staining, eBioscience Foxp3 Fixation/Permeabilization reagents and Foxp3-PE (BioLegend) were used. 300 cells and mPD-L2 transfected 300 cells were used as negative controls.

DO11.10 T cells were identified by staining with TCRβ-APC-eFluor 780, CD4-PerCP and KJ1-26-APC (eBioscience). DO11.10 Treg cells were identified using CD25-FITC (BioLegend), followed by intracellular staining with Foxp3-PE as described above.

H. ELISA

To examine specificity of mRGMb mAbs, 96-well plates were coated with 2 μg/ml of recombinant mRGMa-HIS, mRGMb-HIS, or mRGMc-HIS (R&D). Then, serial dilutions of mRGMb mAbs and isotype controls were added and incubated for 1 hour (h) at 37° C. Mouse anti-rat IgG (γ-specific)-HRP (Jackson ImmunoResearch Laboratories) at 1:2500 was used for detection.

To examine RGMa/RGMb/RGMc and PD-L2 interaction, 96-well ELISA plates were coated with 2 or 5 μg/ml of recombinant mRGMa-HIS, mRGMb-HIS, mRGMc-HIS, or hRGMb-HIS (R&D). Then, serial dilutions of mPD-L2-hIgG1/IgA, mPD-L2-mIgG2a/IgA, hPD-L2-mIgG2a or control-Ig fusion proteins were added and incubated for 1h at 37° C. $Fab_2$ goat anti-hIgG-HRP (Jackson ImmunoResearch Laboratories) or rat anti-mIgG2a-HRP (BD Biosciences) at 1:1000 or 1:10000 were used for detection.

To test the capacities of mRGMb antibodies and mPD-L2 fusion proteins to block RGMb binding to BMP-2/4, 96-well ELISA plates were coated with 1 μg/ml of recombinant mouse BMP-2 (GIBCO) or BMP-4 (R&D). mRGMb antibodies, isotype controls, mPD-L2-hIgG1/IgA, mPD-L2-mIgG2a/IgA, or control Ig fusion proteins at the indicated concentrations were preincubated with 20 μg/ml mRGMb-HIS (R&D) for 45 min. at 4° C., then added to the plates and incubated for 1h at 37° C. Anti-penta-HIS-HRP (Qiagen) at 1:1000 was used for detection.

To determine if RGMb binds PD-L2 and BMP-2/4 simultaneously, 96-well ELISA plates were coated with BMP-2/4 as above. mPD-L2-hIgG1/IgA, mPD-L2-hIgG (R&D), mPD-L1-hIgG (R&D) or control-Ig fusion proteins at 10 μg/ml were preincubated with 10 μg/ml mRGMb-HIS (R&D) or buffer alone for 15 min. at room temperature (RT), then added to the plates and incubated for 1h at 37° C. Alternatively, 10 μg/ml mRGMb-HIS (R&D) or buffer alone was added first to the plates and incubated for 1h at 37° C. After wash, mPD-L2-Ig or control-Ig fusion proteins were added and incubated for 1h at 37° C. $Fab_2$ goat anti-hIgG-HRP (Jackson ImmunoResearch Laboratories) at 1:10000 was used for detection.

The substrate for HRP was TMB microwell peroxidase substrate system (KPL).

I. Cell Isolation and Stimulation

Spleen and thymus cells were isolated by mechanically disrupting the tissues. Splenocytes were treated with red blood cell lysing buffer (Sigma).

To obtain lung cells for flow cytometry and western blotting or to analyze splenic DCs, lung or spleen tissue pieces were digested in RPMI 1640 with 5% FBS, 1 mg/ml collagenase IV (Sigma) and 200 U/ml DNase I (Roche) and then treated with red blood cell lysing buffer (Sigma).

Lung alveolar macrophages and interstitial macrophages for Western blot analysis were sorted by flow cytometry based on their differential expression of F4/80 and CD11c (F4/80+CD11c+ for alveolar macrophages and F4/80+ CD11c− for interstitial macrophages), as described previously in Bedoret et al. (2009) *J. Clin. Invest.* 119:3723-3738.

Thioglycollate-induced peritoneal macrophages for Western blotting were obtained from BALB/c mice on day 4 after i.p. injection with 3% thioglycollate (DIFCO).

CD4+ and CD8+ cells for Western blotting were purified from mouse splenocytes by using CD4+ T cell isolation kit and CD8+ T cell isolation kit (Miltenyi Biotec Inc.).

FLT-3L stimulated splenocytes were obtained from mice 2 weeks after s.c. injection of FLT-3L-transfected RENCA tumor line.

Activated T cells were prepared by stimulating splenocytes or thymocytes with plate-coated CD3 mAb 2C11 (BD Biosciences) at 10 μg/ml and/or soluble CD28 mAb 37.51 (BD Biosciences) at 1 μg/ml for 6 days, then washed and restimulated with plate-coated CD3 mAb (10 μg/ml) alone or together with soluble CD28 mAb (1 μg/ml) for 2 days. Cells on days 1 and 3 after primary stimulation and day 2 after secondary stimulation were analyzed by Taqman real-time RT-PCR or flow cytometry.

J. Taqman Real-Time RT-PCR

Total RNA samples were isolated using the RNeasy mini kit (QIAGEN). Reverse transcription was performed using the Quantitect reverse transcription kit (QIAGEN). Taqman gene expression assays (Applied Biosystems) for mRGMb (Mm00724273_m1), mPD-L2 (Mm00451734_m1), mPD-1 (Mm00435532_m1) and the endogenous control mouse GAPDH (Mm99999915_g1) were used in real-time PCR carried out in a 7300 Real-Time PCR system (Applied Biosystems). Fold change compared with GAPDH was calculated using the ΔCt method.

K. Western Blotting

Cell lysates were prepared using RIPA buffer with cOmplete ULTRA protein inhibitors tablets (Roche). Lysates (60-80 pig/lane for cell lines and primary cells and 0.5 or 1 μg/lane for RGMb transfected 300 cells) were run on SDS-PAGE under reducing conditions and Western blotting was carried out using rat mRGMb mAb 1H6 (10 μg/ml) plus goat anti-rat IgG-HRP (Santa Cruz Biotechnology) (1:5000). To blot the loading control, the membranes were treated with Restore Plus Western Blot Stripping Buffer (Thermo Scientific) and blotted with mouse anti-mouse β-actin (Abcam) (1:5000) plus goat anti-mouse IgG-HRP (Santa Cruz Biotechnology) (1:4000). Protein bands on the membranes were visualized using standard chemiluminescent techniques.

L. Immunohistochemistry Staining and Confocal Microscopy

Cells were seeded on coverslips in culture medium the day before staining. Cells were washed twice with PBS and fixed with 3.7% formaldehyde for 15 mins. at room temperature. After three washes with PBS containing 0.5% BSA, cells were permeabilized in PBS containing 0.5% BSA and 0.5% Triton X-100 for 30 mins. Endogenous biotin was blocked with Endogenous Biotin-Blocking kit (Molecular Probes), according to the manufacturer's instruction, followed by blocking in PBS containing 3% BSA and 0.1% Triton X-100 for 30 mins. at room temperature and three washes in PBS containing 0.5% BSA and 0.1% Triton X-100. Cells were then incubated with biotinconjugated mRGMb mAb 1H6 or biotin-conjugated rat IgG2a at 0.5 μg/ml in PBS containing 1% BSA and 0.1% Triton X-100 for two hours at room temperature, followed by three washes as above. Subsequently, cells were incubated with Alexa Fluor 488-conjugated streptavidin (Jackson ImmunoResearch Laboratories) at 0.5 μg/ml in PBS containing 1% BSA and 0.1% Triton X-100 for one hour at room temperature, followed by three washes as above. Finally, cells were stained with Phalloidin-TRIC (Sigma) at 50 μg/ml to label F-actin, and coverslips were mounted on slides with mounting media. Images were taken using a Nikon D-Eclipse C1 confocal microscope equipped with a Melles Griot 488 Ion Laser (with a 515/30 emission filter), a Melles Griot 543 Laser (with a 590/50 emission filter), a Melles Griot 640 Laser and the Confocal Acquisition Software Nikon EZ-C1 version 3.90.

M. Respiratory Tolerance and mAb Treatment

To induce tolerance, lightly anesthetized WT BALB/cByJ or PD-L2−/− mice received 100 μg of LPS-free OVA (Worthington Biochemical) in PBS or PBS alone (control) by intranasal instillation on days 0, 1, and 2. In some experiments, mice were treated with RGMb, PD-L2, PD-L1, or PD-1 blocking mAb or control antibody i.p. on day −1 (400 μg/mouse) and day 2 (200 μg/mouse). On day 12, mice were immunized with 50 μg OVA (ICN Biomedical) adsorbed in 2 mg alum. Spleens were harvested on day 19 and splenocytes or B-depleted splenocytes (FIG. 8D) were restimulated in vitro with OVA. Cultures were pulsed with 1 μCi of 3H-thymidine for the final 17 hrs and harvested at 96 hrs. Culture supernatants were harvested at 96 hrs. for IL-4 ELISA.

N. Transfer of DO11.10 T Cells and Respiratory Tolerance

DO11.10 T cells were positively selected from the spleens of DO11.10 Tg mice by incubating with CD4+ magnetic beads and sorting using MACS columns (Miltenyi Biotec Inc.). Each recipient received $2\times10^5$ or $5\times10^6$ DO11.10 T cells i.v., followed by three intranasal doses of 100 μg LPS-free OVA on days 0, 1, 2 and mAbs as indicated. Cells from mediastinal LNs were analyzed by flow cytometry on days 3, 5, or 7.

O. Statistical Analysis

Two-tailed Student's t-test and two-way ANOVA followed by Tukey's or Dunnett's multiple comparisons test were performed using GraphPad Prism version 6.00 for MacOS X, GraphPad Software, La Jolla Calif. USA (available on the World Wide Web at graphpad.com. $p<0.05$ was considered as significant. Data are mean±SEM.

Example 2

RGMb Binds to PD-L2, but not to PD-L1 or Other Related Molecules

RGMb, also known as DRAGON, is a member of the RGM family which consists of RGMa, RGMb and RGMc/hemojuvelin (Severyn et al. (2009) *Biochem J.* 422:393-403). RGMs are glycosylphosphatidylinositol (gpi)-anchored membrane proteins that bind bone morphogenic proteins (BMPs) and neogenin (Conrad et al. (2010) *Mol. Cell Neurosci.* 43:222-231). BMPs consist of a family with more than 20 members related to the transforming growth factor-β (TGF-β) family (Bragdon et al. (2011) *Cell Signal.* 23:609-620 and Yoshioka et al. (2012) *Eur. J. Immunol.* 42:749-759). RGMb directly binds to BMP-2 or BMP-4, which in turn bind to type I receptors (ALK1, ALK2, ALK3, and ALK6) and type II receptors (BMPRII, ActRIIa and ActRIIb) (Corradini et al. (2009) *Cytokine Growth Factor Rev.* 20:389-398 and Yoshioka et al. (2012) *Eur. J. Immunol.* 42:749-759). RGMs coordinate utilization of specific BMP receptors (Corradini et al. (2009) *Cytokine Growth Factor Rev.* 20:389-398). RGMs do not directly signal but can act as co-receptors (e.g., RGMb binds directly to BMP-2/4) that modulate BMP signaling (Samad et al. (2005) *J. Biol. Chem.* 280:14122-14129).

RGMb is expressed and functions in the nervous system (Severyn et al., 2009). In addition, RGMb expression is observed in macrophages and other cells of the immune system (Xia et al., 2010). A role for RGMb in the immune system is only beginning to emerge (Galligan et al., 2007; Xia et al., 2010). RGMb deficient mice have an early lethal phenotype.

Thus, it was determined whether PD-L1 interacts with RGMb. Cells of the "300.19 cell" type transfected with mouse RGMb (mRGMb), also referred to as "300-mRGMb cells," express RGMb protein and are able to bind to mPD-L2-Ig fusion proteins, but not to mPD-L1-Ig fusion protein or other B7-family related Ig fusion proteins, as determined by flow cytometry analysis (FIGS. 1A-1C). Similarly. mPD-L2 transfected cells also bind to mRGMb-Ig fusion protein (FIGS. 1D-1E). Cells of the 300 cell type transfected with human RGMb (hRGMb) also bind to mPD-L2 Ig fusion protein (FIGS. 1F-1G).

Enzyme-linked immunosorbent assay (ELISA) analyses further demonstrated that mRGMb binds to mPD-L2 and hPD-L2, and that hRgmb binds to hPD-L2 and mPD-L2 (FIGS. 1H-1I). Thus, the RGMb:PD-L2 interaction occurs in both mice and humans. ELISA results also show that mPD-L2 binds to mRGMb, but not to mRGMa or mRGMc (FIG. 1J).

To test the RGMb:PD-L2 interaction under more physiologic conditions, a cell conjugation assay was used where one transfected cell type was labeled with a red dye and the other transfected cell type with a green dye. The binding of the two cell types was assessed by flow cytometry and indicated by double positive events (yellow dots). In FIGS. 1K, 1M, 1O, and 1Q, the upper panel shows the FSC-SSC plots and the lower panel shows the corresponding dot plots. FIGS. 1L, 1N, 1P, and 1R show only the dot plots without corresponding FSC-SSC plots. As expected, mRGMb cells bound to mPD-L2 cells (FIG. 1K), but not mPD-L1 cells (FIG. 1L). As positive controls, mPD-1 cells bound to both mPD-L2 and mPD-L1 cells (FIGS. 1M-1N). Negative control binding assays had very few conjugates (<0.3%) (FIGS. 1O-1R). These results show that RGMb binds specifically to PD-L2, but not to PD-L1, and the structural orientation is compatible with RGMb and PD-L2 cell surface to cell surface binding.

Example 3

Anti-RGMb Monoclonal Antibodies Bind to RGMb, but not to RGMa or RGMc

Flow cytometry analysis shows that the anti-mRGMb antibodies that were generated (e.g., clones 9D1, 1H6, 8B2, 9D3, 5G1, and 7A7) bind to mRGMb- or hRGMb-transfected 300 cells (see, for example, FIGS. 2A-2F). ELISA data show that anti-mRGMb antibodies bind to mRGMb, but not to mRGMa or mRGMc (FIG. 2G).

Example 4

Blocking Capacities of Anti-RGMb Antibodies, Anti-PD-L2 Antibodies, RGMb-Ig and PD-1-Ig Fusion Proteins A cell conjugation assay was used to test the blocking abilities of antibodies and fusion proteins. FIGS. 3A, 3B, and 3D show that 300-mRGMb cells were able to bind to 300-mPD-L2 cells, whereas FIGS. 3C and 3E show that 300-mPD-1 cells were able to bind to 300-mPD-L2 cells.

Figure 3:
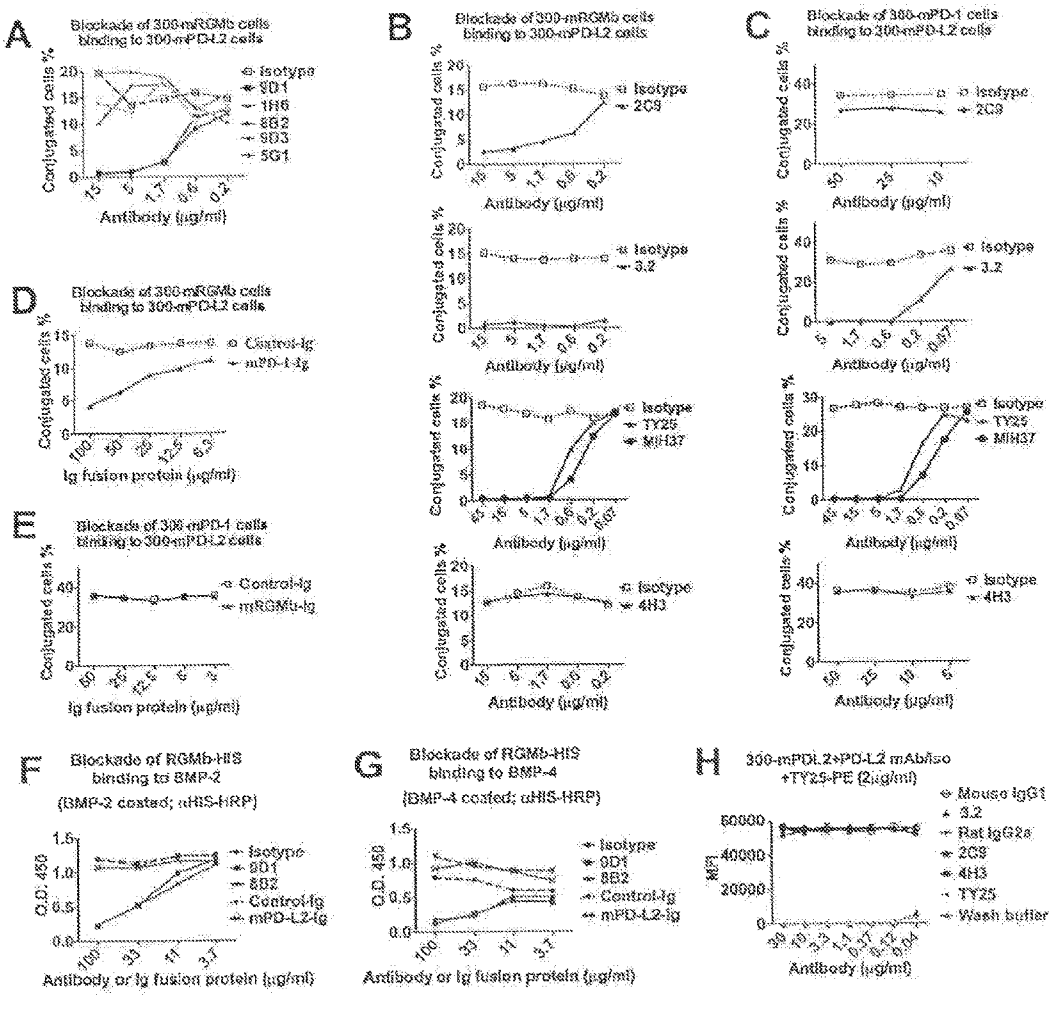
FIG. 3A-3H show the blocking capacities of anti-RGMb antibodies, anti-PD-L2 antibodies, RGMb-Ig and PD-1-Ig fusion proteins.

FIG. 3A shows the blocking capacities of exemplary anti-mRGMb antibodies. In particular, anti-mRGMb antibodies 9D1 and 8B2 blocked mRGMb binding to mPD-L2, whereas anti-mRGMb antibodies 1H6, 9D3 and 5G1 did not block mRGMb binding to mPD-L2.

FIGS. 3B and 3C show the blocking capacities of anti-PD-L2 antibodies. Specifically, anti-PD-L2 antibody 2C9 blocked mRGMb binding to mPD-L2, but not mPD-1 binding to mPD-L2. By contrast, anti-PD-L2 antibodies 3.2, TY25 and M1H37 blocked both mRGMb binding to mPD-L2 and mPD-1 binding to mPD-L2. Finally, anti-PD-L2 antibody 4H3 blocked neither mRGMb binding to mPD-L2 nor mPD-1 binding to mPD-L2. The existence of single and double blocker PD-L2 mAbs indicates that the PD-1 and RGMb binding sites on PD-L2 are close but distinct.

FIGS. 3D and 3E show that mPD-1-Ig reduced mRGMb binding to mPD-L2, whereas mRGMb-Ig had no effect on mPD-1 binding to mPD-L2. This result indicates that the binding of RGMb to PD-L2 is weaker than that of PD-1 to PD-L2.

Since RGMb binds directly to BMP-2/4, the capacity of the RGMb antibodies to block RGMb binding to BMP-2/4 was analyzed. 9D1 and 8B2 blocked RGMb binding to BMP-2/4 in an ELISA (FIGS. 3F-3G) and thus are dual blockers of RGMb interaction with PD-L2 and BMP. However, PD-L2-Ig fusion protein could not block RGMb binding to BMP-2/4 in an ELISA (FIG. 3F-3G). These data indicate that the binding sites on RGMb for PD-L2 and BMP are close but distinct.

It was also determined whether the single blocker anti-PD-L2 antibody 2C9 binds to a different epitope from the double-blockers. Flow cytometry data show that anti-mPD-L2 antibody 3.2 blocked anti-mPD-L2 antibody TY25-PE binding to 300-mPD-L2 cells, while anti-mPD-L2 antibodies 2C9 and 4H3 did not. These results indicate that 3.2 and TY25 share the same epitope while 2C9 and 4H3 recognize different epitopes from TY25.

Example 5

PD-L2 and BMP-2/4 Bind to Close but Distinct Sites on RGMb and Both can Bind Simultaneously to RGMb To test if RGMb can bind both PD-L2 and BMP at the same time, an ELISA was performed to analyze the binding capacity of PD-L2-Ig fusion protein to immobilized BMP-2/4 in the presence or absence of RGMb. PD-L2 could not directly bind to BMP-2/4, but in the presence of RGMb could form a complex with BMP when RGMb and PD-L2-Ig were added simultaneously (FIG. 4A-4B) or sequentially to BMP-2/4. These data are consistent with RGMb having distinct sites for PD-L2 and BMP binding and show that RGMb has the capacity to form a trimeric complex with BMP and PD-L2.

Figure 4:
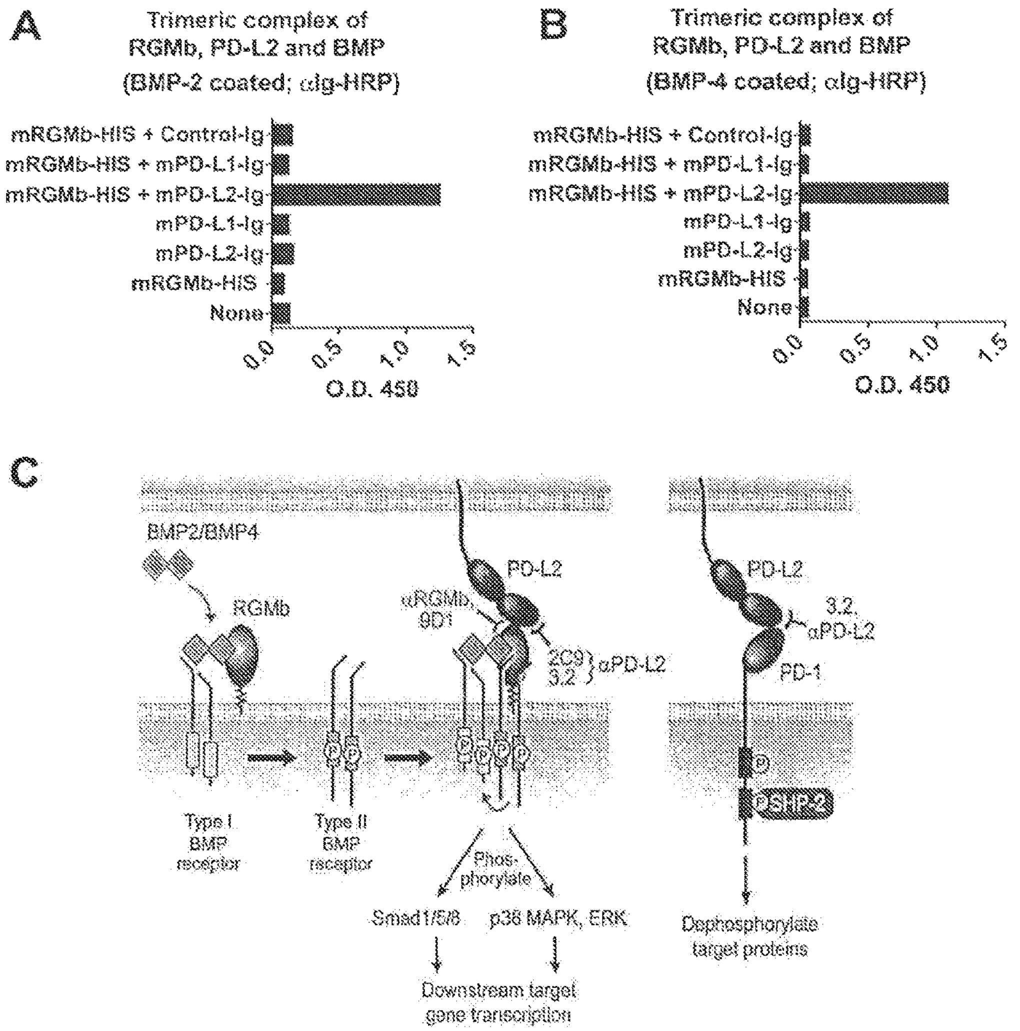
FIGS. 4A-4C show that PD-L2 and BMP-2/4 bind to close but distinct sites on RGMb and both can bind simultaneously to RGMb and a model for RGMb:PD-L2 interaction was proposed.

These data fit with results from other studies, including Corradini et al. (2009) *Cytokine Growth Factor Rev.* 20:389-98 and Yoshioka et al. (2012) *Eur. J. Immunol.* 42:749-59), in which it is proposed herein that a signaling complex exists involving the interactions of RGMb, PD-L2, BMP-2/4 and type I and type II BMP receptors (FIG. 4C, left panel). BMP-2 or BMP-4 dimers link RGMb to type I BMP receptors, which then recruit type II BMP receptors that phosphorylate the type I BMP receptors in a signaling complex. The complex phosphorylates Smad1/5/8 or p38 mitogen activated protein kinase (MAPK) and extracellular signal-regulated protein kinase (ERK), leading to downstream target gene transcription. The right panel of FIG. 4C shows PD-L2 binding to PD-1 which results in tyrosine phosphorylation of the PD-1 cytoplasmic domain, recruitment of tyrosine phosphatases, particularly SHP-2, and attenuation of antigen receptor signals. Thus, PD-L2, which can bind to either PD-1 or RGMb, can participate in two important signaling circuits, the PD-1 and BMP signaling pathways.

Example 6

RGMb Expression in Mouse Macrophages and the RGMb Protein Structure

RGMb mRNA has been reported in mouse lung macrophages, macrophage cell line RAW264.7 and myoblast cell line C2C12 (Xia et al. (2010) J. Immunol. 186:1369-1376), but protein expression was not determined. RGMb mRNA expression was confirmed in mouse macrophage cell lines RAW264.7 and J774.1 cells using real-time RT-PCR (FIG. 5A) and cell surface expression of RGMb protein was shown on these cell lines by flow cytometry using RGMb mAb 9D1 (FIG. 5B).

RGMb protein expression was also confirmed by Western blotting using RGMb mAb 1H6. One major band (~37KD) and one minor band (~49 Kilodaltons (kD)) were detected in RAW264.7, J774.1 and C2C12 cells, as well as in mRGMb-transfected 300 cells (FIGS. 5C-5D). No such bands were observed in 300 cells (FIG. 5C), consistent with the absence of RGMb mRNA (FIG. 5A). Western blotting demonstrated RGMb expression in mouse peritoneal macrophages and thioglycollate-induced peritoneal macrophages (FIG. 5E), as well as in lung alveolar and interstitial macrophages (FIG. 5F). The 1H6 mAb also detected human RGMb by Western blotting in hRGMb-transfected 300 cells and human Jurkat T cells (FIG. 5C).

Figure 5:
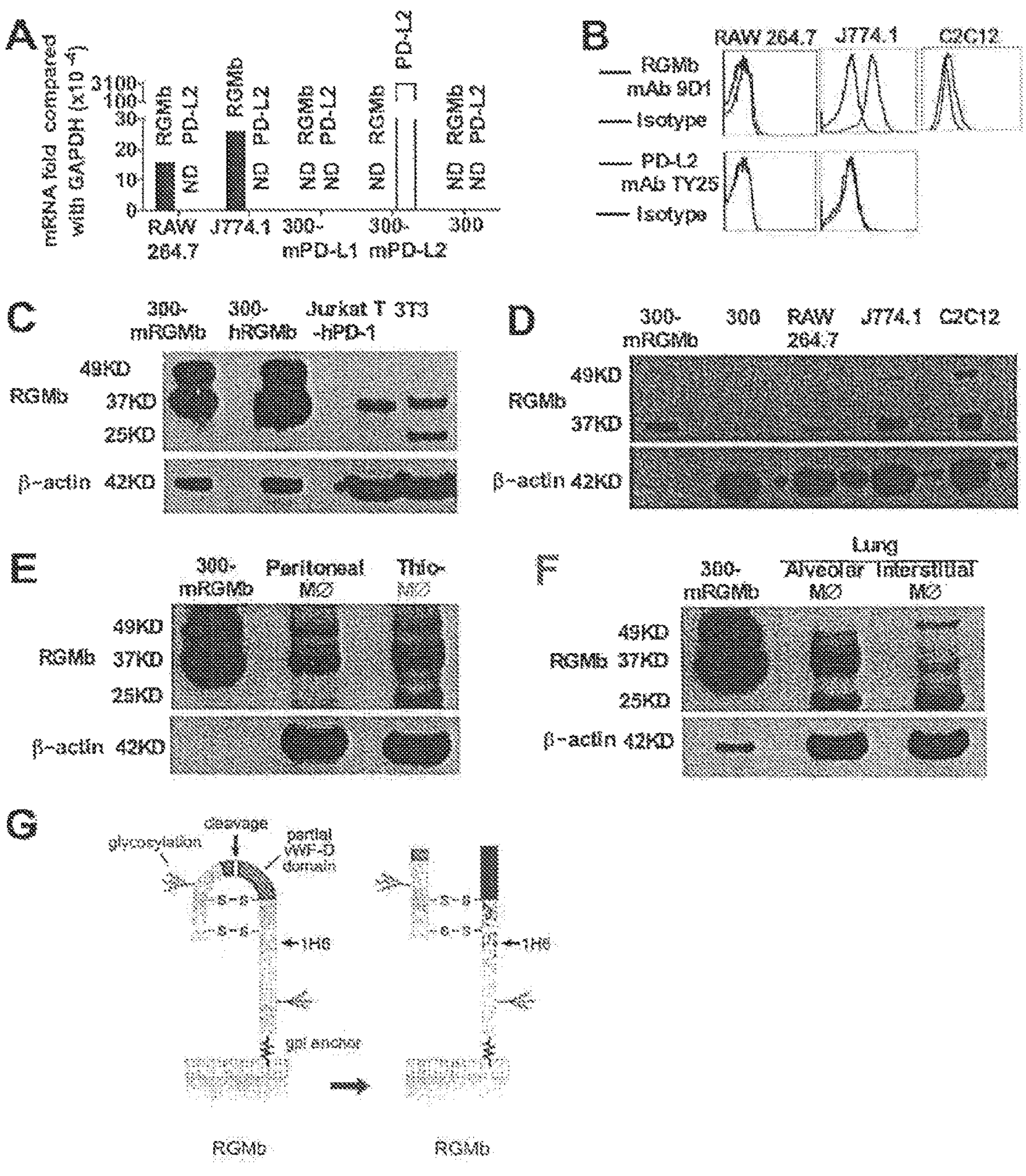
FIGS. 5A-5G show the RGMb expression in mouse macrophages and the RGMb protein structure.

FIG. 5G shows how proteolytic cleavage of RGMb accounts for these multiple protein bands. RGMb contains a portion of a von Willebrand Factor (vWF) type D domain with a proteolytic cleavage site between Asp171 and Pro172. After cleavage, the two fragments of RGMb remain connected by disulfide bond(s). The molecular weight of uncleaved RGMb is predicted to be 40 kD and cleaved RGMb will have N-terminal and C-terminal fragments of 13 kD and 27 kD, respectively. Each fragment has one predicted N-linked glycosylation site, which should increase the molecular weight of each fragment by 5-10 kD. The 1H6 mAb reacts with an epitope in the C-terminal fragment and recognizes the 37 kD cleaved form as well as the 49 kD uncleaved form. The Western blotting analysis shows that most native RGMb is the cleaved form.

Example 7

Figure 6:
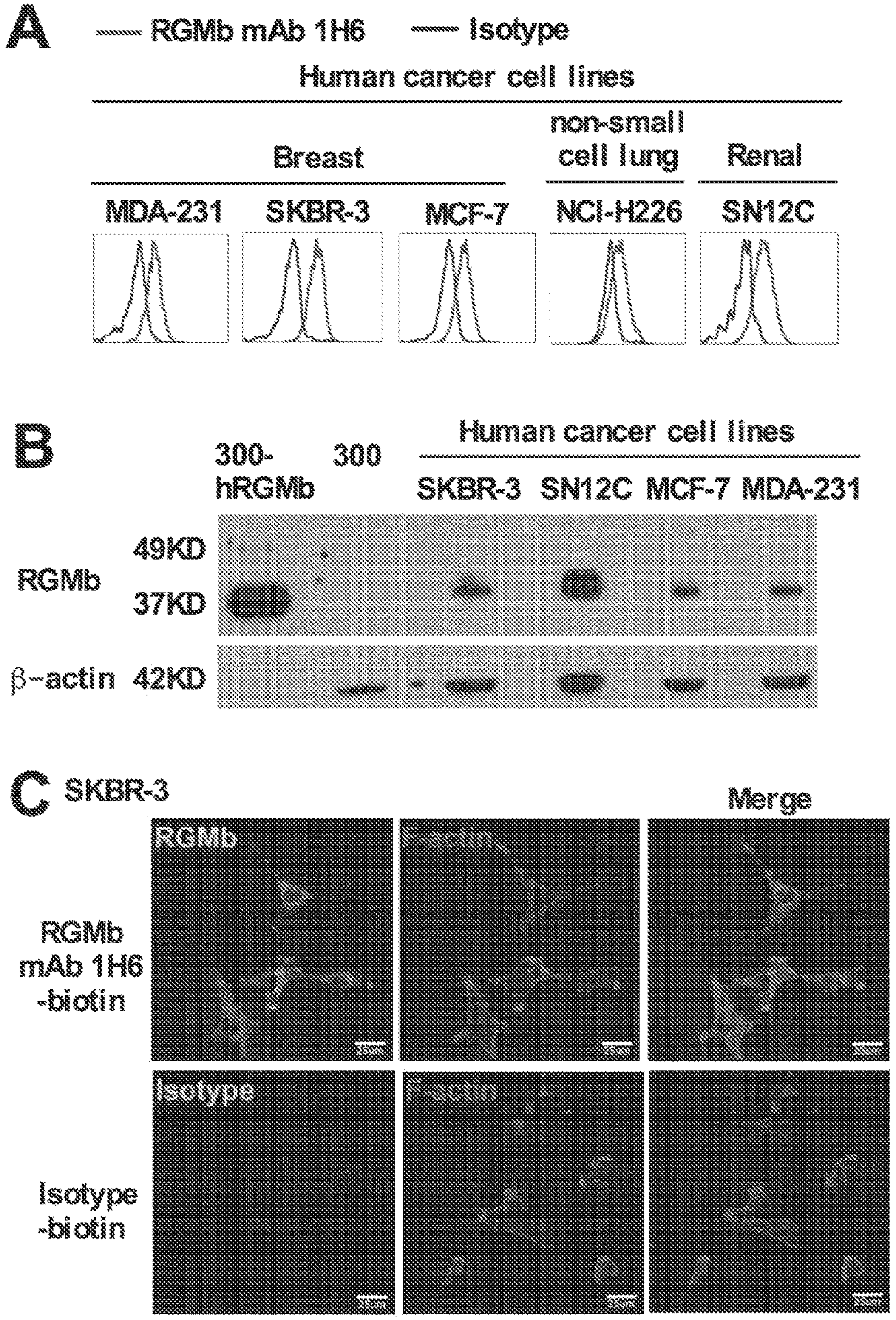
FIGS. 6A-6C show the cell surface and intracellular expression of RGMb by human cancer cell lines.

Cell Surface and Intracellular Expression of RGMb by Human Cancer Cell Lines Previous studies have reported RGMb in breast and prostate tumor cells (Li et al. (2012) *Int. J. Oncol.* 40:544-550 and Li et al. (2012) *J. Cell Biochem.* 113:2523-2531). Both RGMb and PD-L2 were shown to be expressed on the cell surface of the human breast cancer cell lines, MDA-231, SKBR-3, and MCF-7, the human non-small cell lung cancer cell line NCI-H226, as well as the human renal cancer cell line SN12C. using flow cytometry analysis (FIG. 6A). These expression results were confirmed by Western blotting (FIG. 6B). The localization of RGMb in SKBR-3 cells by confocal microscopy showed substantial amounts of RGMb inside the cell, although it is detectable on the cell surface (FIG. 6C). This is in agreement with an immunohistochemical study by Li et al. (2012) *Int. J. Oncol.* 40:544-550 showing RGMb primarily in the cytoplasm of prostate tumor cells.

Example 8

Intracellular Expression of RGMb by Mouse Primary Hematopoietic Cells

Figure 7:
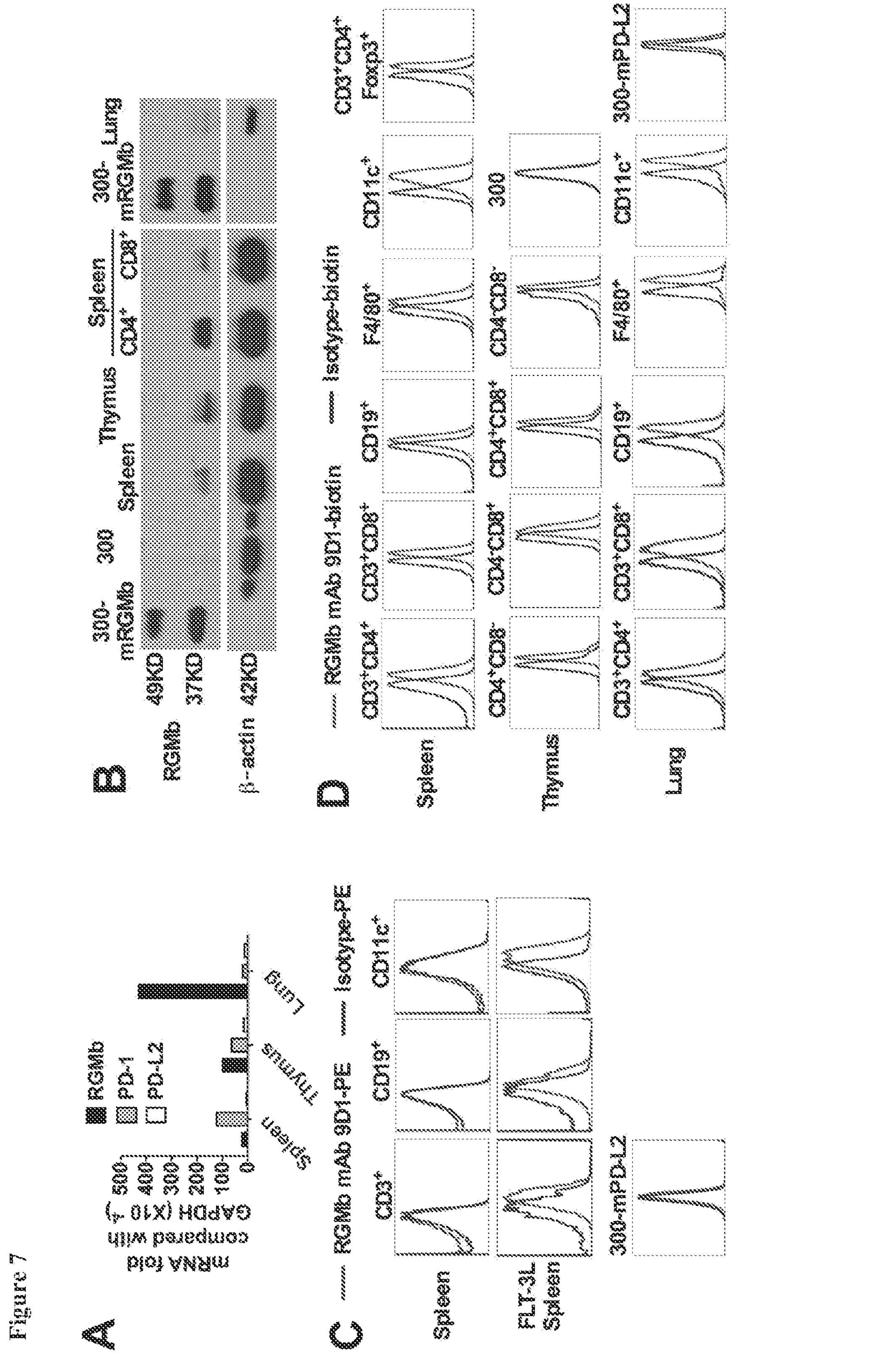
FIGS. 7A-7D show the intracellular expression of RGMb by mouse primary hematopoietic cells.

Real-time RT-PCR and Western blotting showed RGMb expression in spleen, thymus, and lung cells, as well as in purified splenic CD4+ and CD8+ T cells from naïve mice (FIGS. 7A-7B). However, cell surface RGMb expression was not detectable by flow cytometry with PE or biotin-conjugated RGMb mAb 9D1. RGMb mRNA and protein levels were not upregulated in T cells by CD3 and/or CD28 activation, indicating that RGMb is not a T cell activation molecule. Intracellular flow cytometry staining using PE-conjugated RGMb mAb 9D1 did not detect RGMb expression in splenic T cells (CD3+), B cells (CD19+), or DCs (CD11c+) from naïve mice (FIG. 7C, upper panel), but low levels of RGMb expression were detected in these cells from mice treated with FMS-like tyrosine kinase 3 ligand (FLT-3L) to expand DC populations (FIG. 7C, middle panel). Using the strong biotin/strepavidin-PE system and intracellular staining, low levels of RGMb protein were detected in unstimulated cells from mouse spleen, thymus, and lung (FIG. 7D). The findings of intracellular RGMb expression are in agreement with the intracellular expression seen in confocal microscopy of SKBR-3 cells (FIG. 6C) and immunohistochemical staining of cancer cells (Li et al. (2012) Int. J. Oncol. 40:544-550).

Example 9

Blockade of RGMb:PD-L2 Interaction Inhibits the Induction of Respiratory Tolerance PD-L2 blockade has particularly strong effects on immune responses in the lung (Akbari et al. (2010) *Mucosal Immunol.* 3:81-91 and Singh et al. (2010) *Allergy* 66:155-162) and RGMb is highly expressed in the lung (FIG. 7A). Notably, pneumonitis is the most severe adverse event reported in human clinical trials of PD-1 mAb (Topalian et al. (2012) N. Engl. J. Med. 366:2443-2454). Therefore, the role of PD-L2 and RGMb in a mouse model of OVA-induced respiratory tolerance was investigated.

Figure 8:
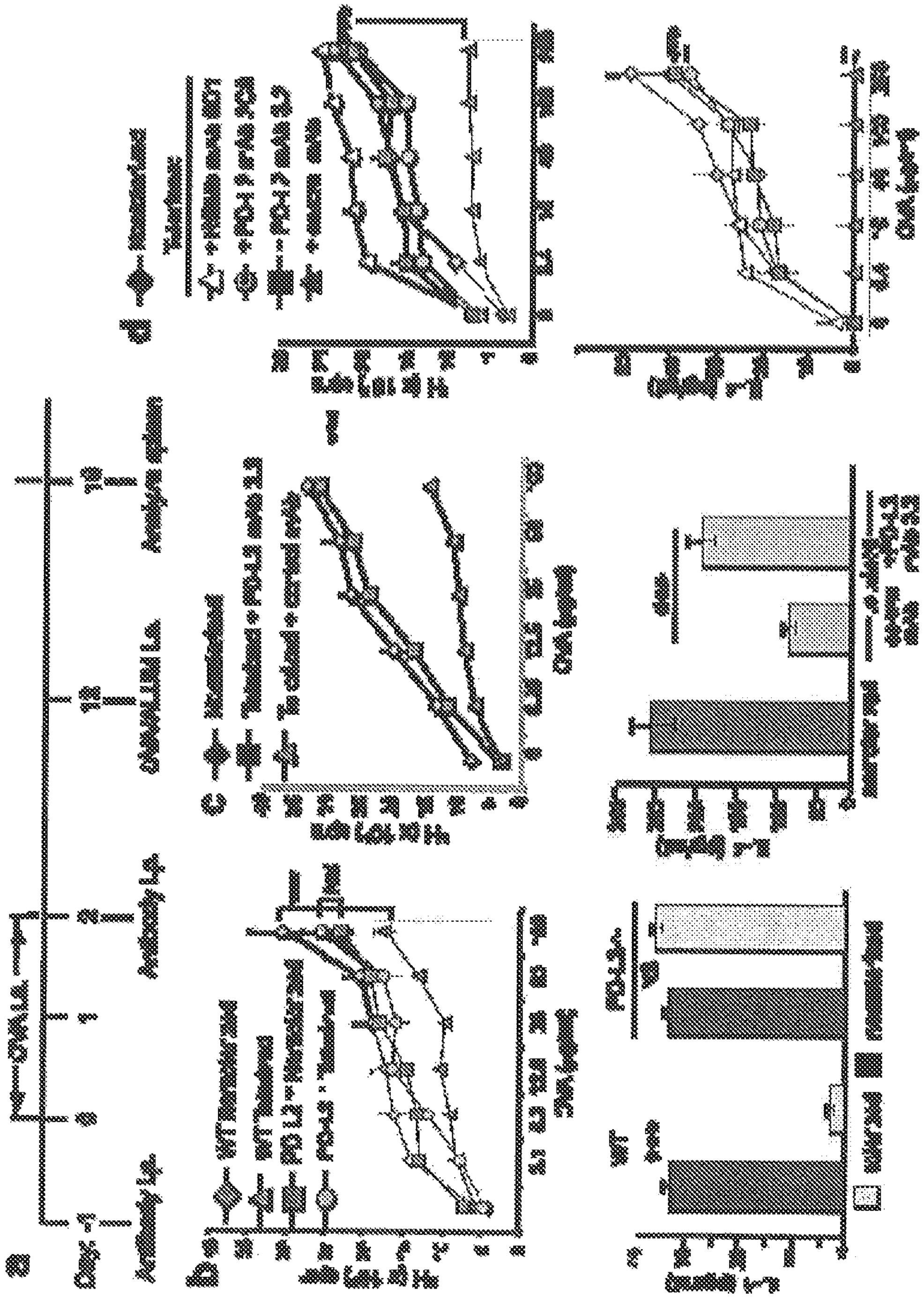
FIG. 8A-8D show that blockade of RGMb:PD-L2 interaction inhibits the induction of respiratory tolerance.

Respiratory tolerance is a state of antigen-specific immunological non-responsiveness induced by exposure to innocuous antigens inhaled in the respiratory tract. The development of respiratory tolerance in wild type (WT) and PD-L2 deficient mice was compared. To induce tolerance, mice were exposed intranasally (i.n.) to OVA or PBS control on days 0, 1, and 2. Mice were challenged by immunization with OVA in alum i.p. on day 12, and splenic T cell responses were examined one week later by in vitro restimulation of T cells with antigen (FIG. 8A). T cells from WT mice exposed to intranasal OVA were tolerized, as evidenced by significantly reduced T cell proliferation and IL-4 responses compared with control mice that did not receive i.n. OVA (FIG. 8B). Strikingly, PD-L2 deficient mice were resistant to the development of respiratory tolerance. T cells from PD-L2 deficient mice that received OVA i.n. displayed similar levels of proliferation and IL-4 production as T cells from control PD-L2 deficient mice that received PBS i.n. Similarly, treatment of WT mice with a PD-L2 mAb (3.2) that blocks both PD-L2:RGMb and PD-L2:PD-1 interaction prevented the development of respiratory tolerance, resulting in increased proliferation and cytokine responses compared to tolerized mice treated with control mAb (FIG. 8C). These results indicate that PD-L2 is critical for the development of respiratory tolerance.

Since PD-L2 can interact with both PD-1 and RGMb, specific mAbs were used to evaluate the contribution of RGMb in development of respiratory tolerance. Mice were treated with RGMb mAb 9D1 (blocks RGMb:PD-L2 and RGMb:BMP), with PD-L2 mAb 2C9 (blocks RGMb:PD-L2 but not PD-1:PD-L2), or with isotype control mAb. Administration of either 2C9 or 9D1 mAb to mice that received OVA i.n. inhibited the development of respiratory tolerance and led to higher levels of T cell proliferation and IL-4 production compared to T cells from mice that received control mAb (FIG. 8D). These results indicate a role for the RGMb:PD-L2 interaction in promoting the development of respiratory tolerance.

Example 10

Blockade of RGMb:PD-L2 Interaction Impairs T Cell Expansion to Antigen During the Development of Tolerance Previous studies of respiratory tolerance showed that intranasal administration of antigen, such as house dust mite (Hoyne et al. (1996) *Int. Immunol.* 8:335-342) or OVA (Albacker et al. (2012) *Mucosal Immunol.* 6:580-590 and Tsitoura et al. (1999) *J. Immunol.* 163:2592-2600), induced a strong transient CD4+ T cell response followed by deletion of most of the antigen-specific T cells. During the development of respiratory tolerance, inhaled antigen is sampled by immature DCs in the lung, which migrate to the draining mediastinal LNs where they encounter antigen-specific T cells. In the absence of inflammatory stimuli, DCs induce transient antigen-specific T cell activation followed by T cell deletion and unresponsiveness (Hawiger et al. (2001) *J. Exp. Med.* 194:769-779). Respiratory tolerance involves multiple mechanisms, including deletion of antigen-specific T cells and the development of anergy and regulatory T cells (Tregs), and these processes may occur concurrently (Albacker et al. (2012) *Mucosal Immunol.* 6:580-590; Bedoret et al. (2009) *J. Clin. Invest.* 119:3723-3738; Geurts van Kessel et al. (2008) *Mucosal Immunol.* 1:442-450; Holt et al. (2004) *Curr. Opin. Allergy Clin. Immunol.* 4:39-44).

Figure 9:
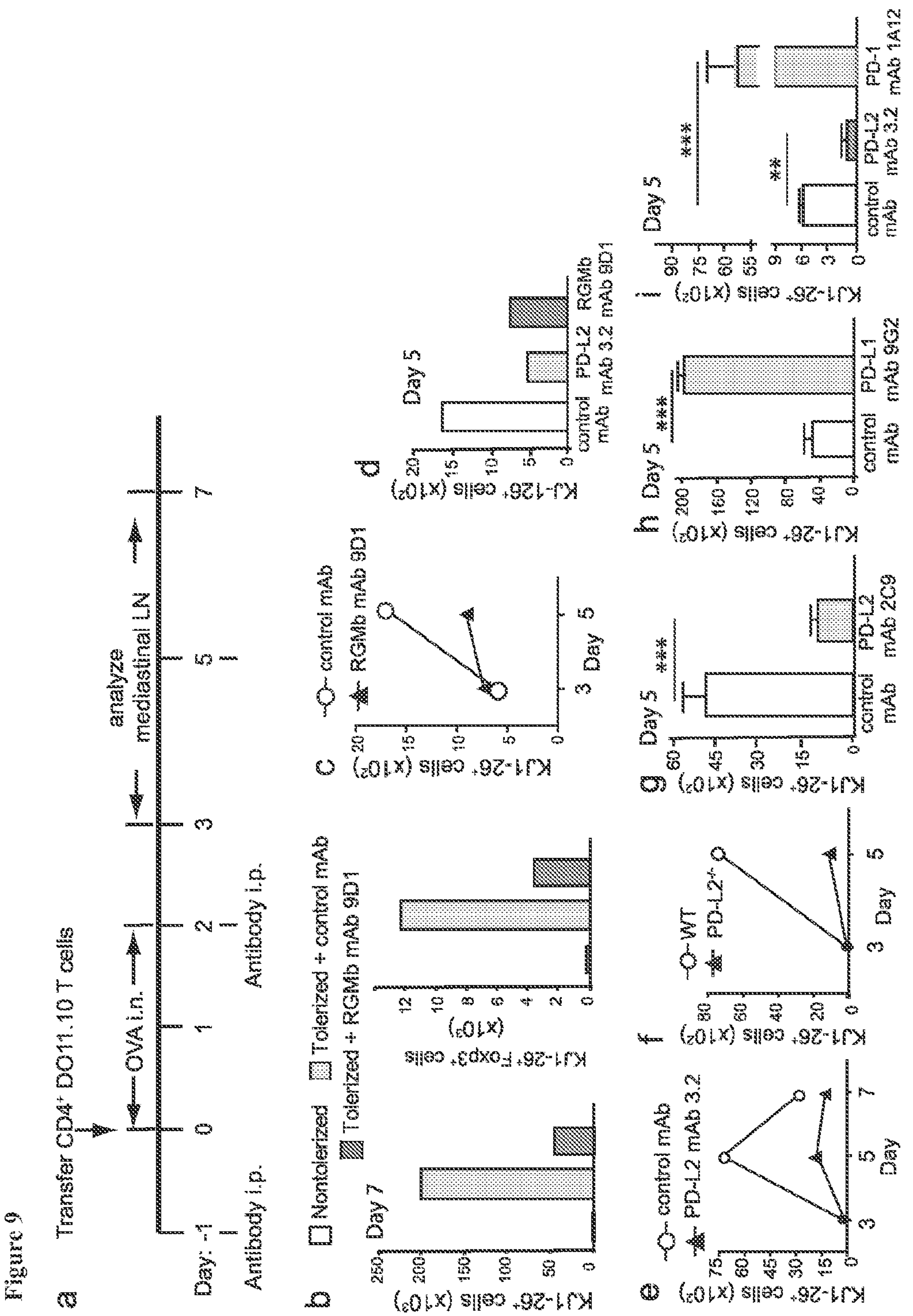

To explore the mechanism whereby RGMb and PD-L2 interaction enhances respiratory tolerance, the effect of blocking RGMb:PD-L2 interaction on the activation and expansion of transferred OVA-specific DO11.10 CD4+ T cells was examined. Recipient mice were treated with RGMb mAb 9D1 or control mAb, subsequently given OVA or PBS intranasally on days 0, 1 and 2, and the fate of DO11.10 T cells was monitored using the clonotypic mAb KJ1-26 (FIG. 9A). As expected, exposure of the mice to i.n. OVA resulted in marked expansion of the DO11.10 cells in the mediastinal LN on day 7 compared with mice that received i.n. PBS. Notably, this expansion of KJ1-26+ T cells was greatly diminished in tolerized mice treated with anti-RGMb compared with the control mAb treated mice (FIG. 9B, left). The number of OVA-specific Treg cells (KJ1-26+Foxp3+) was similarly reduced in RGMb mAb-treated mice, indicating that the reduced expansion of KJ1-26+ T cells was not due to increased numbers of OVA-specific Treg cells (FIG. 9B, right).

The effect of RGMb mAb on the expansion of KJ1-26+ T cells at earlier time points was also examined. Similar numbers of KJ1-26+ cells were detected in LNs of RGMb mAb- and control-treated mice on day 3. However, by day 5, the number of KJ1-26+ cells increased in the control mice, but showed little expansion in the RGMb mAb treated group (FIG. 9C). These findings indicate that blockade of RGMb inhibits the induction of tolerance by impairing the expansion of T cells that normally occurs following respiratory administration of OVA.

To determine if treatment with PD-L2 mAb would similarly inhibit the response of OVA-specific CD4+ T cells following exposure to OVA i.n., mice were treated with PD-L2 mAb, RGMb mAb or control mAb and the number of KJ1-26+ cells examined on day 5. Reduced numbers of KJ1-26+ cells were detected in both PD-L2 mAb and RGMb mAb-treated groups compared with control mAb treated mice, indicating that expansion of KJ1-26+ cells was inhibited (FIG. 9D). To determine if anti-PD-L2 mAb was altering the time course of the T cell response, the in vivo response of DO11.10 T cells to i.n. OVA over a 7 day period in mice treated with PD-L2 mAb or control mAb was examined (FIG. 9E). In control mice, the number of KJ1-26+ cells in mediastinal LNs increased substantially after day 3, peaking at day 5 and declining afterwards as previously described in Tsitoura et al. (1999) *J. Immunol.* 163:2592-2600. In mice treated with PD-L2 mAb, a limited increase in the number of KJ1-26+ cells was observed between days 3 and 5, with a subsequent decline, indicating that blocking PD-L2 inhibited the expansion of OVA-specific T cells throughout the response. The expansion of WT KJ1-26+ T cells following transfer to PD-L2 deficient or WT mice and exposure to OVA i.n. was also compared. Between days 3 and 5, the KJ1-26+ cells underwent a 72-fold expansion in WT recipients but only a 9.7-fold expansion in PD-L2−/− recipients (FIG. 9F). This confirms the importance of PD-L2 for this initial expansion and indicates that PD-L2 expression on non-T cells is necessary for this expansion.

To further dissect this interaction and determine the involvement of the PD-1:PD-L2 vs. RGMB: PD-L2 pathway in this process, mice were treated with PD-L2 mAb 2C9 which blocks only the RGMb:PD-L2 interaction or with control mAb. The expansion of KJ1-26+ cells on day 5 was significantly reduced in mice treated with mAb 2C9 compared with control-treated mice (FIG. 9G), indicating that PD-1 is not required for this effect since 2C9 does not block the interaction of PD-L2 with PD-1. Together, these data indicate that blocking RGMb:PD-L2 interaction prevents the induction of respiratory tolerance, and does so by reducing the initial expansion of CD4+ T cells in response to OVA by a pathway that does not involve PD-1.

The effects of blocking PD-L1 or PD-1 compared to PD-L2 on the initial activation and expansion of transferred DO11.10 OVA-specific CD4+ T cells was next examined. On day 5, mice treated with the blocking PD-L1 mAb 9G2 or PD-1 mAb 1A2 had substantially higher numbers of KJ1-26+ cells in the mediastinal LNs than control mAb-treated mice (FIGS. 9H-91), which indicated that blocking PD-1 or PD-L1 engagement significantly increased the expansion of OVA-specific T cells in response to OVA i.n. In contrast, in mice treated with PD-L2 mAb, the number of KJ1-26+ cells was significantly lower than in control treated mice (FIG. 91). These data further indicate that RGMb:PD- L2 interaction reduces the initial expansion of CD4+ T cells in response to OVA by a pathway that does not involve PD-1.

Together, these data show that PD-L2 plays a critical role in development of respiratory tolerance and that the PD-L2: RGMb interaction promotes the induction of respiratory tolerance by supporting the initial expansion of CD4+ T cells in response to tolerogenic OVA. This expansion is required for tolerance induction and is followed by deletion of Ag-specific T cells. Wild type T cells transferred into PD-L2 deficient mice do not undergo the initial T cell expansion involved in tolerance, indicating that PD-L2 expression on non-T cells provides a required signal.

Example 11

Expression of RGMb, PD-L2, BMP, BMPR and Related Molecules on Lung Cells Subsets, Airway Epithelial Cells and 300 Cells To explore the lung cell subsets involved in RGMb:PD-L2 interaction to promote respiratory tolerance, the expression of RGMa, RGMb, RGMc, BMP-2/4/6, BMP type I and type II receptors, neogenin (binds to RGMb), netrin 1 (binds to negoenin), PD-1, PD-L1, PD-L2, B7-1, and B7-2 was analyzed on lung cell subsets using real-time RT-PCR (FIGS. 10A-10G). The lung cell populations analyzed were interstitial macrophages (IMs, F4/80+CD11c−), alveolar macrophages (AMs, F4/80+CD11c+), dendritic cells (DCs, F4/80-CD11c+) and other cells (F4/80-CD11c−). The expression of RGMa, RGMb, BMP-2/4/6, BMP type I and type II receptors, neogenin, and netrin 1 in IMs was markedly higher than in AMs, while PD-L2 expression was highest in DCs and very low in IMs and AMs. A previous study reported that IMs, but not AMs, were found to produce high levels of IL-10 and to inhibit LPS-induced maturation and migration of DCs, thus preventing airway allergy in mice (Bedoret et al. (2009) *J. Clin. Invest.* 119:3723-3738). It was also found that IMs expressed much higher levels of IL-10 than the three other lung cell subsets (FIG. 10H). These data, together with the interaction model proposed above (FIG. 4C), indicate that RGMb, BMP-2/4 and BMP receptors on IMs may interact with PD-L2 on DCs to form a complex to induce IL-10 production in IMs and inhibit the maturation and migration of DCs, which promote respiratory tolerance.

Figure 10:
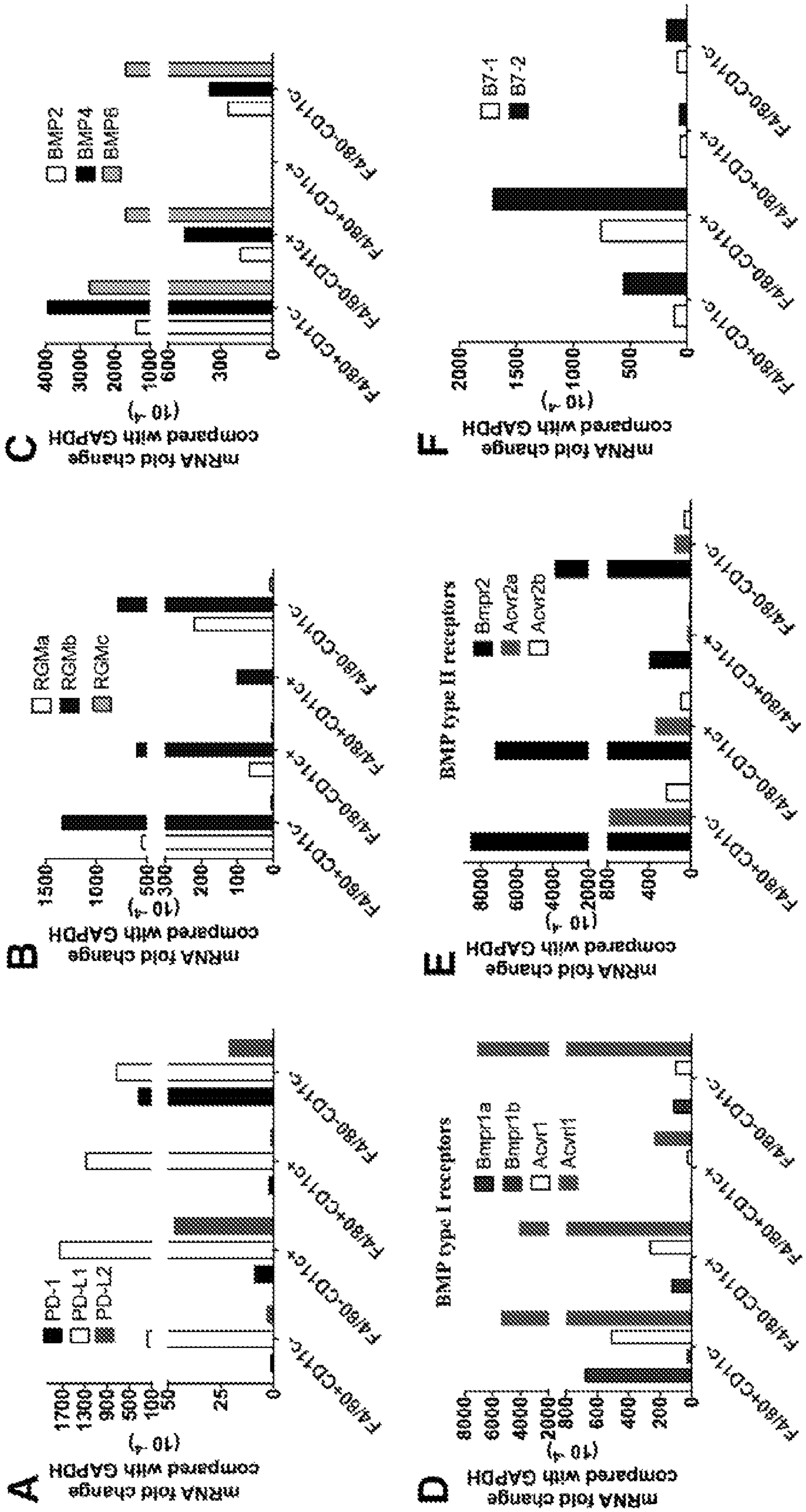
FIG. 10A-10J show the expression of RGMb, PD-L2, BMP, BMPR and related molecules on lung cells subsets, airway epithelial cells and 300 cells. From left to right, each data box of each graph corresponds to the corresponding position of the legend from top to bottom (e.g., data boxes from left to right in FIG. 10A correspond to PD-1, PD-L1, and PD-L2).
Figure 10:
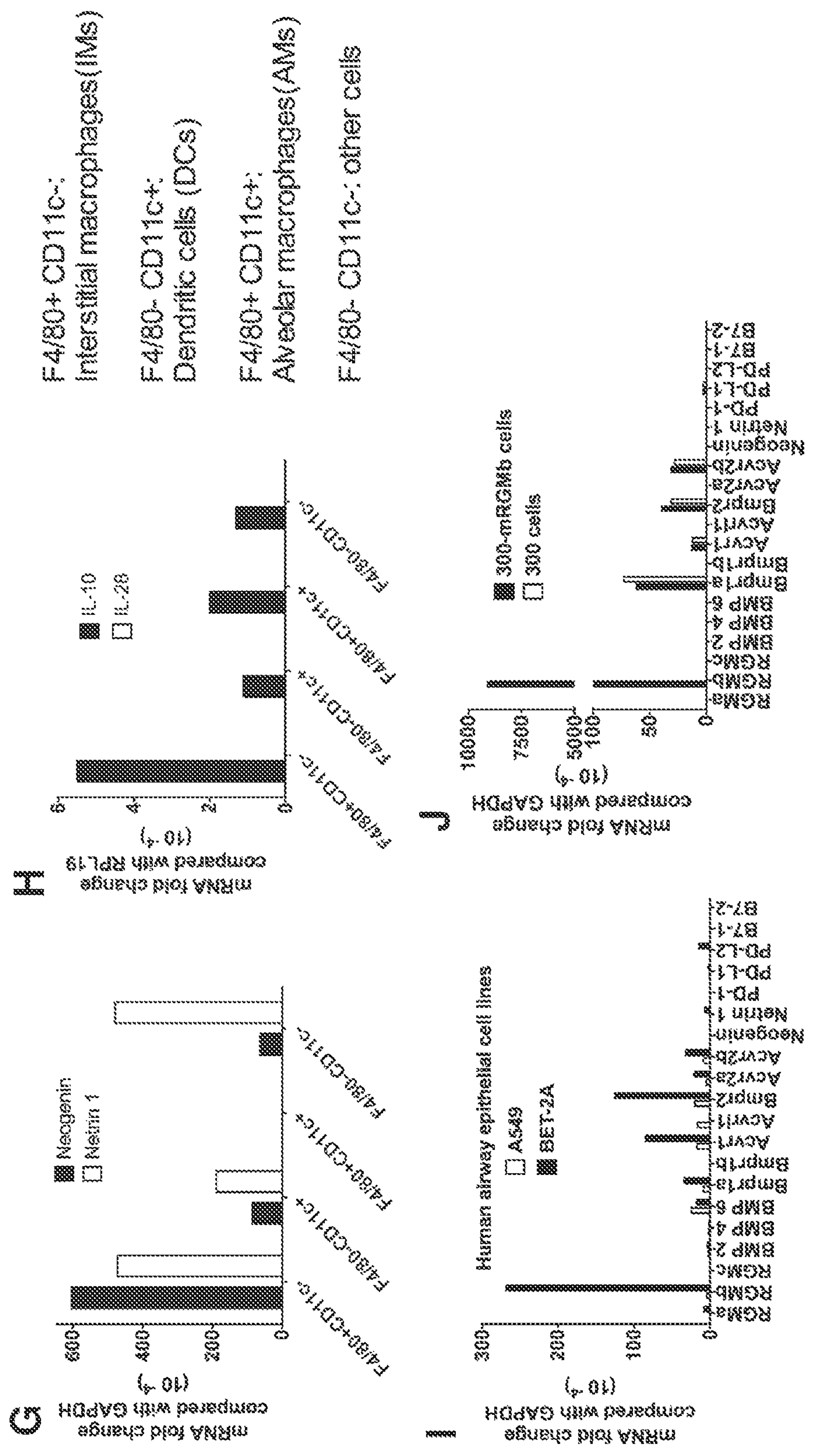

Since airway epithelial cells are also important in respiratory tolerance, the expression of the above molecules on human airway epithelial cell lines A549 and BET-2A was analyzed using real-time RT-PCR. A549 cells had very low levels of expression of all these molecules and BET-2A had a moderate level of RGMb expression and low levels of expression of the other molecules (FIG. 10I). These data indicate that lung epithelial cells may not be the cell type accounting for the high expression of RGMb. BMPs and BMP receptors in lung cells.

To see if a complex of RGMb:PD-L2:BMP-2/4:BMP receptors exists on transfected 300 cells which could be used for study of the complex, the expression of the above molecules on 300 cells and RGMb-transfected 300 cells using real-time RT-PCR. 300 cells had very low or no expression of these molecules and there was no induced expression on RGMb-transfected 300 cells (FIG. 10J). These data indicate that the binding of 300-RGMb cells to 300-PD-L2 cells is independent of BMPs and BMP receptors.

Example 12

Blockade of RGMb and PD-L2 Engagement Delays Disease Onset and Reduces Disease Incidence and Severity in a Mouse Model of Autoimmune Disease The effect of RGMb/PD-L2 engagement blockade was tested in the experimental autoimmune encephalitis (EAE) mouse model of multiple sclerosis. EAE mice were produced by immunization with myelin oligodendrocyte glycoprotein (MOG) and treatment with pertussis toxin (PT) as described in Chang et al. (1999) *J. Exp. Med.* 190(5):733-40.

Mice were treated with anti-RGMb antibody 9D1 or an irrelevant isotype control antibody. Antibodies were injected on the day prior to MOG/PT immunization (400 μg) and on days 2, 5, 8 and 11 following MOG/PT immunization (200 μg/injection).

Figure 11:
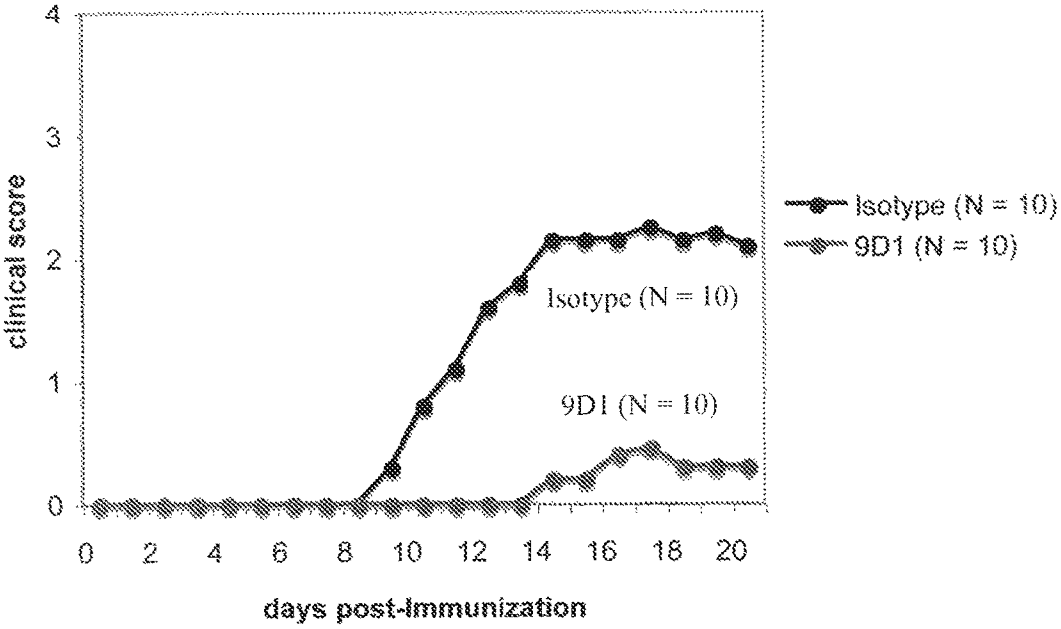
FIG. 11 shows a plot of EAE clinical score over time for both anti-RGMb antibody 9D1-treated and control-treated mice.

Mice were observed daily for clinical signs of EAE, and scored on a scale of 0-5: 0 (no disease): 1 (limp tail); 2 (hind limb weakness): 3 (hind limb paralysis): 4 (hind and fore limb paralysis); and 5 (moribund state). Mean clinical score was calculated by averaging the scores of all mice in each group. Treatment with 9D1 resulted in substantial protection from EAE, delaying onset of EAE symptoms (day 14 for 9D1 compared to day 9 for control) and reducing both the severity (maximum mean score of 0.45 for 9D1 compared to 2.45 for control) and incidence of EAE symptoms (3/10 mice with 9D1 as compared to 10/10 mice for control). Results are shown in graph form in FIG. 11, which plots EAE clinical score over time for both 9D1 and control treated mice.

Example 13

RGMb in Oral Tolerance

In contrast to the enteric nervous system, RGMb expression in the intestinal epithelium starts during postnatal gut development. Both RGMa and RGMb are predominantly expressed in the proliferative crypt compartment of the gut epithelium and in paneth cells of small intestine. The development-dependent expression in enteric ganglia and intestinal epithelial cells suggests that RGM may be involved in cell migration, differentiation, and apoptosis (Metzger et al. (2005) *Dev. Dyn.* 234:169-175). Also, PD-L2−/− mice are reported to be resistant to the development of oral tolerance. (Zhang et al. (2006) *Proc. Natl. Acad. Sci. USA* 103:11695-11700). Since PD-L2 can interact with RGMb, the effect of blocking RGMb during the induction of oral tolerance was determined.

Figure 12:
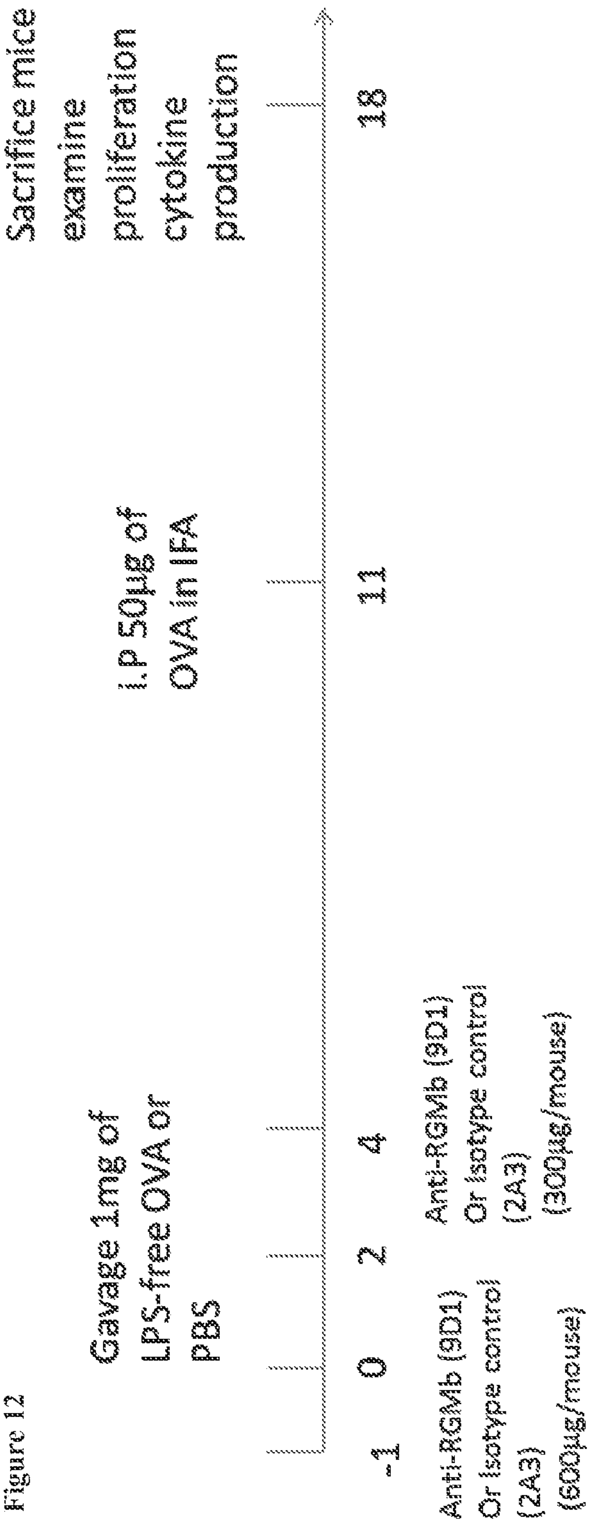
FIG. 12 shows the protocol of the low dose model of oral tolerance used to demonstrate that blockade of RGMb inhibits the induction of oral tolerance
Figure 13:
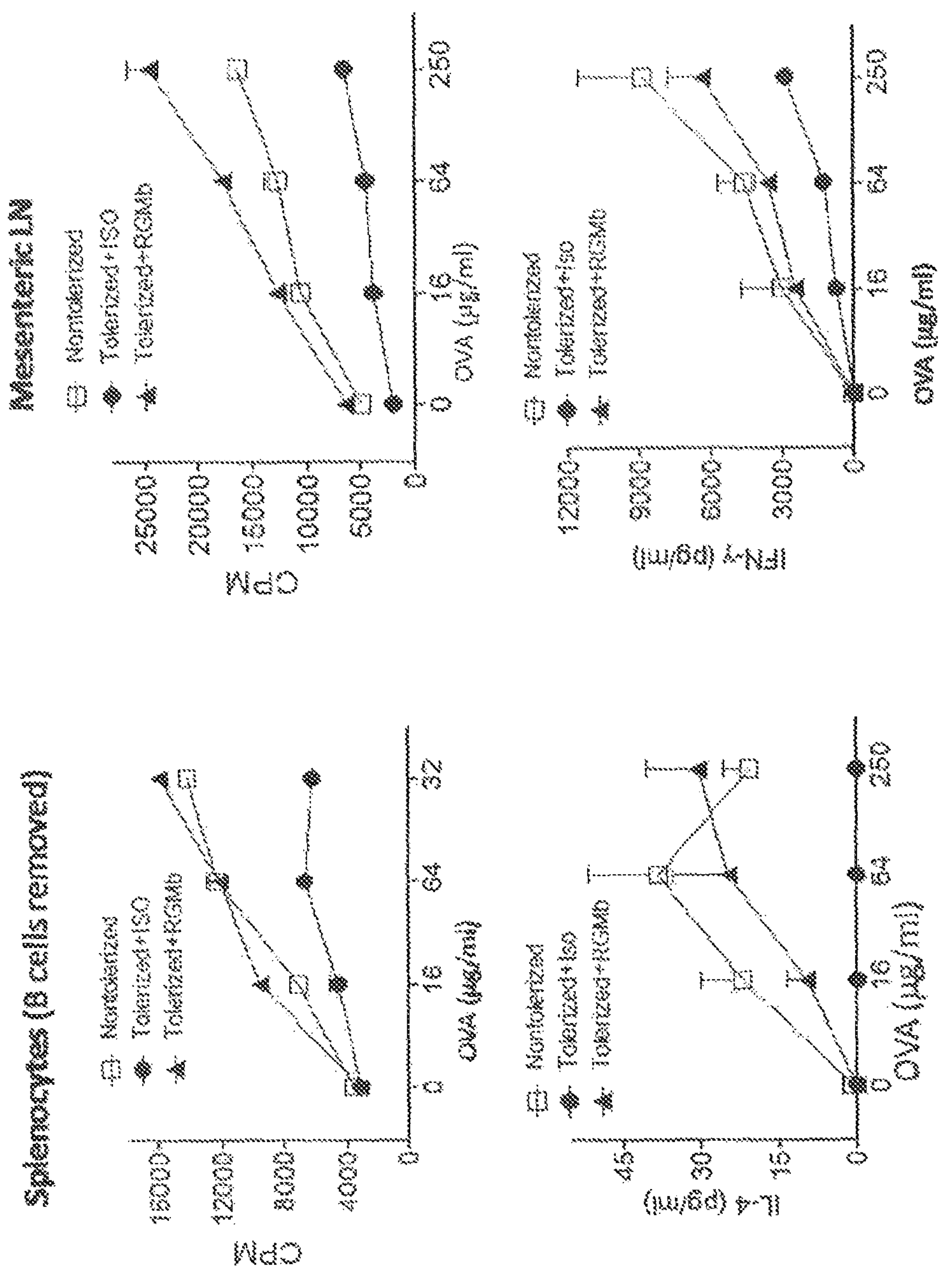
FIG. 13 shows that treatment of mice with anti-RGMb mAb 9D1 prevents the development of oral tolerance, resulting in increased proliferation and cytokine responses compared to tolerized mice treated with control mAb.

FIG. 12 shows the protocol of the low dose model of oral tolerance used to demonstrate that blockade of RGMb inhibits the induction of oral tolerance. Specifically, treatment of mice with anti-RGMb mAb 9D1 prevented the development of oral tolerance, resulting in increased proliferation and cytokine responses compared to tolerized mice treated with control mAb (FIG. 13). These data indicate that RGMb plays an important role in the development of oral tolerance.

What is claimed is:

1. A method for upregulating an immune response comprising contacting a cell expressing RGMb with an agent that inhibits the interaction of PD-L2 with RGMb to thereby upregulate the immune response, wherein the agent is a blocking monoclonal antibody that binds RGMb, or an antigen-binding fragment thereof, comprising six CDRs: CDR-L1, CDR-L2, CDR-L3, CDR-H1, CDR-H2, and CDR-H3, wherein the CDR-L1 sequence consists of amino acid residues 44-54 of SEQ ID NO:12, CDR-L2 sequence consists of amino acid residues 70-76 of SEQ ID NO:12, the CDR-L3 sequence consists of amino acid residues 109-116 of SEQ ID NO:12, the CDR-H1 sequence consists of amino acid residues 50-54 of SEQ ID NO:14, the CDR-H2 sequence consists of amino acid residues 69-85 of SEQ ID NO:14, and the CDR-H3 sequence consists of amino acid residues 118-125 of SEQ ID NO:14.

2. A method of treating a subject having a condition that would benefit from upregulation of an immune response comprising administering to the subject an agent that inhibits the interaction between RGMb and PD-L2 such that the condition that would benefit from upregulation of an immune response is treated, wherein the agent is a blocking monoclonal antibody that binds RGMb, or an antigen-binding fragment thereof, comprising six CDRs: CDR-L1, CDR-L2, CDR-L3, CDR-H1, CDR-H2, and CDR-H3, wherein the CDR-L1 sequence consists of amino acid residues 44-54 of SEQ ID NO:12, CDR-L2 sequence consists of amino acid residues 70-76 of SEQ ID NO:12, the CDR-L3 sequence consists of amino acid residues 109-116 of SEQ ID NO:12, the CDR-H1 sequence consists of amino acid residues 50-54 of SEQ ID NO:14, the CDR-H2 sequence consists of amino acid residues 69-85 of SEQ ID NO:14, and the CDR-H3 sequence consists of amino acid residues 118-125 of SEQ ID NO:14.

3. The method of claim 2, wherein the condition that would benefit from upregulation of an immune response is selected from the group consisting of cancer, a viral infection, a bacterial infection, a protozoan infection, a helminth infection, asthma associated with impaired airway tolerance, a neurological disease, multiple sclerosis, and an immunosuppressive disease.

4. The method of claim 1, wherein the cell expressing RGMb is an immune cell.

5. The method of claim 4, wherein the immune cell is selected from the group consisting of a T cell, a B cell, and a myeloid cell.

6. The method of claim 1, wherein anergy, exhaustion, and/or clonal deletion is reduced in the cell by upregulating the immune response.

7. The method of claim 1, further comprising contacting the cell with one or more additional agents that upregulates an immune response.

8. The method of claim 1, wherein the monoclonal antibody or antigen-binding fragment thereof comprises a heavy chain variable sequence with at least about 97% identity to SEQ ID NO:14 and a light chain sequence with at least about 97% identity to SEQ ID NO:12.

9. The method of claim 8, wherein the antigen-binding fragment thereof is selected from the group consisting of Fv, Fav, F(ab')2, Fab', dsFv, scFv, sc(Fv)2, and diabodies fragments.

10. The method of claim 8, wherein the blocking antibody that binds RGMb inhibits the interaction of RGMb with BMP-2/4.

11. The method of claim 8, wherein the blocking antibody that binds RGMb comprises the heavy chain variable sequence of SEQ ID NO:14 and the light chain sequence of SEQ ID NO:12.

12. The method of claim 2, further comprising administering the subject one or more additional agents that upregulates an immune response.

13. The method of claim 2, wherein the monoclonal antibody or antigen-binding fragment thereof comprises a heavy chain variable sequence with at least about 97% identity to SEQ ID NO:14 and a light chain sequence with at least about 97% identity to SEQ ID NO:12.

14. The method of claim 13, wherein the antigen-binding fragment thereof is selected from the group consisting of Fv, Fav, F(ab')2, Fab', dsFv, scFv, sc(Fv)2, and diabodies fragments.

15. The method of claim 13, wherein the blocking antibody that binds RGMb inhibits the interaction of RGMb with BMP-2/4.

16. The method of claim 13, wherein the blocking antibody that binds RGMb i) inhibits induction of respiratory tolerance;

ii) promotes T cell proliferation;

iii) promotes IL-4 production; and/or iv) impairs T cell expansion to antigen in the subject.

17. The method of claim 16, wherein PD-1:PD-L2 signaling is not needed.

18. The method of claim 13, wherein the blocking antibody that binds RGMb comprises the heavy chain variable sequence of SEQ ID NO:14 and the light chain sequence of SEQ ID NO:12.

* * * * *

UNITED STATES PATENT AND TRADEMARK OFFICE

CERTIFICATE OF CORRECTION

PATENT NO. : 10,457,733 B2
APPLICATION NO. : 14/418548
DATED : October 29, 2019
INVENTOR(S) : Gordon J. Freeman et al.

It is certified that error appears in the above-identified patent and that said Letters Patent is hereby corrected as shown below:

In the Specification

At Column 1, after Statement of Rights, Line 18, please replace:
"This invention was made with government support under grant numbers AI056299 and 5HSSN266200500030C awarded by The National Institutes of Health. The government has certain rights in the invention."

With:
-- This invention was made with government support under grant number AI056299 and contract number HHSN266200500030C awarded by The National Institutes of Health. The government has certain rights in the invention. --

Signed and Sealed this
Tenth Day of December, 2019

Andrei Iancu
*Director of the United States Patent and Trademark Office*

SEQUENCE LISTING

```
<160> NUMBER OF SEQ ID NOS: 14

<210> SEQ ID NO 1
<211> LENGTH: 921
<212> TYPE: DNA
<213> ORGANISM: Homo sapiens

<400> SEQUENCE: 1

cactctggtg gggctgctcc aggcatgcag atcccacagg cgccctggcc agtcgtctgg      60

gcggtgctac aactgggctg gcggccagga tggttcttag actccccaga caggccctgg     120

aacccccca ccttctcccc agccctgctc gtggtgaccg aaggggacaa cgccaccttc     180

acctgcagct tctccaacac atcggagagc ttcgtgctaa actggtaccg catgagcccc     240

agcaaccaga cggacaagct ggccgccttc cccgaggacc gcagccagcc cggccaggac     300

tgccgcttcc gtgtcacaca actgcccaac gggcgtgact tccacatgag cgtggtcagg     360

gcccggcgca atgacagcgg cacctacctc tgtggggcca tctccctggc ccccaaggcg     420

cagatcaaag agagcctgcg ggcagagctc agggtgacag agagaagggc agaagtgccc     480

acagcccacc ccagcccctc acccaggtca gccggccagt tccaaaccct ggtggttggt     540

gtcgtgggcg gcctgctggg cagcctggtg ctgctagtct gggtcctggc cgtcatctgc     600

tcccgggccg cacgagggac aataggagcc aggcgcaccg gccagcccct gaaggaggac     660

ccctcagccg tgcctgtgtt ctctgtggac tatggggagc tggatttcca gtggcgagag     720

aagaccccgg agccccccgt gccctgtgtc cctgagcaga cggagtatgc caccattgtc     780

tttcctagcg gaatgggcac ctcatccccc gcccgcaggg gctcagctga cggccctcgg     840

agtgcccagc cactgaggcc tgaggatgga cactgctctt ggcccctctg accggcttcc     900

ttggccacca gtgttctgca g                                               921


<210> SEQ ID NO 2
<211> LENGTH: 288
<212> TYPE: PRT
<213> ORGANISM: Homo sapiens

<400> SEQUENCE: 2

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160
```

```
Arg Ser Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285
```

<210> SEQ ID NO 3
<211> LENGTH: 968
<212> TYPE: DNA
<213> ORGANISM: Homo sapiens

<400> SEQUENCE: 3

```
gcttcccgag gctccgcacc agccgcgctt ctgtccgcct gcagggcatt ccagaaagat      60

gaggatattt gctgtcttta tattcatgac ctactggcat ttgctgaacg catttactgt     120

cacggttccc aaggacctat atgtggtaga gtatggtagc aatatgacaa ttgaatgcaa     180

attcccagta gaaaaacaat tagacctggc tgcactaatt gtctattggg aaatggagga     240

taagaacatt attcaatttg tgcatggaga ggaagacctg aaggttcagc atagtagcta     300

cagacagagg gcccggctgt tgaaggacca gctctccctg ggaaatgctg cacttcagat     360

cacagatgtg aaattgcagg atgcaggggt gtaccgctgc atgatcagct atggtggtgc     420

cgactacaag cgaattactg tgaaagtcaa tgccccatac aacaaaatca accaaagaat     480

tttggttgtg gatccagtca cctctgaaca tgaactgaca tgtcaggctg agggctaccc     540

caaggccgaa gtcatctgga caagcagtga ccatcaagtc ctgagtggta agaccaccac     600

caccaattcc aagagagagg agaagctttt caatgtgacc agcacactga gaatcaacac     660

aacaactaat gagattttct actgcacttt taggagatta gatcctgagg aaaaccatac     720

agctgaattg gtcatcccag gtaatattct gaatgtgtcc attaaaatat gtctaacact     780

gtcccctagc acctagcatg atgtctgcct atcatagtca ttcagtgatt gttgaataaa     840

tgaatgaatg aataacacta tgtttacaaa atatatccta attcctcacc tccattcatc     900

caaaccatat tgttacttaa taaacattca gcagatattt atggaataaa aaaaaaaaaa     960

aaaaaaaa                                                              968
```

<210> SEQ ID NO 4
<211> LENGTH: 245
<212> TYPE: PRT
<213> ORGANISM: Homo sapiens

<400> SEQUENCE: 4

```
Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
```

-continued

```
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Gly Asn Ile Leu Asn Val Ser Ile Lys Ile Cys Leu Thr
225                 230                 235                 240

Leu Ser Pro Ser Thr
                245
```

<210> SEQ ID NO 5
<211> LENGTH: 1553
<212> TYPE: DNA
<213> ORGANISM: Homo sapiens

<400> SEQUENCE: 5

```
cgaggctccg caccagccgc gcttctgtcc gcctgcaggg cattccagaa agatgaggat     60

atttgctgtc tttatattca tgacctactg gcatttgctg aacgcattta ctgtcacggt    120

tcccaaggac ctatatgtgg tagagtatgg tagcaatatg acaattgaat gcaaattccc    180

agtagaaaaa caattagacc tggctgcact aattgtctat tgggaaatgg aggataagaa    240

cattattcaa tttgtgcatg gagaggaaga cctgaaggtt cagcatagta gctacagaca    300

gagggcccgg ctgttgaagg accagctctc cctgggaaat gctgcacttc agatcacaga    360

tgtgaaattg caggatgcag gggtgtaccg ctgcatgatc agctatggtg gtgccgacta    420

caagcgaatt actgtgaaag tcaatgcccc atacaacaaa atcaaccaaa gaattttggt    480

tgtggatcca gtcacctctg aacatgaact gacatgtcag gctgagggct accccaaggc    540

cgaagtcatc tggacaagca gtgaccatca agtcctgagt ggtaagacca ccaccaccaa    600

ttccaagaga gaggagaagc ttttcaatgt gaccagcaca ctgagaatca acacaacaac    660

taatgagatt ttctactgca cttttaggag attagatcct gaggaaaacc atacagctga    720

attggtcatc ccagaactac ctctggcaca tcctccaaat gaaaggactc acttggtaat    780

tctgggagcc atcttattat gccttggtgt agcactgaca ttcatcttcc gtttaagaaa    840
```

```
agggagaatg atggatgtga aaaaatgtgg catccaagat acaaactcaa agaagcaaag    900

tgatacacat ttggaggaga cgtaatccag cattggaact tctgatcttc aagcagggat    960

tctcaacctg tggtttaggg gttcatcggg gctgagcgtg acaagaggaa ggaatgggcc   1020

cgtgggatgc aggcaatgtg ggacttaaaa ggcccaagca ctgaaaatgg aacctggcga   1080

aagcagagga ggagaatgaa gaaagatgga gtcaaacagg gagcctggag ggagaccttg   1140

atactttcaa atgcctgagg ggctcatcga cgcctgtgac agggagaaag gatacttctg   1200

aacaaggagc ctccaagcaa atcatccatt gctcatccta ggaagacggg ttgagaatcc   1260

ctaatttgag ggtcagttcc tgcagaagtg ccctttgcct ccactcaatg cctcaatttg   1320

ttttctgcat gactgagagt ctcagtgttg gaacgggaca gtatttatgt atgagttttt   1380

cctatttatt ttgagtctgt gaggtcttct tgtcatgtga gtgtggttgt gaatgatttc   1440

ttttgaagat atattgtagt agatgttaca attttgtcgc caaactaaac ttgctgctta   1500

atgatttgct cacatctagt aaaacatgga gtatttgtaa aaaaaaaaaa aaa          1553


<210> SEQ ID NO 6
<211> LENGTH: 290
<212> TYPE: PRT
<213> ORGANISM: Homo sapiens

<400> SEQUENCE: 6

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
```

-continued

```
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
        275                 280                 285

Glu Thr
    290


<210> SEQ ID NO 7
<211> LENGTH: 819
<212> TYPE: DNA
<213> ORGANISM: Homo sapiens

<400> SEQUENCE: 7

atgatcttcc tcctgctaat gttgagcctg gaattgcagc ttcaccagat agcagcttta      60

ttcacagtga cagtccctaa ggaactgtac ataatagagc atggcagcaa tgtgaccctg     120

gaatgcaact ttgacactgg aagtcatgtg aaccttggag caataacagc cagtttgcaa     180

aaggtggaaa atgatacatc cccacaccgt gaaagagcca ctttgctgga ggagcagctg     240

cccctaggga aggcctcgtt ccacatacct caagtccaag tgagggacga aggacagtac     300

caatgcataa tcatctatgg ggtcgcctgg gactacaagt acctgactct gaaagtcaaa     360

gcttcctaca ggaaaataaa cactcacatc ctaaaggttc cagaaacaga tgaggtagag     420

ctcacctgcc aggctacagg ttatcctctg gcagaagtat cctggccaaa cgtcagcgtt     480

cctgccaaca ccagccactc caggacccct gaaggcctct accaggtcac cagtgttctg     540

cgcctaaagc cacccccctgg cagaaacttc agctgtgtgt tctggaatac tcacgtgagg     600

gaacttactt tggccagcat tgaccttcaa agtcagatgg aacccaggac ccatccaact     660

tggctgcttc acattttcat cccctcctgc atcattgctt tcattttcat agccacagtg     720

atagccctaa gaaaacaact ctgtcaaaag ctgtattctt caaaagacac aacaaaaaga     780

cctgtcacca caacaaagag ggaagtgaac agtgctatc                            819


<210> SEQ ID NO 8
<211> LENGTH: 273
<212> TYPE: PRT
<213> ORGANISM: Homo sapiens

<400> SEQUENCE: 8

Met Ile Phe Leu Leu Leu Met Leu Ser Leu Glu Leu Gln Leu His Gln
1               5                   10                  15

Ile Ala Ala Leu Phe Thr Val Thr Val Pro Lys Glu Leu Tyr Ile Ile
            20                  25                  30

Glu His Gly Ser Asn Val Thr Leu Glu Cys Asn Phe Asp Thr Gly Ser
        35                  40                  45

His Val Asn Leu Gly Ala Ile Thr Ala Ser Leu Gln Lys Val Glu Asn
    50                  55                  60

Asp Thr Ser Pro His Arg Glu Arg Ala Thr Leu Leu Glu Glu Gln Leu
65                  70                  75                  80

Pro Leu Gly Lys Ala Ser Phe His Ile Pro Gln Val Gln Val Arg Asp
                85                  90                  95

Glu Gly Gln Tyr Gln Cys Ile Ile Ile Tyr Gly Val Ala Trp Asp Tyr
            100                 105                 110

Lys Tyr Leu Thr Leu Lys Val Lys Ala Ser Tyr Arg Lys Ile Asn Thr
        115                 120                 125
```

-continued

```
His Ile Leu Lys Val Pro Glu Thr Asp Glu Val Glu Leu Thr Cys Gln
    130                 135                 140

Ala Thr Gly Tyr Pro Leu Ala Glu Val Ser Trp Pro Asn Val Ser Val
145                 150                 155                 160

Pro Ala Asn Thr Ser His Ser Arg Thr Pro Glu Gly Leu Tyr Gln Val
                165                 170                 175

Thr Ser Val Leu Arg Leu Lys Pro Pro Pro Gly Arg Asn Phe Ser Cys
            180                 185                 190

Val Phe Trp Asn Thr His Val Arg Glu Leu Thr Leu Ala Ser Ile Asp
        195                 200                 205

Leu Gln Ser Gln Met Glu Pro Arg Thr His Pro Thr Trp Leu Leu His
    210                 215                 220

Ile Phe Ile Pro Ser Cys Ile Ile Ala Phe Ile Phe Ile Ala Thr Val
225                 230                 235                 240

Ile Ala Leu Arg Lys Gln Leu Cys Gln Lys Leu Tyr Ser Ser Lys Asp
                245                 250                 255

Thr Thr Lys Arg Pro Val Thr Thr Thr Lys Arg Glu Val Asn Ser Ala
            260                 265                 270

Ile
```

<210> SEQ ID NO 9
<211> LENGTH: 1437
<212> TYPE: DNA
<213> ORGANISM: Homo sapiens

<400> SEQUENCE: 9

```
atgataagga agaagaggaa gcgaagcgcg ccccccggcc catgccgcag ccacgggccc      60

agacccgcca cggcgcccgc gccgccgccc tcgccggagc ccacgagacc tgcatggacg     120

ggcatgggct tgagagcagc accttccagc gccgccgctg ccgccgccga ggttgagcag     180

cgccgcagcc ccgggctctg ccccccgccg ctggagctgc tgctgctgct gctgttcagc     240

ctcgggctgc tccacgcagg tgactgccaa cagccagccc aatgtcgaat ccagaaatgc     300

accacggact tcgtgtccct gacttctcac ctgaactctg ccgttgacgg ctttgactct     360

gagttttgca aggccttgcg tgcctatgct ggctgcaccc agcgaacttc aaaagcctgc     420

cgtggcaacc tggtatacca ttctgccgtg ttgggtatca gtgacctcat gagccagagg     480

aattgttcca aggatggacc cacatcctct accaaccccg aagtgaccca tgatccttgc     540

aactatcaca gccacgctgg agccagggaa cacaggagag gggaccagaa ccctcccagt     600

tacctttttt gtggcttgtt tggagatcct cacctcagaa ctttcaagga taacttccaa     660

acatgcaaag tagaaggggc ctggccactc atagataata attatctttc agttcaagtg     720

acaaacgtac ctgtggtccc tggatccagt gctactgcta caaataagat cactattatc     780

ttcaaagccc accatgagtg tacagatcag aaagtctacc aagctgtgac agatgacctg     840

ccggccgcct ttgtggatgg caccaccagt ggtggggaca gcgatgccaa gagcctgcgt     900

atcgtggaaa gggagagtgg ccactatgtg gagatgcacg cccgctatat agggaccaca     960

gtgtttgtgc ggcaggtggg tcgctacctg acccttgcca tccgtatgcc tgaagacctg    1020

gccatgtcct acgaggagag ccaggacctg cagctgtgcg tgaacggctg cccccctgagt    1080

gaacgcatcg atgacgggca gggccaggtg tctgccatcc tgggacacag cctgcctcgc    1140

acctccttgg tgcaggcctg gcctggctac acactggaga ctgccaacac tcaatgccat    1200

gagaagatgc cagtgaagga catctatttc cagtcctgtg tcttcgacct gctcaccact    1260
```

```
ggtgatgcca actttactgc cgcagcccac agtgccttgg aggatgtgga ggccctgcac   1320

ccaaggaagg aacgctggca cattttcccc agcagtggca atgggactcc ccgtggaggc   1380

agtgatttgt ctgtcagtct aggactcacc tgcttgatcc ttatcgtgtt tttgtag      1437


<210> SEQ ID NO 10
<211> LENGTH: 478
<212> TYPE: PRT
<213> ORGANISM: Homo sapiens

<400> SEQUENCE: 10

Met Ile Arg Lys Lys Arg Lys Arg Ser Ala Pro Pro Gly Pro Cys Arg
1               5                   10                  15

Ser His Gly Pro Arg Pro Ala Thr Ala Pro Ala Pro Pro Pro Ser Pro
            20                  25                  30

Glu Pro Thr Arg Pro Ala Trp Thr Gly Met Gly Leu Arg Ala Ala Pro
        35                  40                  45

Ser Ser Ala Ala Ala Ala Ala Ala Glu Val Glu Gln Arg Arg Ser Pro
    50                  55                  60

Gly Leu Cys Pro Pro Pro Leu Glu Leu Leu Leu Leu Leu Leu Phe Ser
65                  70                  75                  80

Leu Gly Leu Leu His Ala Gly Asp Cys Gln Gln Pro Ala Gln Cys Arg
                85                  90                  95

Ile Gln Lys Cys Thr Thr Asp Phe Val Ser Leu Thr Ser His Leu Asn
            100                 105                 110

Ser Ala Val Asp Gly Phe Asp Ser Glu Phe Cys Lys Ala Leu Arg Ala
        115                 120                 125

Tyr Ala Gly Cys Thr Gln Arg Thr Ser Lys Ala Cys Arg Gly Asn Leu
    130                 135                 140

Val Tyr His Ser Ala Val Leu Gly Ile Ser Asp Leu Met Ser Gln Arg
145                 150                 155                 160

Asn Cys Ser Lys Asp Gly Pro Thr Ser Ser Thr Asn Pro Glu Val Thr
                165                 170                 175

His Asp Pro Cys Asn Tyr His Ser His Ala Gly Ala Arg Glu His Arg
            180                 185                 190

Arg Gly Asp Gln Asn Pro Pro Ser Tyr Leu Phe Cys Gly Leu Phe Gly
        195                 200                 205

Asp Pro His Leu Arg Thr Phe Lys Asp Asn Phe Gln Thr Cys Lys Val
    210                 215                 220

Glu Gly Ala Trp Pro Leu Ile Asp Asn Asn Tyr Leu Ser Val Gln Val
225                 230                 235                 240

Thr Asn Val Pro Val Val Pro Gly Ser Ser Ala Thr Ala Thr Asn Lys
                245                 250                 255

Ile Thr Ile Ile Phe Lys Ala His His Glu Cys Thr Asp Gln Lys Val
            260                 265                 270

Tyr Gln Ala Val Thr Asp Asp Leu Pro Ala Ala Phe Val Asp Gly Thr
        275                 280                 285

Thr Ser Gly Gly Asp Ser Asp Ala Lys Ser Leu Arg Ile Val Glu Arg
    290                 295                 300

Glu Ser Gly His Tyr Val Glu Met His Ala Arg Tyr Ile Gly Thr Thr
305                 310                 315                 320

Val Phe Val Arg Gln Val Gly Arg Tyr Leu Thr Leu Ala Ile Arg Met
                325                 330                 335

Pro Glu Asp Leu Ala Met Ser Tyr Glu Glu Ser Gln Asp Leu Gln Leu
            340                 345                 350
```

```
Cys Val Asn Gly Cys Pro Leu Ser Glu Arg Ile Asp Asp Gly Gln Gly
        355                 360                 365

Gln Val Ser Ala Ile Leu Gly His Ser Leu Pro Arg Thr Ser Leu Val
    370                 375                 380

Gln Ala Trp Pro Gly Tyr Thr Leu Glu Thr Ala Asn Thr Gln Cys His
385                 390                 395                 400

Glu Lys Met Pro Val Lys Asp Ile Tyr Phe Gln Ser Cys Val Phe Asp
                405                 410                 415

Leu Leu Thr Thr Gly Asp Ala Asn Phe Thr Ala Ala Ala His Ser Ala
            420                 425                 430

Leu Glu Asp Val Glu Ala Leu His Pro Arg Lys Glu Arg Trp His Ile
        435                 440                 445

Phe Pro Ser Ser Gly Asn Gly Thr Pro Arg Gly Gly Ser Asp Leu Ser
    450                 455                 460

Val Ser Leu Gly Leu Thr Cys Leu Ile Leu Ile Val Phe Leu
465                 470                 475
```

<210> SEQ ID NO 11
<211> LENGTH: 378
<212> TYPE: DNA
<213> ORGANISM: Artificial Sequence
<220> FEATURE:
<223> OTHER INFORMATION: Antibody 9D1 vK DNA

<400> SEQUENCE: 11

```
atgatggctg cagttcagct cttagggctt ttgctgctct gcctccgagc catgagatgt     60

gacatccaga tgacccagtc tccttcacac ctgtcagcat ctgtgggaga cagagtcact    120

ctcagctgca aagtaagtca gaatatttac aagtacttaa actggtatca gcaaaaactt    180

ggagaagctc ccaaactcct gatatattat acaagctttt tgcaaacggg catcccgtca    240

aggttcagtg gcagtggatc tggtacagat tacacactca ccatcagcag cctgcagcct    300

gaagatgttg ccacatattt ctgccagaag tattatagcg ggtggacgtt cggtggaggc    360

accaagctgg aattgaaa                                                  378
```

<210> SEQ ID NO 12
<211> LENGTH: 126
<212> TYPE: PRT
<213> ORGANISM: Artificial Sequence
<220> FEATURE:
<223> OTHER INFORMATION: Antibody 9D1 vK Protein

<400> SEQUENCE: 12

```
Met Met Ala Ala Val Gln Leu Leu Gly Leu Leu Leu Leu Cys Leu Arg
1               5                   10                  15

Ala Met Arg Cys Asp Ile Gln Met Thr Gln Ser Pro Ser His Leu Ser
            20                  25                  30

Ala Ser Val Gly Asp Arg Val Thr Leu Ser Cys Lys Val Ser Gln Asn
        35                  40                  45

Ile Tyr Lys Tyr Leu Asn Trp Tyr Gln Gln Lys Leu Gly Glu Ala Pro
    50                  55                  60

Lys Leu Leu Ile Tyr Tyr Thr Ser Phe Leu Gln Thr Gly Ile Pro Ser
65                  70                  75                  80

Arg Phe Ser Gly Ser Gly Ser Gly Thr Asp Tyr Thr Leu Thr Ile Ser
                85                  90                  95

Ser Leu Gln Pro Glu Asp Val Ala Thr Tyr Phe Cys Gln Lys Tyr Tyr
            100                 105                 110
```

-continued

```
Ser Gly Trp Thr Phe Gly Gly Gly Thr Lys Leu Glu Leu Lys
        115                 120                 125


<210> SEQ ID NO 13
<211> LENGTH: 408
<212> TYPE: DNA
<213> ORGANISM: Artificial Sequence
<220> FEATURE:
<223> OTHER INFORMATION: Antibody 9D1 vH DNA

<400> SEQUENCE: 13

atgggatgga gccagatcat tctctttctg gtggcagcaa ctacatgtgt ccactcccag      60

gtacagctac agcaatcagg gactgaactg gtgaagcctg ggtcctcagt gaaaatttcc     120

tgcaaggctt ctggcgacac cttcaccagt gactatatgc actggataag gcagcagcct     180

ggaagtggcc ttgagtggat tgggtggatt tatcctggaa atggtaatac taagtacaat     240

caaaagttcg atgggaaggc aacactcact gcagacaaat cctccagcac agcctatttg     300

cagctcagcc tcctgacatc tgaggactat gcagtctatt tctgtgcaag acagacggag     360

gggtactttg attactgggg ccaaggagtc atggtcacag tctcctca                  408


<210> SEQ ID NO 14
<211> LENGTH: 136
<212> TYPE: PRT
<213> ORGANISM: Artificial Sequence
<220> FEATURE:
<223> OTHER INFORMATION: Antibody 9D1 vH Protein

<400> SEQUENCE: 14

Met Gly Trp Ser Gln Ile Ile Leu Phe Leu Val Ala Ala Thr Thr Cys
1               5                   10                  15

Val His Ser Gln Val Gln Leu Gln Gln Ser Gly Thr Glu Leu Val Lys
            20                  25                  30

Pro Gly Ser Ser Val Lys Ile Ser Cys Lys Ala Ser Gly Asp Thr Phe
        35                  40                  45

Thr Ser Asp Tyr Met His Trp Ile Arg Gln Gln Pro Gly Ser Gly Leu
    50                  55                  60

Glu Trp Ile Gly Trp Ile Tyr Pro Gly Asn Gly Asn Thr Lys Tyr Asn
65                  70                  75                  80

Gln Lys Phe Asp Gly Lys Ala Thr Leu Thr Ala Asp Lys Ser Ser Ser
                85                  90                  95

Thr Ala Tyr Leu Gln Leu Ser Leu Leu Thr Ser Glu Asp Tyr Ala Val
            100                 105                 110

Tyr Phe Cys Ala Arg Gln Thr Glu Gly Tyr Phe Asp Tyr Trp Gly Gln
        115                 120                 125

Gly Val Met Val Thr Val Ser Ser
    130                 135
```